United States Patent
Yantasee et al.

(10) Patent No.: US 11,235,058 B2
(45) Date of Patent: Feb. 1, 2022

(54) IMMUNOTHERAPEUTIC CONSTRUCTS AND METHODS OF THEIR USE

(71) Applicants: PDX Pharmaceuticals, Inc., Portland, OR (US); Oregon Health & Science University, Portland, OR (US)

(72) Inventors: Wassana Yantasee, Lake Oswego, OR (US); Amanda Lund, Portland, OR (US); Worapol Ngamcherdtrakul, Portland, OR (US); Moataz Reda, Portland, OR (US)

(73) Assignees: Oregon Health & Science University, Portland, OR (US); PDX Pharmaceuticals, Inc., Portland, OR (US)

( * ) Notice: Subject to any disclaimer, the term of this patent is extended or adjusted under 35 U.S.C. 154(b) by 0 days.

(21) Appl. No.: 16/999,948

(22) Filed: Aug. 21, 2020

(65) Prior Publication Data

US 2021/0008198 A1     Jan. 14, 2021

Related U.S. Application Data

(63) Continuation of application No. PCT/US2020/041844, filed on Jul. 13, 2020.

(60) Provisional application No. 62/873,762, filed on Jul. 12, 2019.

(51) Int. Cl.
| | |
|---|---|
| *C12N 15/113* | (2010.01) |
| *A61K 31/7105* | (2006.01) |
| *A61K 39/39* | (2006.01) |
| *A61K 9/16* | (2006.01) |
| *A61P 35/00* | (2006.01) |
| *A61K 9/00* | (2006.01) |
| *A61K 31/519* | (2006.01) |
| *A61K 39/00* | (2006.01) |

(52) U.S. Cl.
CPC ............ *A61K 39/39* (2013.01); *A61K 9/0014* (2013.01); *A61K 9/0021* (2013.01); *A61K 9/1676* (2013.01); *A61K 31/519* (2013.01); *A61K 31/7105* (2013.01); *A61P 35/00* (2018.01); *C12N 15/113* (2013.01); *C12N 15/1135* (2013.01); *A61K 2039/55561* (2013.01); *C12N 2310/141* (2013.01); *C12N 2320/31* (2013.01); *C12N 2320/35* (2013.01)

(58) Field of Classification Search
None
See application file for complete search history.

(56) References Cited

U.S. PATENT DOCUMENTS

| | | | |
|---|---|---|---|
| 6,406,705 B1 | 6/2002 | Davis et al. | |
| 7,045,356 B2 | 5/2006 | Trubetskoy et al. | |
| 9,884,026 B2 | 2/2018 | Fahmy et al. | |
| 9,885,082 B2 | 2/2018 | Hrdlicka | |
| 9,976,147 B2 | 5/2018 | Kortylewski et al. | |
| 10,285,950 B2 | 5/2019 | Frederick et al. | |
| 2003/0018002 A1 | 1/2003 | Sagara | |
| 2006/0293396 A1 | 12/2006 | Bringley et al. | |
| 2007/0184068 A1 | 8/2007 | Renner et al. | |
| 2008/0051359 A1* | 2/2008 | Karras | A61P 35/02 514/44 A |
| 2008/0214436 A1* | 9/2008 | Yu | A61K 31/713 514/1.1 |
| 2008/0279954 A1 | 11/2008 | Davis et al. | |
| 2009/0110719 A1 | 4/2009 | Roy et al. | |
| 2012/0207795 A1* | 8/2012 | Zink | A61K 31/713 424/400 |
| 2013/0337067 A1 | 12/2013 | Prakash et al. | |
| 2016/0287717 A1 | 10/2016 | Brinker et al. | |
| 2016/0331844 A1* | 11/2016 | Fotin-Mleczek | C07K 16/30 |
| 2016/0333350 A1 | 11/2016 | Kortylewski et al. | |
| 2017/0172923 A1 | 6/2017 | Won | |
| 2017/0173169 A1* | 6/2017 | Yantasee | A61K 38/16 |
| 2018/0049984 A1 | 2/2018 | Brinker et al. | |
| 2018/0071387 A1 | 3/2018 | Coulter et al. | |
| 2018/0078625 A1 | 3/2018 | Moon et al. | |
| 2018/0155189 A1 | 6/2018 | Zink et al. | |
| 2018/0169255 A1 | 6/2018 | Gao et al. | |
| 2018/0200196 A1 | 7/2018 | Fahmy et al. | |
| 2018/0207273 A1 | 7/2018 | Dranoff et al. | |

(Continued)

FOREIGN PATENT DOCUMENTS

| | | |
|---|---|---|
| WO | WO2006076636 A1 | 7/2006 |
| WO | WO2016149378 A1 | 9/2016 |

(Continued)

OTHER PUBLICATIONS

Ngamcherdtrakul et al. Adv Funct Materl. 25:2646-2659 (Year: 2015).*
Cooper et al. AIDS 19: 1473-1479 (Year: 2005).*
Murad et al. Expert Opin Biol Ther 7: pp. 1257-1266 (Year: 2007).*
Argyo, et al., "Multifunctional mesoporous silica nanoparticles as a universal platform for drug delivery," Chem. Mater., vol. 26, No. 1, 2014, pp. 435-451.
Barbe, et al., "Silica Particles: A Novel Drug-Delivery System," Advanced Materials, vol. 16, 2004, pp. 1959-1966.

(Continued)

*Primary Examiner* — Brian Whiteman
(74) *Attorney, Agent, or Firm* — Tanya M. Harding; Lee & Hayes, P.C.

(57) ABSTRACT

Disclosed herein are immunotherapeutic constructs comprising a delivery particle, at least one adjuvant, and one or more therapeutic agents/compounds that cause antigen release and/or modulate immunosuppressive tumor microenvironment. These immunotherapeutic constructs create adaptive immunity or anti-cancer immune response(s) that can be used, for instance, to prevent and treat broad types of cancer. Further disclosed are uses of the immunotherapeutic constructs, including to prevent and treat cancer in humans and animals.

21 Claims, 43 Drawing Sheets

Specification includes a Sequence Listing.

(56) References Cited

U.S. PATENT DOCUMENTS

| | | | |
|---|---|---|---|
| 2018/0312536 | A1 | 11/2018 | Sakamuri et al. |
| 2018/0369375 | A1 | 12/2018 | De Waal Malefyt et al. |
| 2019/0008962 | A1 | 1/2019 | Borghi et al. |
| 2019/0048049 | A1 | 2/2019 | Dasseux |
| 2019/0076545 | A1 | 3/2019 | Santamaria |
| 2019/0374479 | A1 | 12/2019 | Farokhzad et al. |
| 2021/0030679 | A1 | 2/2021 | Yantasee et al. |

FOREIGN PATENT DOCUMENTS

| | | | |
|---|---|---|---|
| WO | WO2016189532 | A1 | 12/2016 |
| WO | WO2017040660 | A1 | 3/2017 |
| WO | WO2017120537 | A1 | 7/2017 |
| WO | WO2021011501 | | 1/2021 |

OTHER PUBLICATIONS

Bharali, et al., "Organically modified silica nanoparticles: A nonviral vector for in vivo gene delivery and expression in the brain," PNAS, vol. 102, No. 32, 2005, pp. 11539-11544.

Bringley, et al., "Controlled, simultaneous assembly of polyethylenimine onto nanoparticle silica colloids," Lanqmuir., vol. 22, No. 9, 2006, pp. 4198-4207.

Buchman, et al., "Silica nanoparticles and polyethyleneimine (PEI)-mediated functionalization: a new method of PEI covalent attachment for siRNA delivery applications," Bioconjugate Chemistry, vol. 24, No. 12, 2013, pp. 2076-2087.

Choi & Lee, "Enhanced gene delivery using disulfide-crosslinked low molecular weight polyethylenimine with listeriolysin o-polyethylenimine disulfide conjugate," J. Control. Release, vol. 131, No. 1, 2008, pp. 70-76.

Gref, et al., "'Stealth' corona-core nanoparticles surface modified by polyethylene glycol (PEG): influences of the corona (PEG chain length and surface density) and of the core composition on phagocytic uptake and plasma protein adsorption," Colloids and Surface B Biointerfaces, vol. 18, No. 3-4, 2000, pp. 301-313.

Ha & Breuer, "Mitotic Kinases and p53 Signaling," Biochemistry Research International, vol. 2012, 2012, 14 pages.

Hatakeyama, et al., "Assessment of in vivo siRNA delivery in cancer mouse models," Methods Mol. Biol., vol. 1402, 2016, pp. 189-197.

Haussecker, Dirk, "The Business of RNAi Therapeutics in 2012," Mol. Ther. Nucleic. Acids, vol. 2, No. 8, 2012, 12 pgs.

He, et al., "Core-shell nanoscale coordination polymers combine chemotherapy and photodynamic therapy to potentiate checkpoint blockade cancer immunotherapy," Nature Communications, vol. 7, 2016, 12 pages.

Heo, et al., "Sequential delivery of an anticancer drug and combined immunomodulatory nanoparticles for efficient chemoimmunotherapy," Int. J. Nanomedicine, vol. 10, 2015, pp. 5981-5993.

Hong, et al., "AZD9150, a next-generation antisense oligonucleotide inhibitor of STAT3 with early evidence of clinical activity in lymphoma and lung cancer," Science Translational Medicine, vol. 7, No. 314, 2015, 13 pages.

Johnston & Grandis, "STAT3 Signaling: Anticancer Strategies and Challenges," Molecular Interventions, vol. 11, No. 1, 2011, pp. 18-26.

Kanasty, et al. "Delivery materials for siRNA therapeutics," Nat. Mater., vol. 12, No. 11, 2013, pp. 967-977.

Kim & Kim, "Bioreducible polymers for gene delivery," React. Funct. Polym., vol. 71, No. 3, 2011, pp. 344-349.

Kortylewski & Yu, "Role of Stat3 in suppressing anti-tumor immunity," Current Opinion in Immunology, vol. 20, No. 2, 2008, pp. 228-233.

Kortylewski, et al., "In vivo delivery of siRNA to immune cells by conjugation to a TLR9 agonist enhances antitumor immune responses," Nature Biotechnology, vol. 27, No. 10, 2009, pp. 925-932.

Kortylewski, et al., "Toll-like receptor 9 activation of signal transducer and activator of transcription 3 constrains its agonist-based immunotherapy," Cancer Res., vol. 69, No. 6, 2009, pp. 2497-2505.

Krieg, Arthur, "Therapeutic potential of Toll-like receptor 9 activation," Nature Reviews Drug Discovery, vol. 5, No. 6, 2006, pp. 471-484.

Lee, et al., "Controlled synthesis of PEI-coated gold nanoparticles using reductive catechol chemistry for siRNA delivery," J. Cont. Release, vol. 155, No. 1, 2011, pp. 3-10.

Lin, et al., "Intracellular cleavable poly(2-dimethylaminoethyl methacrylate) functionalized mesoporous silica nanoparticles for efficient siRNA delivery in vitro and in vivo," Nanoscale, vol. 5, No. 10, 2013, pp. 4291-4301.

Mao, et al., "Influence of Polyethylene Glycol Chain Length on the Physicochemical and Biological Properties of Poly (ethylene imine)-graft-Poly(ethylene glycol) Block Copolymer/SiRNA Polyplexes," Bioconjugate Chem., vol. 17, No. 5, 2006, pp. 1209-1218.

Meng, et al., "Use of size and a copolymer design feature to improve the biodistribution and the enhanced permeability and retention effect of doxorubicin-loaded mesoporous silica nanoparticles in a murine xenograft tumor model," ACS Nano, vol. 5, No. 5, 2014, pp. 4131-4144.

Milicic, et al., "Small Cationic DDA:TDB Liposomes as Protein Vaccine Adjuvants Obviate the Need for TLR Agonists in Inducing Cellular and Humoral Responses," PLoS One, vol. 7, No. 3, 2012, 10 pages.

Mitra, et al., "Novel epithelial cell adhesion molecule antibody conjugated polyethyleneimine-capped gold nanoparticles for enhanced and targeted small interfering RNA delivery to retinoblastoma cells," Mol. Vis., vol. 19, 2013, pp. 1029-1038.

Morry, et al., "Dermal delivery of HSP47 siRNA with NOX4-modulating mesoporous silica-based nanoparticles for treating fibrosis," Biomaterials, vol. 66, 2015, pp. 41-52.

Morry, et al., "Targeted treatment of metastatic breast cancer by PLK1 siRNA delivered by an antioxidant nanoparticle platform," Molecular Cancer Therapeutics, vol. 16, No. 4, 2017, pp. 763-772.

Neu, et al., "Bioreversibly crosslinked polyplexes of PEI and high molecular weight PEG show extended circulation times in vivo," J. Contr. Release, vol. 124, No. 1-2, 2007, pp. 69-80.

Ngamcherdtrakul, et al., "Cationic Polymer Modified Mesoporous Silica Nanoparticles for Targeted SiRNA Delivery to HER2+ Breast Cancer," Adv. Funct. Mater., vol. 25, No. 18, 2015, pp. 2646-2659.

Ngamcherdtrakul, et al., "Current development of targeted oligonucleotide-based cancer therapies: Perspective on HER2-positive breast cancer treatment," Cancer Treatment Reviews, vol. 45, 2016, pp. 19-29.

Ngamcherdtrakul, et al., "Lyophilization and stability of antibody-conjugated mesoporous silica nanoparticle with cationic polymer and PEG for siRNA delivery," Int. J. Nanomedicine, vol. 13, 2018, pp. 4015-4027.

Pan, et al., "Intradermal delivery of STAT3 siRNA to treat melanoma via dissolving microneedles," Scientific Reports, vol. 8, No. 1117, 2018, 11 pages.

Park, et al., "Clustered Magnetite Nanocrystals Cross-Linked with PEI for Efficient siRNA Delivery," Biomacromolecules, vol. 12, No. 2, 2011 pp. 457-465.

PCT Search Report and Written Opinion for Application No. PCT/US2020/041852, dated Oct. 9, 2020, 10 pages.

Pierce, et al., "In-situ tumor vaccination: Bringing the fight to the tumor," Hum. Vaccin. Immunother., vol. 11, No. 8, 2015, pp. 1901-1909.

Pradhan, et al.,"The effect of combined IL10 siRNA and CpG ODN as pathogenmimicking microparticles on Th1/Th2 cytokine balance in dendritic cells and protective immunity against B cell lymphoma," Biomaterials, vol. 35, No. 21, 2014, pp. 5491-5504.

Shao, et al., "Nanoparticle-Based Immunotherapy for Cancer," American Chemical Society, vol. 9, No. 1, 2015, pp. 16-30.

Shen, et al., "Cyclodextrin and polyethylenimine functionalized mesoporous silica nanoparticles for delivery of siRNA cancer therapeutics," Theranostics, vol. 4, No. 5, 2014, pp. 487-497.

Slowing, et al., "Mesoporous Silica Nanoparticles for Drug Delivery and Biosensing Applications," Advanced Functional Materials, vol. 17, No. 8, 2007, pp. 1225-1236.

Tang, et al., "Mesoporous silica nanoparticles: synthesis, biocompatibility and drug delivery," Adv. Mater., vol. 24, No. 12, 2012, pp. 1504-1534.

(56) References Cited

OTHER PUBLICATIONS

Tarn, et al., "Mesoporous Silica Nanoparticle Nanocarriers: Biofunctionality and Biocompatibility," Accounts of Chemical Research, vol. 46, No. 3, 2013, pp. 792-801.
Toy and Roy, "Engineering nanoparticles to overcome barriers to immunotherapy," Bioeng. and Translat. Med., vol. 1, No. 1, 2016, pp. 47-62.
Wang, et al., "In vivo hematopoietic stem cell gene therapy ameliorates murine thalassemia intermedia," Journal of Clinical Investigation, vol. 129, No. 2, 2019, pp. 598-615.
Xia, et al., "Polyethyleneimine Coating Enhances the Cellular Uptake of Mesoporous Silica Nanoparticles and Allows Safe Delivery of siRNA and DNA Constructs," ACS NANO, vol. 3, No. 10, 2009, pp. 3273-3286.
Yan, et al., "Combining Immune Checkpoint Inhibitors With Conventional Cancer Therapy," Front. Immunol., vol. 9, No. 1739, 2018, 13 pages.
Zhang, et al., "Differential Expression of Syndecan-1 Mediates Cationic Nanoparticle Toxicity in Undifferentiated versus Differentiated Normal Human Bronchial Epithelial Cells," ACS Nano, vol. 5, No. 4, 2011, pp. 2756-2769.
Zhang, et al., "Synthesis of poly(ethylene glycol) (PEG)-grafted colloidal silica particles with improved stability in aqueous solvents," J. Colloid. Interface Sci., vol. 301, No. 2, 2007, pp. 446-455.
Office Action from the European Patent Office for Application No. 16765662.8, dated Feb. 10, 2021, a counterpart foreign application of U.S. Appl. No. 15/429,971, 7 pgs.
Kortylewski, et al., "TLR agonist-Stat3 siRNA conjugates: cell-specific gene silencing and enhanced antitumor immune responses," Nature Biotechnology, vol. 27, No. 10, pp. 925-932 plus 13 pages of Supplementary Figures.

\* cited by examiner

Tumor implantation (B16F10)
250K on the local site
100K on the distant site

Intratumoral injections

Intratumoral injection in the local tumor

Local (treated) tumor

▲ Saline (n=7)
◆ CpG-NP (n=7)

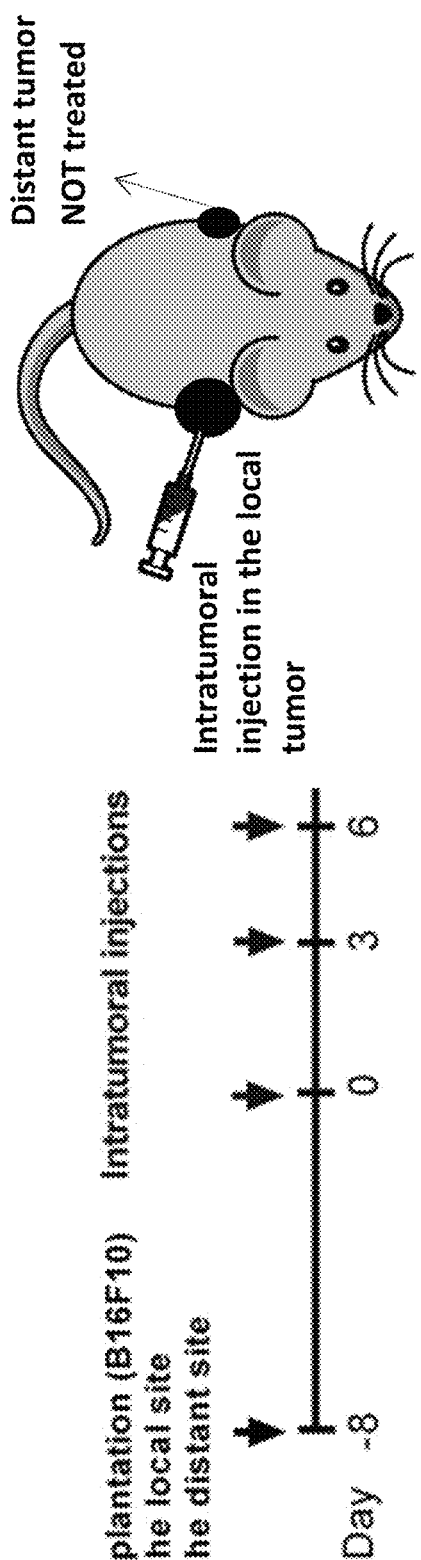
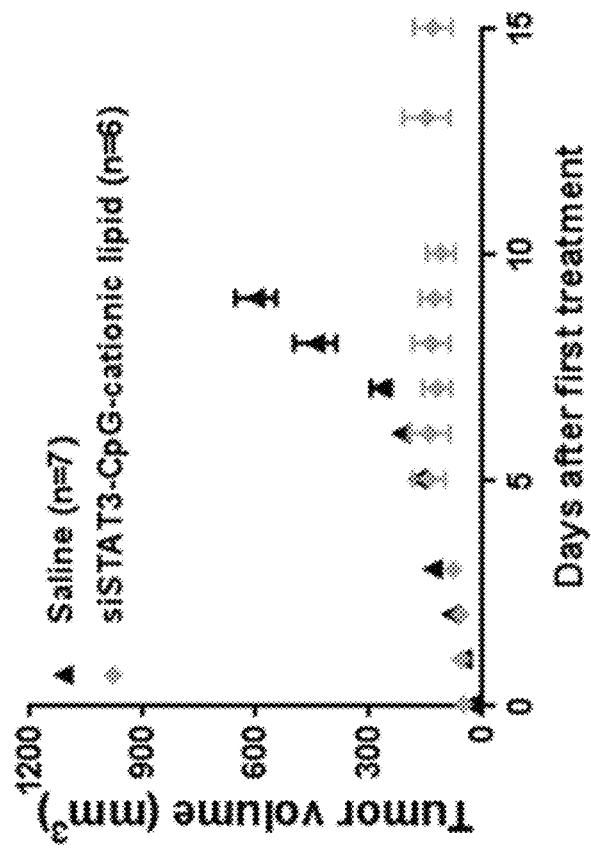
FIG. 11A
FIG. 11B

| Group | AST (U/L) | ALT (U/L) | TBIL (mg/dL) | BUN (mg/dL) | CREA (mg/dL) | CK (U/L) |
|---|---|---|---|---|---|---|
| AIRISE-02 (n=7) | 211 ± 103 | 16 ± 3 | 0.1 ± 0 | 28 ± 7 | 0.1 ± 0.04 | 595 ± 426 |
| Saline (n=7) | 192 ± 52 | 16 ± 2 | 0.1 ± 0 | 23 ± 3 | 0.1 ± 0.04 | 387 ± 163 |

| Material | Hydrodynamic size | PDI |
|---|---|---|
| (2%)siRNA-(4%)CpG-NP | 95.5 ± 1.3 | 0.14 ± 0.01 |
| (2%)siRNA-(6%)CpG-NP | 106.6 ± 0.4 | 0.15 ± 0.01 |
| (2%)siRNA-(9%)CpG-NP | 146.7 ± 1.5 | 0.22 ± 0.03 |
| (4%)siRNA-(6%)CpG-NP | 120.4 ± 1.7 | 0.17 ± 0.02 |

FIG. 29A
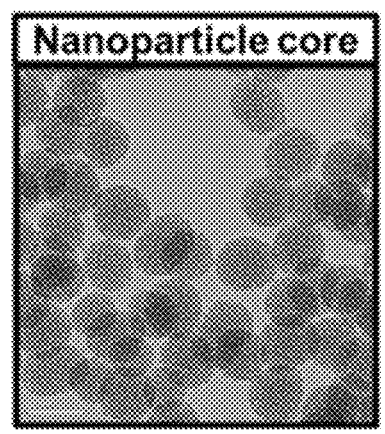
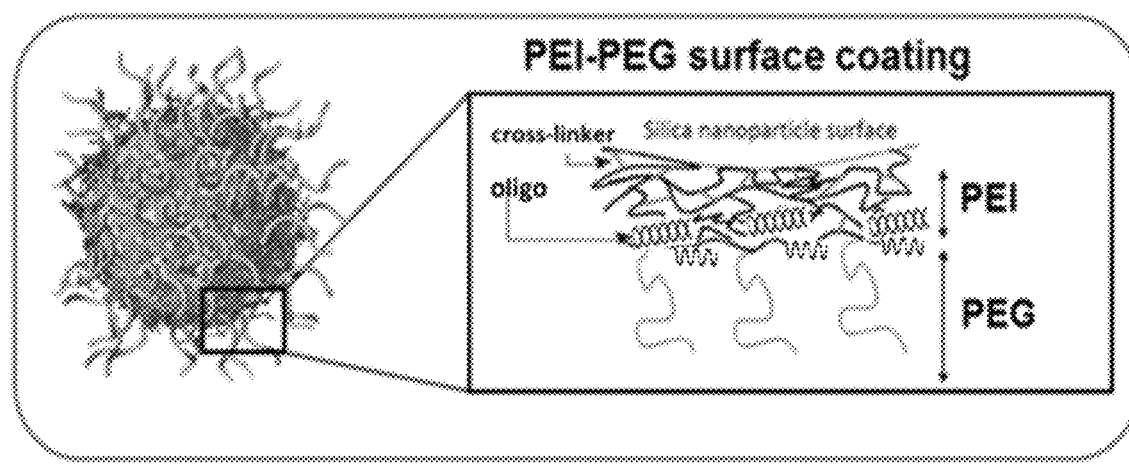
FIG. 29B
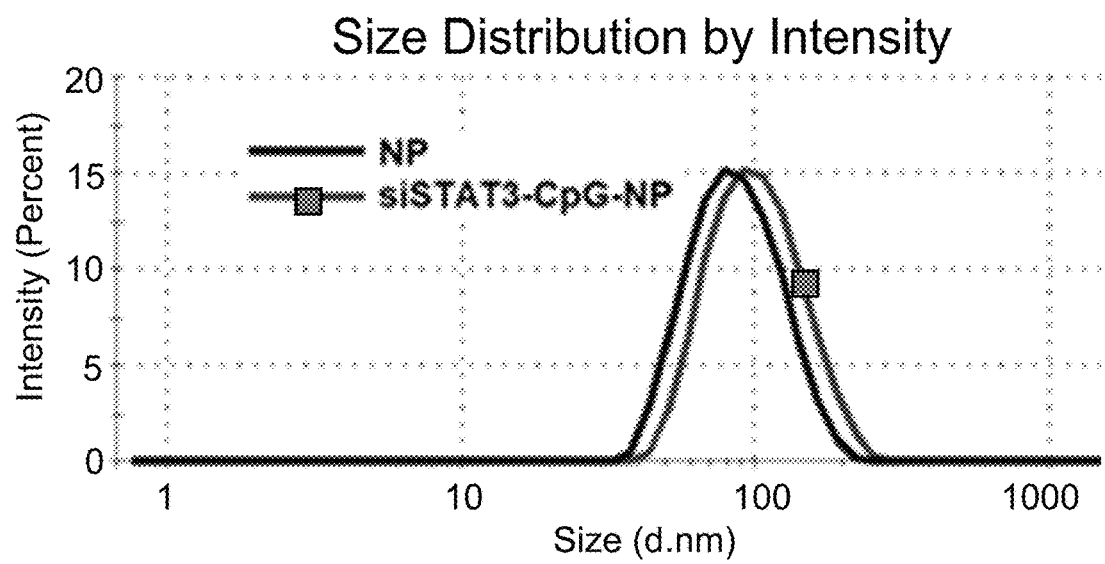
FIG. 29C

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: deoxy bases

<400> SEQUENCE: 1
ggaucuagaa cagaaaaugt t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feat
<222> LOCATION: (20)..(21)
<223> OTHER INFORMATION: deoxy bases

<400> SEQUENCE: 2
cauuuucugu ucuagaucct g                                              21

<210> SEQ ID NO 3
<211> LENGTH: 23
<212> TYPE: RNA
<213> ORGANISM: Artificial Sequence
<220> FEATURE:
<223> OTHER INFORMATION: Synthetic Construct

<400> SEQUENCE: 3
cacguuugag uccaugccca auu                                            23
```

```
<210> SEQ ID NO 4
<211> LENGTH: 23
<212> TYPE: RNA
<213> ORGANISM: Artificial Sequence
<220> FEATURE:
<223> OTHER INFORMATION: Synthetic Construct

<400> SEQUENCE: 4
uugggcaugg acucaaacgu guu                                             23

<210> SEQ ID NO 5
<211> LENGTH: 19
<212> TYPE: RNA
<213> ORGANISM: Artificial Sequence
<220> FEATURE:
<223> OTHER INFORMATION: Synthetic Construct

<400> SEQUENCE: 5
ugguuuacau gucgacuaa                                                  19

<210> SEQ ID NO 6
<211> LENGTH: 19
<212> TYPE: RNA
<213> ORGANISM: Artificial Sequence
<220> FEATURE:
<223> OTHER INFORMATION: Synthetic Construct

<400> SEQUENCE: 6
uuagucgaca uguaaacca                                                  19

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
tccatgacgt tcctgacgtt                                                 20

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
tcgtcgtttt gtcgttttgt cgtt                                            24
```

IMMUNOTHERAPEUTIC CONSTRUCTS AND METHODS OF THEIR USE

CROSS-REFERENCE TO RELATED APPLICATIONS

This is a continuation of International Application No. PCT/US2020/041844, filed Jul. 13, 2020, which in turn claims priority of the earlier filing date of U.S. Provisional Application No. 62/873,762, filed on Jul. 12, 2019. Each of these earlier filed applications is incorporated by reference herein in its entirety.

STATEMENT REGARDING FEDERALLY SPONSORED RESEARCH OR DEVELOPMENT

This invention was made with government support under grant R44CA217534 and R43TR001906 awarded by the National Institutes of Health. The government has certain rights in the invention.

FIELD OF THE INVENTION

The current disclosure relates to compositions and methods for treatment and prevention of cancer and other diseases and conditions. The compositions include immunotherapeutic constructs that include a delivery system (such as a particle) containing at least one therapeutically active agent (which causes tumor antigen release and/or modulates an immunosuppressive tumor microenvironment) and at least one adjuvant (or immunostimulant), creating adaptive immunity by utilizing antigens in subjects' own precancer or cancer cells.

BACKGROUND OF THE INVENTION

Immune checkpoint inhibitors, such as inhibitors for PD-L1, PD-1, CTLA-4, etc., have shown promising outcome in clinics, gaining fast track FDA approval for many cancer types. However, the treatment works only in a subset of cancer patients (~10-40%). Lack of response is typically due to absence of pre-existing antitumor immunity (e.g., CD8+ T cells) strengthening the need for vaccines to boost the number of anti-tumor T cells in the body.

Classical cancer vaccines utilize an immune-stimulator (called adjuvant) and tumor proteins (called antigens). Ideally, neoantigens that exists exclusively on cancer cells should be used. However, these neoantigens vary widely across tumor types and patients, making it difficult and costly to develop personalized vaccines for each patient. To circumvent the need to identify these antigens, radiation, chemotherapy, and engineered viruses such as talimogene laherparepvec (T-VEC) have been used to kill tumors and release the antigens to trigger adaptive immune response in situ. These approaches however create an undesirable environment in the immunosuppressive tumor microenvironment (e.g., by increasing chemical stressors called oxidants, or promoting immunosuppressive pathways) that lead to low antitumor T cell count or ineffective antitumor T cells. In addition, in situ tumor vaccination strategies have suffered from the immunosuppressive microenvironment of tumors and the inability to retain vaccine components for effective delivery to target cells (e.g., antigen presenting cells).

SUMMARY OF THE INVENTION

To overcome the aforementioned shortcomings, we developed a new class of immunotherapeutic that exploits the in situ tumor vaccination strategy. In situ tumor vaccination is a strategy in which tumors are locally killed and release tumor antigens in the presence of immunostimulation, which together prime the systemic adaptive immunity against tumors. In certain cases, tumor antigens already present in the tumor microenvironment (TME) are utilized. This strategy has great promise because it circumvents the need to pre-identify tumor (neo)antigens as in conventional cancer vaccine development. This is also a personalized therapy since a unique set of tumor antigens is released and primes specific immunity for each patient.

Described herein are engineered particles for co-delivery of adjuvants and compounds that are capable of inducing antigen release and/or modulating immunosuppressive environment to boost the CD8+ T cell repertoire and induce systemic anti-tumor immunotherapy effects. This technology can be referred to as AIRISE, which stands for Augmenting Immune Response and Inhibiting Suppressive Environment of Tumors.

Described herein is a new class of immunotherapeutics (generally, immunotherapeutic constructs) based on engineered particles that enable co-delivery of adjuvant(s) and therapeutically active agent(s) that are capable of inducing antigen release (e.g., by killing cancer cells) and/or modulating an immunosuppressive environment (such as a tumor microenvironment, TME). These immunotherapeutic constructs may also use antigens already present in the TME. The immunotherapeutic constructs boost the CD8+ T cell repertoire and induce systemic anti-tumor immunotherapy effects, without any need to know which antigen(s) are associated with the cancer being treated. Although cellular immunity is extensively described herein, humoral immunity (antibody generation) also plays a role and follows the same concept.

Examples of therapeutically active agents (e.g., siRNA, miRNA, antisense oligonucleotide, mRNA, shRNA, DNA, other oligonucleotides and polynucleotides, small molecule inhibitors, chemotherapeutics, antibodies, etc.) delivered to cancer cells by the provided engineered immunotherapeutic constructs will kill cancer cells, releasing tumor antigens, and/or manipulate the immunosuppressive tumor microenvironment, while the co-delivered adjuvants (e.g., CpG, R848, poly I:C, etc.) prime and activate adaptive immune cells against the tumor antigens. The activated effector cells can recognize and attack tumors at any sites in the body (including sites remote from localized delivery of the immunotherapeutic constructs) as well as reducing or even preventing the spread or the development of new tumors harboring one or more of the same tumor antigens as the treated tumors. This phenomenon is sometimes referred to as the abscopal effect. Death of cancer cells further amplifies the adaptive immunity loop with long-lasting effects. Memory adaptive immunity will also be established for continuous antitumor immune surveillance.

The immunotherapeutic constructs can be administered locally, intratumorally, intranasally, intraperitoneally, intracerebrospinally, subcutaneously, intra-articularly, intrasynovially, intrathecally, orally, topically, dermally, intravenously, or by inhalation, e.g., to readily accessible tumors such as melanoma, head and neck cancer, breast cancer, colon cancer, ovarian cancer, bladder cancer, and lymphoma; or systemically for other cancers such as lung cancer, liver cancer, pancreatic cancer, prostate cancer, brain cancer, kidney cancer, blood cancer, and metastatic cancers.

Engineered immunotherapeutic constructs can have a diameter in the nanometers or micrometer range, and can be made of any materials (e.g., lipid, inorganic materials, polymers, and their combinations) capable of loading the therapeutic agents/adjuvant cargos, delivering them to the target sites (cancer cells, immune cells, extracellular matrices, etc.), and allowing them to have the desired functions.

Optionally, immunotherapeutic constructs also contain one or more homing agents (antibodies, aptamers, ligands, peptides, etc.) that enable them to be preferentially delivered to and/or taken up by target cancer cells and/or various immune cell types (e.g., dendritic cells (DCs), macrophages, monocytes, T cells).

The herein provided immunotherapeutic constructs may be used alone or in combination with standard therapeutics, including, but not limited to, immune checkpoint inhibitors, chemotherapy, surgery, targeted therapies, and radiation therapy. Alternatively, checkpoint inhibitors (siRNA, inhibitors, or antibody against for PD-L1/PD-1, CTLA-4, etc.), other targeted therapeutics (e.g., small molecule inhibitors or antibodies targeting other oncoproteins, or medical radioactive isotopes) can be loaded directly on/in the immunotherapeutic constructs as a therapeutically active agent.

For local delivery, the immunotherapeutic constructs optionally can be formulated into topical or microneedle formulations.

In particular embodiments, there is provided an immunotherapeutic construct including: a delivery system including at least one therapeutic agent that causes tumor antigen release and/or modulates an immunosuppressive tumor microenvironment; and at least one adjuvant. The immunotherapeutic construct may not include a tumor-specific antigen or ovalbumin. In another embodiment, the immunotherapeutic construct does not include a protein other than the one therapeutic agent or the at least one adjuvant, if either is a protein. The therapeutic agent and adjuvant may be loaded into, attached to the surface of, coupled to, enclosed within, or contained within the delivery system. In particular embodiments of the provided immunotherapeutic construct, the delivery system are nanoparticles with a hydrodynamic size of 5 nm to 999 nm (e.g., about 80 nm to about 200 nm, or about 90 nm to about 130 nm), as measured in an aqueous medium (such as PBS, Tris-buffer, or water). In yet other examples, the immunotherapeutic constructs are microparticles with a hydrodynamic size of 1 micron to 1000 micron. In some embodiments, the delivery system has a size of about 5 nm to about 200 nm, about 5 nm to about 90 nm, about 5 nm to about 20 nm, about 30 nm to about 100 nm, about 30 nm to about 80 nm, about 30 nm to about 60 nm, about 40 nm to about 80 nm, about 70 nm to about 90 nm, or about 5 nm, about 10 nm, about 20 nm, about 30 nm, about 40 nm, about 50 nm, about 60 nm, about 70 nm, about 80 nm, about 90 nm, or about 100 nm.

In various embodiments of immunotherapeutic constructs, the therapeutic agent includes an oligonucleotide (e.g., a siRNA, a miRNA, an antisense oligonucleotide, a mRNA, a DNA, a shRNA, or a sgRNA (CRISPR-cas9 element)), a polynucleotide, a peptide, a protein, a chemotherapy drug, a toxin, an antioxidant, a small molecule inhibitor, an antibody, or a radio-therapeutic agent.

In examples of the immunotherapeutic construct, the adjuvant compound has immunostimulatory activity. By way of example, adjuvant compounds may include one or more of a TLR-binding DNA substituent, such as a CpG oligonucleotide (e.g., ISS 1018; Amplivax; CpG ODN 7909, CpG ODN 1826, CpG ODN D19, CpG ODN 1585, CpG ODN 2216, CpG ODN 2336, ODN 1668, ODN 1826, ODN 2006, ODN 2007, ODN 2395, ODN M362, or SD-101); a DNA TLR agonist that contains CpG sequences (e.g., dSLIM); a non-CpG DNA TLR agonist (e.g., EnanDIM); a RNA TLR agonist (e.g., Poly I:C or Poly-ICLC); an aluminum salt (e.g., aluminum hydroxide, aluminum phosphate, aluminum chloride, or aluminum potassium sulfate); an anti-CD40 antibodies (e.g., CP-870,893); a cytokine, such as a granulocyte-macrophage colony-stimulating factor (GM-CSF); a cationic peptide-conjugated CpG oligonucleotide (e.g., IC30, IC31); a small molecule TLR agonist (e.g., imiquimod, resiquimod, gardiquimod, or 3M-052); a fusion protein (e.g., ImuFact IMP321 and ONTAK); an oil/surfactant-based adjuvant such as MF59, Montanide IMS 1312, Montanide ISA 206, Montanide ISA 50V, and Montanide ISA-51; QS21 stimulon (Aquila Biotech, Worcester, Mass., USA), which is derived from saponin; a mycobacterial extract or synthetic bacterial cell wall mimic, such as a lipopolysaccharide (e.g., monophosphoryl lipid A, OM-174, OM-197-MP-EC, or Pam3Cys); a xanthenone derivative (e.g., vadmezan); a mixture thereof (e.g., AS-15); or a proprietary adjuvant such as Ribi's Detox, Quil, or Superfos.

Also provided are methods of using the immunotherapeutic constructs described herein, for instance in methods of treating or preventing cancer or another hyperproliferative disease. As an example, for melanoma, an immunotherapeutic construct can be used as a prophylactic vaccine in patients (including and especially those that are genetically predisposed) with a large number of atypical nevi or other seemingly benign moles. As another example, the immunotherapeutic construct can be given to accessible tumors/lesions via intratumoral/intralesional injection prior to surgical removal (i.e. neoadjuvant setting) to lessen the chance of recurrence and/or recruit immune system to kill any detectable or undetectable metastases. As another example, the immunotherapeutic construct can be given to a tumor via intratumoral injection even though the tumor is unresectable. This will activate and recruit the immune system to attack both the treated tumor and untreated tumors elsewhere in the body. As another example, the immunotherapeutic construct can be given systemically to initiate anti-tumor adaptive immune response. In certain embodiments, the immunotherapeutic construct may be given to the area around the tumor (peritumoral) or the area remaining after tumor removal (adjuvant setting). As another example, the immunotherapeutic construct can be given systemically, which will develop adaptive immunity against cancer anywhere in the body. In certain embodiment, the immunotherapeutic construct may be administered directly into lymph nodes (with or without detectable tumors).

Another embodiment is a method of treating a cell obtained from a subject exhibiting symptoms of cancer, which method includes contacting the cell with a therapeutically effective amount of an immunotherapeutic construct of any one of the described embodiments, or a composition including an immunotherapeutic construct. In examples of this embodiment, the cell obtained from the subject is a cancer cell. In other embodiments, the cell is not a cancer cell; for instance, in some instances the non-cancer (e.g., normal) cell is an immunology/immune cell. In examples of the methods of treating a cell, the method further includes administering at least one treated cell back to the subject.

Also provided are method embodiments that combine administration of an immunotherapeutic construct along with at least one other treatment, for instance a treatment for cancer or another hyperproliferative disease or condition.

Administering an immunotherapeutic construct in any of the described method embodiments may include one or more of: injection directly into a tumor in the subject; systemic injection in the subject; topical application to the subject; inhalation by the subject; hepatic arterial infusion to the subject; convection-enhanced delivery to the subject; or microneedle application to the subject.

In examples of any of the provided method embodiments, the subject (being treated, to which a construct or composition is being administered, or from which a cell is obtained) is a mammal; for instance, in certain embodiments the mammal is a human.

It is specifically contemplated herein that any of the provided immunotherapeutic construct embodiments, and embodiments of methods of using such constructs, include examples in which the immunotherapeutic construct does not include a tumor-specific antigen or ovalbumin.

BRIEF DESCRIPTION OF THE DRAWINGS

FIGS. 11A-11D. CpG and siSTAT3 delivered with cationic lipid particles (DharmaFECT®) yields in situ vaccination effect. C57/BL6 mice bearing B16F10 tumors were established and treated as in FIG. 11A. The therapeutic construct reduced treated tumors (FIG. 11B) and distant tumors (FIG. 11C), as well as prolonged survival of mice (FIG. 11D). Dose (per each injection): 20 μg CpG; 4 μg siSTAT3. The therapeutic construct has the average size of 1068 nm (1.1 micron) as measured by DLS.

FIG. 14B shows the level of EGFR expression of these cell lines as measured by a flow cytometry. Likewise, FIG. 14C shows that HER2 antibody (trastuzumab) conjugated nanoparticles (T-siSCR-NP) were also preferentially taken up by breast cancer cells overexpressing HER2 (BT474, SKBR3) over MCF7 (with low HER2 expression, as shown by Western Blot analysis (Inset of (FIG. 14C)). The preferential effect was not observed with rituximab (CD20 antibody) conjugated nanoparticles (R-siSCR-T). siSCR denoted scrambled siRNA.

FIGS. 29A-29C. AIRISE-02. (FIG. 29A) TEM image of mesoporous silica nanoparticle core, (FIG. 29B) Schematic of AIRISE-02 comprising a mesoporous silica nanoparticle coated with PEI, which is cross-linked as described prior (Ngamcherdtrakul et al., *Advanced Functional Materials*, 25(18):2646-2659, 2015), conjugated with PEG, resulting in a nanoparticle construct (NP). NP was loaded with siSTAT3 and CpG by electrostatic interaction by 10-40 min mixing in PBS. (FIG. 29C) Hydrodynamic size of AIRISE-02 ((2%) siSTAT3-(6%)CpG-NP).

REFERENCE TO SEQUENCE LISTING

Figure 1:
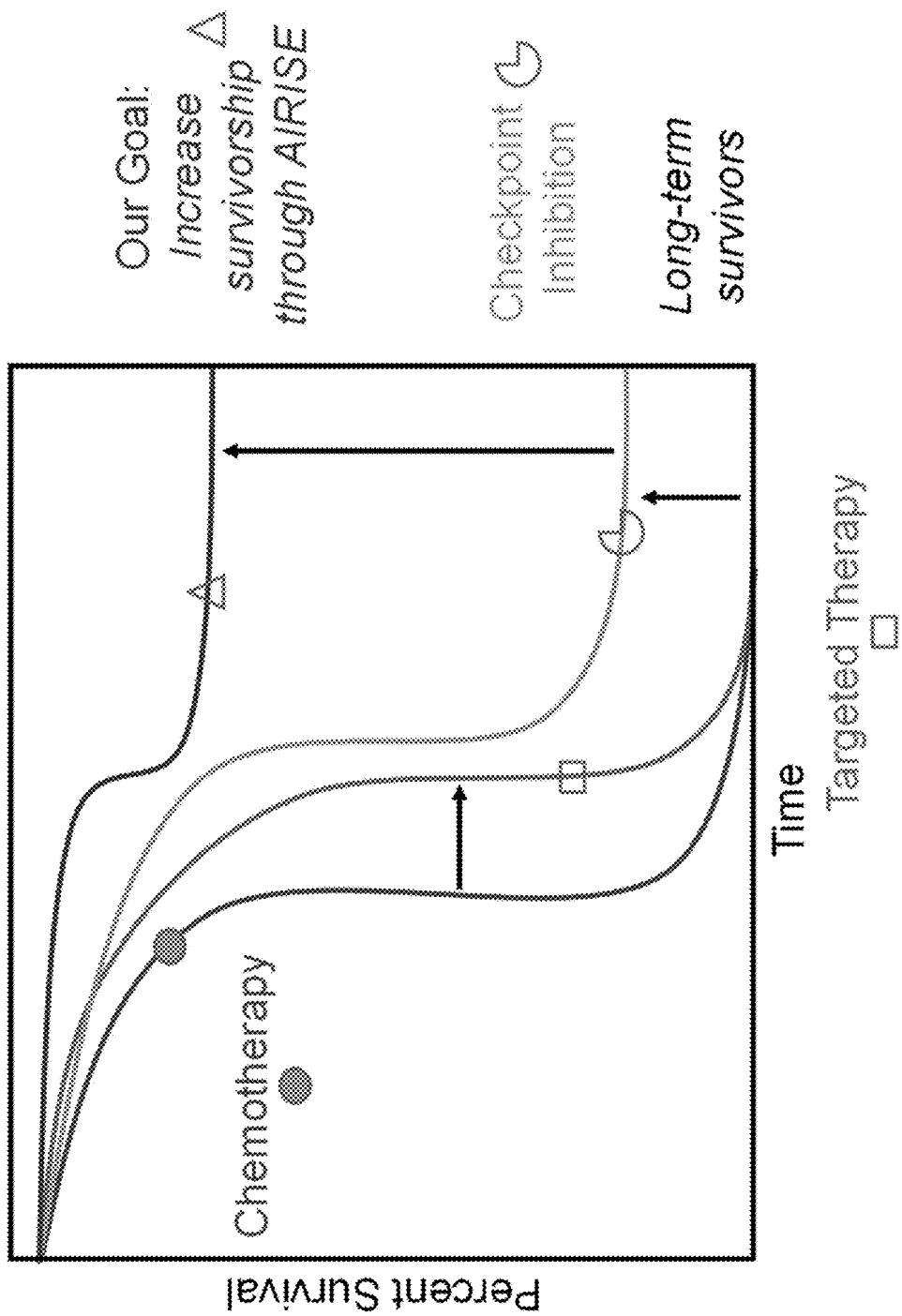
FIG. 1. Cancer treatment. Targeted therapy has improved cancer prognosis significantly over non-specific toxic chemotherapy. However, the effect is not sustained. Immune checkpoint inhibitors (ICIs) unleash the body's own immune system to attack cancer, potentially resulting in cure. However, only a small subset of patients respond to this treatment. Our goal is to develop a novel immunotherapeutic construct (Augmenting Immune Response and Inhibiting Suppressive Environment of tumors—AIRISE) that manipulate the tumor microenvironment (TME) to boost anti-tumor T cell repertoires, which will increase the cure rate of cancer patients treated with ICIs.

The nucleic acid sequences described herein are shown using standard letter abbreviations for nucleotide bases, as defined in 37 C.F.R. § 1.822. Only one strand of each nucleic acid sequence is shown, but the complementary strand is understood as included in embodiments where it would be appropriate. A computer readable text file, entitled "51127-004002_Sequence Listing_08.21.20_ST25.txt" created on or about Aug. 21, 2020, with a file size of 2 KB, contains the sequence listing for this application and is hereby incorporated by reference in its entirety.

SEQ ID NO: 1 is a representative sense sequence of an siRNA specific for STAT3 (siSTAT3): 5' GGAUCUA-GAACAGAAAAUGdTdT 3' (the last two positions of which are deoxy bases).

SEQ ID NO: 2 is a representative antisense sequence of an siRNA specific for STAT3 (siSTAT3): 5' CAUUUUCU-GUUCUAGAUCCdTdG 3' (the last two positions of which are deoxy bases).

SEQ ID NO: 3 is a representative sense sequence of an siRNA specific for HER2 (siHER2): 5' CACGUUUGAGU-CCAUGCCCAAUU 3'.

SEQ ID NO: 4 is a representative antisense sequence of an siRNA specific for HER2 (siHER2): 5' UUGGG-CAUGGACUCAAACGUGUU 3'.

SEQ ID NO: 5 is a representative sense sequence of an siRNA specific for SCR (siSCR): 5' UGGUUUACAUGU-CGACUAA 3'.

SEQ ID NO: 6 is a representative antisense sequence of an siRNA specific for SCR (siSCR): 5' UUAGUCGACAU-GUAAACCA 3'.

SEQ ID NO: 7 is the sequence of CpG ODN 1826, which was used throughout the examples (mouse system): 5'-TC-CATGACGTTCCTGACGTT-3'. This ODN contains a full phosphorothioate backbone and is nuclease resistant.

SEQ ID NO: 8 is the sequence of CpG ODN 2006/7909, which was used in examples with monkey and human system: 5'-TCGTCGTTTTGTCGTTTTGTCGTT-3'. This ODN contains a full phosphorothioate backbone and is nuclease resistant

DETAILED DESCRIPTION

The herein described immunotherapeutic approach called AIRISE (Augmenting Immune Response and Inhibiting Suppressive Environment of Tumors) for cancer treatment (FIGS. 1 and 2) utilizes patients' own tumors as a depot for a personalized set of tumor antigens (in situ tumor vaccination). The provided immunotherapeutic constructs carry at least one adjuvant (e.g., a CpG oligonucleotide) and one or more therapeutic agents/compounds (e.g., a siRNA, an antisense, oligonucleotide, a drug, a small molecule, an antibody, etc.) that cause antigen release and/or modulate immunosuppressive tumor microenvironment. Specific examples of such therapeutic agents are docetaxel and siRNA against STAT3.

Upon administration of a provided immunotherapeutic constructs at tumor site (for instance, through intratumoral injection or tumor homing via systemic delivery), tumor antigen(s) are released in the presence of immunostimulation (provided by the supplied adjuvant(s)). This antigen release and immunostimulation together initiate and support antigen-specific adaptive immunity. Tumor antigens can be taken up by existing antigen-presenting cells (APCs), which present the antigen to naïve T cells. T cells (against those tumor antigens) are thereby primed and activated into effector T cells (either in lymph nodes or in tumor site) and proliferate throughout the body, thus providing increased and improved immune response to the treated tumor as well as to other tumors remote from the initial administration (e.g., metastatic sites). The efficacy in tumors remote from the initial administration site is also known in the field as an abscopal effect.

Figure 2:
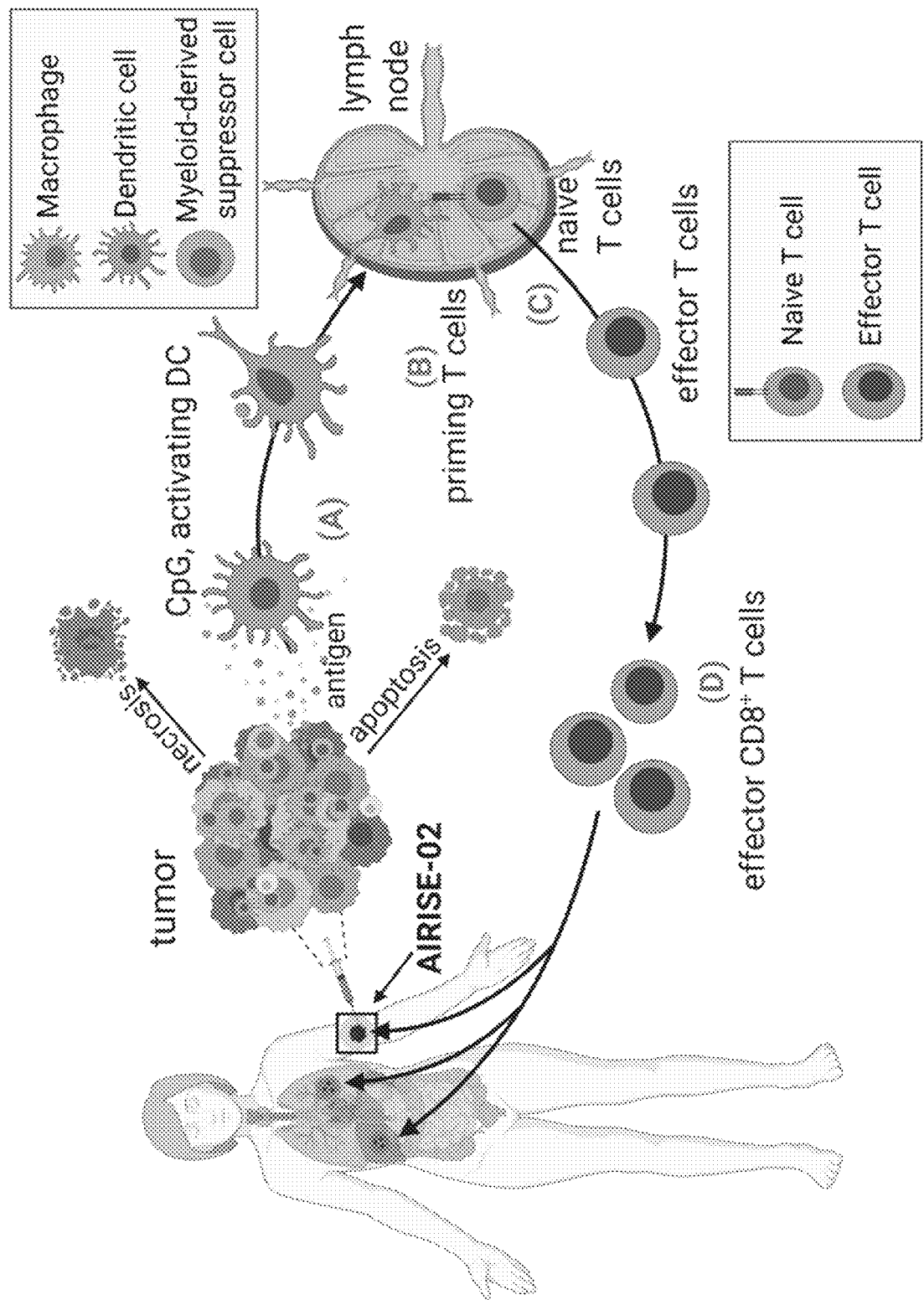
FIG. 2. In situ tumor vaccination mechanism of our novel immunotherapeutic constructs. Only one of the tumors (e.g., a melanoma or breast tumor) is intratumorally injected with the immunotherapeutic constructs AIRISE. In one example, i.e., AIRISE-01 or CpG/DTX-NP, docetaxel (DTX), a chemotherapeutic drug, which also has adjuvant property, will kill local cancer cells to release tumor antigens, and CpG oligonucleotide (adjuvant) will activate local antigen-presenting cells (APCs) (primarily dendritic (DCs)). In another example, i.e., AIRISE-02 or siSTAT3-CpG-NP, siSTAT3 can kill some cancer cells, while knocking down STAT3 reduces immunosuppressive tumor microenvironment that prevents the priming, activation, and function of anti-tumor adaptive immune response. Tumor antigens already in the tumor microenvironment (TME, including cancer, immune cells, etc.), or released by our treatment will be taken up by the AIRISE-activated APCs in the tumor and tumor-draining lymph node(s). APCs then (cross) present these antigens to prime tumor antigen-specific T cells. These activated cytotoxic (effector CD8+) T cells will proliferate and enter systemic circulation. They will home specifically to tumors having some of the same antigens as the treated tumor wherever they are located in the body (e.g., homing back to both the treated tumor and untreated metastatic tumors). Death of more cancer cells by cytotoxic T cells further releases more tumor antigens, amplifying the proliferation of effector (already primed) T cells in a positive feedback loop. Anti-tumor humoral immunity is also activated following the same concept. The mesoporous silica nanoparticles in these examples also have antioxidant properties (Morry, *J. Biomaterials*, 66:41-52, 2015), which can also modulate immunosuppressive TME further, inhibiting pro-tumoral activities. This vaccination induced locally at the tumor site generates whole-body systemic anti-tumor immune response.

These anti-tumor T cells trained to recognize the specific tumor antigens will control tumors both at injected sites and elsewhere in the body (see FIG. 2). The cargo combination can be applied on any type of micro/nanoparticles—that is, embodiments of the immunotherapeutic constructs and methods of their use are delivery vehicle agnostic. Specific example delivery vehicles are described herein.

The invention provides in situ tumor vaccination effect(s) using the herein-described immunotherapy, exemplified with immunotherapeutic constructs loaded with CpG and siSTAT3 (siSTAT3-CpG-NP), or with CpG and docetaxel (CpG/DTX-NP). For these two exemplary therapeutically active agents, docetaxel (DTX) will kill local cancer cells to release tumor antigens, and CpG will activate local antigen-presenting cells (APCs, primarily DCs); while siSTAT3 will kill some cancer cells, its main role is to reduce immunosuppressive tumor microenvironment (TME) that prevents priming and action of anti-tumor adaptive immune response. It should be noted that siSTAT3-CpG-NP is designed to be taken up by both cancer and APCs. While it may have some killing effect in some cancer cells, it will not kill, but rather activate APCs by knocking down STAT3. Tumor antigens (already in the TME, or released by the provided treatment) are taken up by CpG-activated or AIRISE-activated APCs in the tumor and tumor-draining lymph node. APCs then (cross) present these antigens to prime tumor antigen-specific T cells. These activated cytotoxic (effector) T cells will proliferate and enter systemic circulation. They will home specifically to tumors having some of the same antigens as the treated tumor wherever they are located in the body (e.g., homing back to both treated and distant (untreated) tumors). Death of more cancer cells by cytotoxic T cells further release more tumor antigens, amplifying the proliferation of effector (already primed) T cells in a positive feedback loop. In certain embodiments, antioxidant mesoporous silica nanoparticle (MSNP) can modulate local immunosuppressive TME further, inhibiting pro-tumoral activities. This vaccination induced locally at the tumor site generates whole-body systemic anti-tumor immunity.

In certain embodiments, the delivery vehicle includes a MSNP core (e.g., ~50 nm) for drug loading, coated with a bioreducible cross-linked cationic polymer, e.g., polyethyleneimine (PEI), for oligo loading and endosomal escape; and a stabilizer, e.g., polyethylene glycol (PEG), which prevents nanoparticle aggregation, protects oligo cargos from degradation by blood enzymes (Ngamcherdtrakul et al., *Advanced Functional Materials*, 25(18):2646-2659, 2015), and shields the charge of PEI, enhancing safety. Oligo (siRNA and/or CpG) is loaded last on the construct with a few minutes (e.g., 5 minutes) mixing in PBS at room temperature; it electrostatically binds to PEI in an oligo sequence-independent manner and is protected under the PEG layer from enzymatic degradation (Ngamcherdtrakul et al., *Advanced Functional Materials*, 25(18):2646-2659, 2015). The resulting nanoparticle (NP) was highly optimized for siRNA delivery efficacy in terms of MSNP sizes, PEI and PEG molecular weights and compositions, PEI crosslinking conditions (to enhance buffering capacity and lower charge), oligo and (optionally) antibody loadings (Ngamcherdtrakul et al., *Advanced Functional Materials*, 25(18):2646-2659, 2015). This embodiment of the siRNA-NP has a rigid MSNP core size (by TEM) of 50 nm and hydrodynamic size (NP with polymer coatings) of 100 nm with a narrow size distribution. It includes 13.5 wt. % PEI, 18.2 wt. % PEG, and can load 2-4 wt. % siRNA or up to 10 wt. % of CpG oligo. Drug (e.g., taxane) can be loaded in the MSNP core or on the polymers at 0.5-3 wt. %. All values in this paragraph are by weight of the nanoconstruct. See also U.S. Patent Application Publication No. 2017/0172923.

In a first specific embodiment, an immunotherapeutic construct including: a delivery system; at least one therapeutic agent, e.g., loaded into, attached to the surface of, coupled to, enclosed within, or contained within the delivery system, where therapeutic agent causes tumor antigen release and/or modulates an immunosuppressive tumor microenvironment; and at least one adjuvant compound, e.g., attached to the surface of, coupled to, enclosed within, or contained within the delivery system is provided.

In examples of this embodiment, the delivery system includes (or, in other embodiments, is) a liposome, a lipid-based particle, a polymeric particle, an inorganic particle, an inorganic particle coated with polymer or lipid, or a hybrid thereof.

In various examples of the immunotherapeutic construct, the delivery vehicle is an inorganic particle and includes one or more of mesoporous silica, gold, aluminum, calcium phosphate, iron oxide, or an antioxidant particle (such as cerium oxide).

In yet more examples of the immunotherapeutic construct, the delivery vehicle includes one or more of fullerenes, endohedral metallofullerenes, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, silicon, silica and polymer micro- and nano-spheres, silica-shells, biodegradable PLGA micro- and nano-spheres, gold particles, cerium oxide particles, zinc oxide particles, silver particles, aluminum particles, carbon particles, iron particles, iron oxide particles, adjuvant particles (e.g., virosomes or other virus-like particles), and/or modified micelles. Optionally, the delivery vehicle includes a polymer; in specific examples, the polymeric particles includes one or more of PLGA, PLL, polyarginine, PEG, PEI, or chitosan.

It is contemplated that in any of the provided immunotherapeutic construct embodiments, examples are nanoparticles with a hydrodynamic size of 5 nm to 999 nm (e.g., about 80 nm to about 200 nm, or about 90 nm to about 150 nm), as measured in an aqueous medium (such as PBS, Tris-buffer, or water). In some embodiments, the immunotherapeutic constructs have a hydrodynamic size of less than 150 nm, as measured in an aqueous medium (such as PBS, Tris-buffer, or water). In yet other examples, the immunotherapeutic constructs are microparticles with a hydrodynamic size of 1 micron to 1000 microns (e.g., 1 micron to 50 microns), as measured in an aqueous medium (such as PBS, Tris-buffer, or water).

In various embodiments of the described immunotherapeutic constructs, the therapeutic agent includes a siRNA, a miRNA, an antisense oligonucleotide, a mRNA, a DNA, a sgRNA (CRISPR-cas9 element), other oligonucleotide, other polynucleotide, a peptide, a protein, a chemotherapy drug, a toxin, an antioxidant, a small molecule inhibitor, an antibody, or a radio-therapeutic agent. In specific examples, the therapeutic agent inhibits expression or an activity of STAT3, CD39, CD73, TGF-$\beta$, PD-L1, PD1, CTLA4, MIF, PLK1, HIF, NOX1-4, HER2, EGFR, BCL2, AKT1, HIF1-alpha, NOX1-4, AR, MYC, or MTDH.

In yet more embodiments of the immunotherapeutic construct, the therapeutic agent is an anti-cancer agent including one or more of an antibiotic (e.g., docetaxel, doxorubicin, or mitoxantrone) a plant alkaloid (e.g., cabazitaxel), a PLK1 inhibitor, a mitotic kinase inhibitor, an immune checkpoint inhibitor (such as an antibody against PD-L1, PD1, or CTLA4), a platinum based chemotherapeutic agent, a small molecule HER2 inhibitor, or a HER2-specific antibody. Examples of mitotic kinase inhibitors include, but not limited to, inhibitors of at least one of a polo-like kinase (PLK), an Aurora kinase, cyclin-dependent kinase (CDK)1, CDK2, HASPIN, monopolar spindle 1 kinase (Mps1), or a NimA-related kinase (NEK). In some embodiments, the mitotic kinase inhibitor includes one or more of GSK461364, B12536, Tak960, NMS-P937, B16727 (volasertib), Chk 1 Kinase Inhibitor LY2603618, AU14022, YK-4-279, or PMN.

In examples of any embodiments of the immunotherapeutic construct, the adjuvant compound has immunostimulatory activity. By way of example, adjuvant compounds may include one or more of a CpG oligonucleotide, a DNA TLR agonist containing a CpG sequence, a non-CpG DNA TLR agonist, an RNA TLR agonist, an aluminum salt, an anti-CD40 antibody, a fusion protein, a cytokine, a small molecule TLR agonist, an oil- or surfactant-based adjuvant, a lipopolysaccharide, a plant extract, or a derivative thereof. In specific examples, the adjuvant compound includes a CpG oligonucleotide, imiquimod, resiquimod, gardiquimod, poly IC, poly ICLC, dSLIM, or EnanDIM.

It is specifically contemplated herein that any of the provided immunotherapeutic construct embodiments may not include a tumor-specific antigen or ovalbumin.

Yet another provided embodiment is a composition including: at least one immunotherapeutic construct as provided herein; and at least one pharmaceutically acceptable carrier, excipient, diluent, or mixture thereof.

Also provided are methods of using the immunotherapeutic constructs described herein, for instance methods of treating or preventing cancer or another hyperproliferative disease.

One provided method of treating cancer includes administering to a subject with cancer an effective amount of an immunotherapeutic construct of any one of the described embodiments, or a composition including an immunotherapeutic construct, to reduce one or more symptoms of the cancer.

Another provided method embodiment is a method of treating a cell exhibiting symptoms of cancer, which method includes contacting the cell with a therapeutically effective amount of an immunotherapeutic construct of any one of the described embodiments, or a composition including an immunotherapeutic construct.

Another provided method embodiment is a method of treating a cell obtained from a subject exhibiting symptoms of cancer, which method includes contacting the cell with a therapeutically effective amount of an immunotherapeutic construct of any one of the described embodiments, or a composition including an immunotherapeutic construct. In examples of this embodiment, the cell obtained from the subject is a cancer cell. In other embodiments, the cell is not a cancer cell; for instance, in some instances the non-cancer (e.g., normal) cell is an immunology cell. In examples of the methods of treating a cell, the method further includes administering at least one treated cell back to the subject.

Another provided embodiment is a method of treating a subject diagnosed as having a hyperproliferative disease or condition or having a high-risk of developing such disease or condition, which method involves administering to the subject an effective amount of a composition that includes at least one immunotherapeutic construct as described herein. By way of example, it is contemplated in various embodiments that the hyperproliferative disease or condition includes one or more of cancer, pre-cancer, or cancer metastasis. For instance, the hyperproliferative disease in some cases includes one or more of melanoma, lung cancer, breast cancer, pancreatic cancer, brain cancer, prostate cancer, head and neck cancer, kidney cancer, colorectal cancer, lymphoma, colon cancer, or liver cancer.

Also provided are method embodiments that combine administration of an immunotherapeutic construct along with at least one other treatment, for instance a treatment for cancer or another hyperproliferative disease or condition. In a first example of such a combination method, the method enhances effect of an anti-cancer therapy in a subject in need thereof, which methods including administering to a subject in need thereof: an effective amount of an immunotherapeutic construct of any one of the described embodiments, or a composition including an immunotherapeutic construct; and at least one anti-cancer agent (e.g., a chemotherapeutic agent, a targeted therapeutic agent, or an immune checkpoint inhibitor). In another example combination method, the method enhances a checkpoint blockade immunotherapy effect in a subject diagnosed as having a neoplasia, including administering to a subject in need thereof: an effective amount of an immunotherapeutic construct of any one of the described embodiments, or a composition including an immunotherapeutic construct; and at least one immune checkpoint inhibitor. Yet another combination method is a method of enhancing radiation therapy effect in a subject diagnosed as having a neoplasia, including administering to a subject in need thereof: an effective amount of an immunotherapeutic construct of any one of the described embodiments, or a composition including an immunotherapeutic construct; and at least one radiation therapy. In any of the combination method embodiments, there are provided examples in which the immunotherapeutic construct or composition and the second agent (generally, an anti-cancer therapy agent or treatment) are administered sequentially or concurrently. As used herein, the term "enhancing," in regards to the therapeutic effects of an anti-cancer therapy, refers to an increase in the therapeutic effects of the anti-cancer therapy (e.g., treatment with an anti-cancer agent, radiation therapy, or checkpoint immunotherapy) above those normally obtained when the anti-cancer therapy is administered without the immunotherapeutic constructs of the invention. "An increase in the therapeutic effects" is manifested when there is an acceleration and/or increase in intensity and/or extent of the therapeutic, effects obtained with an anti-cancer therapy. It also includes extension of the longevity of therapeutic, benefits. It can also manifest where a lower dosage, frequency of dosing, or treatment duration of the anti-cancer therapy is required to obtain the same benefits and/or effects when it is co-administered with the immunotherapeutic constructs provided by the present invention as when a higher dosage, frequency, or duration of the anti-cancer therapy is administered alone. The enhancing effect preferably, but not necessarily, results in treatment of acute symptoms for which the anti-cancer therapy alone is not effective or is less effective therapeutically. Enhancement is achieved when there is at least a 10% increase (e.g., at least 25%, at least 50%, at least 75%, or at least 100%) in the therapeutic effects when an immunotherapeutic construct of the present invention is co-administered with an anti-cancer therapy compared with administration of the anti-cancer therapy alone.

Administering an immunotherapeutic construct in any of the described method embodiments may include one or more of: injection directly into or around a tumor, lesion, or resected tumor area in the subject; or systemic injection in the subject; or topical application to the subject; or inhalation; or implantation device; or microneedle application to the subject.

In examples of any of the provided method embodiments, the subject (being treated, to which a construct or composition is being administered, or from which a cell is obtained) is a mammal; for instance, in certain embodiments the mammal is a human.

Also provided herein is a kit including an immunotherapeutic construct described herein and at least one anti-cancer agent. In some embodiments, the anti-cancer agent is a chemotherapeutic agent, a targeted therapeutic agent, or an immune check point inhibitor.

Aspects of the disclosure are now described with additional detail and options to support the teachings of the disclosure, as follows: (I) Immunotherapeutic Constructs; (II) Therapeutic Agents (that cause tumor antigen release and/or modulate an immunosuppressive tumor microenvironment); (III) Adjuvant Compounds; (IV) Optional Additional Component(s); (V) Delivery Systems; (VI) Pharmaceutical Compositions and Administration Formulations; (VII) Exemplary Methods of Use; (VIII) Kits; (IX) Exemplary Embodiments; and (X) Examples.

(I) IMMUNOTHERAPEUTIC CONSTRUCTS

Described herein is a new class of immunotherapeutics (generally, "immunotherapeutic constructs") that include an engineered particle which co-delivers adjuvant(s) and therapeutically active agent(s) to cancer cells. Embodiments provide therapeutically active agent(s) that induce antigen release (specifically, tumor antigen release) and/or modulate an immunosuppressive environment (such as a tumor microenvironment). These immunotherapeutic constructs boost the CD8+ T cell repertoire and induce systemic anti-tumor immunotherapy effects, without any need to know or identify which antigen(s) are associated with the cancer being treated.

This strategy will have many key features; they are efficacious, personalized, safe because of local delivery, durable because they train and harness body immune cells to attack cancer with memory effects, inexpensive (e.g., low dosage and low number of dosings are required), and applicable to many types of cancer.

It will be understood that the amount of each component in an immunotherapeutic construct (for instance, a therapeutic agent, an adjuvant, the delivery vehicle, or any component of the delivery vehicle) may vary, depending in the embodiment. By way of example, any individual component may make up 0.001% to 80% by weight, 0.01% to 75% by weight, 0.5 to 50% by weight, 0.5 to 10% by weight, 0.5 to 5% by weight, 1 to 10% by weight, or 2 to 4% by weight, of the immunotherapeutic construct. In some embodiments, the therapeutic agent comprises an oligonucleotide (e.g., siRNA or any other oligonucleotide described herein), and the oligonucleotide makes up 0.5 to 30% by weight of the immunotherapeutic construct, e.g., 0.5 to 10%, 1 to 5%, 5 to 15%, or 10 to 30%. In some embodiments, the therapeutic agent comprises an anti-cancer agent (e.g., a small molecule inhibitor or any other anti-cancer agent described herein), and the anti-cancer agent makes up 0.1 to 30% by weight of the immunotherapeutic construct, e.g., 0.5 to 10%, 1 to 5%, 5 to 15%, or 10 to 30%). In some embodiments, the therapeutic agent comprises an antibody, and the antibody makes up 0.1 to 30% by weight of the immunotherapeutic construct, e.g., 0.5 to 10%, 1 to 5%, 5 to 15%, or 10 to 30%.

(II) THERAPEUTIC AGENTS

Examples of therapeutically active agents (e.g., therapeutic oligonucleotides, including siRNA, miRNA, antisense oligonucleotides, sgRNA-cas9, DNA, and mRNA, as well as small molecule inhibitors, chemotherapeutics, antibodies, chemical agents, etc.) delivered to cancer and/or immune cells by the provided engineered immunotherapeutic constructs cause tumor antigen release and/or modulates an immunosuppressive tumor microenvironment. In specific embodiments, the active agents kill cancer cells, thereby releasing tumor antigens, while the co-delivered adjuvants (e.g., CpG, R848, poly I:C, etc.) prime and activate adaptive immune cells against the released tumor antigens. The activated effector cells can recognize and attack tumors at any sites in the body (including sites remote from localized delivery of the immunotherapeutic construct) as well as reducing or even preventing the spread, recurrence, or the development of new tumors harboring one or more of the same tumor antigens as the treated tumors. In certain embodiments, dose of therapeutic agents on the immunotherapeutic construct may be adjusted to lessen toxicity to beneficial immune cells. In certain embodiments, therapeutic agents that affect cancer's viability without harming immune cells are utilized on the immunotherapeutic construct. In other examples, therapeutically active agents (e.g., siRNAs, inhibitors, or other drugs against STAT3, CD39, CD73, IDO-6, PD-L1, TGF-β, antioxidants, etc.) may also be loaded on/within the delivery vehicle (e.g., particle) to modulate immunosuppressive tumor microenvironment, allowing priming and activation of immune cells to effectively attack cancer cells, utilizing antigens that are already in the tumor or whose release are triggered by the immunotherapeutic construct. Therapeutic agents can target, as an example, STAT3, IDO-1, TGF-β, CD47, NOX1-5, HSP47, XBP1, BCL2, BCL-XL, AKT1, AKT2, AKT3, MYC, HER2, HER3, AR, Survivin, GRB7, EPS8L1, RRM2, PKN3, EGFR, IRE1-alpha, VEGF-R1, RTP801, proNGF, Keratin K6A, LMP2, LMP7, MECL1, HIF1α, Furin, KSP, eiF-4E, p53, β-catenin, ApoB, PCSK9, SNALP, CD39, CD73, PD-L1, PD-1, CTLA-4, MIF, VEGF, PIGF, CXCR4, CCR2, PLK1, MTDH, Twist, Lcn2, IL-6, IL-10, SOCS1, TRAIL, p65, and mitotic kinases (e.g., PLK1, PLK2, PLK3, PLK4, CDK1, CDK2, CHK1, CHK2, BUB1, BUBR1, MPS1, NEK2, HASPIN, Aurora A). Therapeutic agents can target other immunosuppressive genes known in the art (e.g., Liu et al., *Database*, bax094, 2017; Rabinovich et al., Annu Rev Immunol, 25:267, 2010). Therapeutic agents can also inhibit the activity of immune checkpoints known in the art. The immune checkpoints beneficial for cancer treatment, when inhibited, non-exhaustively include PD-L1, PD-1, CTLA-4, LAG-3, TIM-3, B7-H3, VISTA, A2AR, IDO, etc. (Khair et al., *Frontiers Immunology*, 10:453, 2019). Altogether, immunotherapeutic construct will cause long-lasting immune-mediated anti-cancer effects. Memory adaptive immunity may also be established.

In certain embodiments, the immunotherapeutic constructs are used to activate an immune response. Such embodiments are not limited to a particular manner of activating an immune response.

Therapeutic oligonucleotides. Different types of therapeutic oligonucleotides can be used and non-exhaustively include siRNA, miRNA, antisense oligonucleotide, ribozyme, aptamer, DNA, mRNA, sgRNA (for CRISPR), and CRISPR-cas9 elements. In other words, any chains of nucleotides can be utilized in this art as long as they can specifically modulate (interfere or boost) the action or synthesis of certain genes and proteins. Each particular oligonucleotide may have a single or multiple targets. Examples of gene/protein targets of interest to the invention include immune checkpoints, transcription factors, phosphatases, kinases, etc. Specific targets include STAT3, IDO-1, TGF-β, CD47, NOX1-5, HSP47, XBP1, BCL2, BCL-XL, AKT1, AKT2, AKT3, MYC, HER2, HER3, AR, Survivin, GRB7, EPS8L1, RRM2, PKN3, EGFR, IRE1-alpha, VEGF-R1, RTP801, proNGF, Keratin K6A, LMP2, LMP7, MECL1, HIF1α, Furin, KSP, eiF-4E, p53, β-catenin, ApoB, PCSK9, SNALP, CD39, CD73, PD-L1, PD-1, CTLA-4, MIF, VEGF, PIGF, CXCR4, CCR2, PLK1, MTDH, Twist, Lcn2, IL-6, IL-10, SOCS1, TRAIL, p65, and mitotic kinases (e.g., PLK1, PLK2, PLK3, PLK4, CDK1, CDK2, CHK1, CHK2, BUB1, BUBR1, MPS1, NEK2, HASPIN, Aurora A). Therapeutic oligonucleotides can also target other Immunosuppressive genes known in the arts (e.g., Liu et al., *Database*, bax094, 2017; Rabinovich et al., Annu Rev Immunol, 25:267, 2010). Therapeutic oligonucleotides can inhibit the expression and activity of immune checkpoints known in the art. The immune checkpoints beneficial for cancer treatment, when inhibited, non-exhaustively include PD-L1, PD-1, CTLA-4, LAG-3, TIM-3, B7-H3, VISTA, A2AR, IDO, etc. (Khair et al., *Frontiers Immunology*, 10:453, 2019). Therapeutic oligonucleotides can also contain two strands that target two genes (such as siRNA against BLC2 and AKT1, siRNA against AR and MYC). They can also contain immunostimulatory sequences/elements that can thus simultaneously boost the immune response and regulate expression of target genes. They can also be designed to target the aforementioned genes that have mutations.

In certain embodiments, the immunotherapeutic constructs include as an active agent an oligonucleotide that mediates RNA interference. RNA interference is a highly conserved mechanism triggered by double-stranded RNA (dsRNA) and able to downregulate transcript of genes homologous to the dsRNA. The dsRNA is first processed by Dicer into short duplexes of 21-23 nucleotides, called short interfering RNAs (siRNAs). Incorporated in RNA-induced silencing complex (RISC), they are able to mediate gene silencing through cleavage of the target mRNA. "siRNA" or "small-interfering ribonucleic acid" refers to two strands of ribonucleotides which hybridize along a complementary region under physiological conditions. The siRNA molecules include a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. Methods to analyze and identify siRNAs with sufficient sequence identity in order to effectively inhibit expression of a specific target sequence are known in the art. A suitable mRNA target region would be the coding region. Also suitable are untranslated regions, such as the 5'-UTR, the 3'-UTR, and splice junctions as long as the regions are unique to the mRNA target.

In some embodiments, siRNA encapsulated within or associated with immunotherapeutic constructs are utilized in methods and systems involving RNA interference. Such embodiments are not limited to a particular size or type of siRNA molecule. The length of the region of the siRNA complementary to the target, for example, may be from 15 to 100 nucleotides, 18 to 25 nucleotides, 20 to 23 nucleotides, or more than 15, 16, 17 or 18 nucleotides. Where there are mismatches to the corresponding target region, the length of the complementary region is generally required to be somewhat longer.

In certain embodiments, it is contemplated that the siRNA delivery approach using immunotherapeutic constructs disclosed herein (e.g., through loading of the siRNA on an immunotherapeutic constructs) can be used to inhibit production of any gene of interest. Specific targets include STAT3, IDO-1, TGF-β, CD47, NOX1-5, HSP47, XBP1, BCL2, BCL-XL, AKT1, AKT2, AKT3, MYC, HER2, HER3, AR, Survivin, GRB7, EPS8L1, RRM2, PKN3, EGFR, IRE1-alpha, VEGF-R1, RTP801, proNGF, Keratin K6A, LMP2, LMP7, MECL1, HIF1α, Furin, KSP, eiF-4E, p53, β-catenin, ApoB, PCSK9, SNALP, CD39, CD73, PD-L1, PD-1, CTLA-4, MIF, VEGF, PIGF, CXCR4, CCR2, PLK1, MTDH, Twist, Lcn2, IL-6, IL-10, SOCS1, TRAIL, p65, and mitotic kinases (e.g., PLK1, PLK2, PLK3, PLK4, CDK1, CDK2, CHK1, CHK2, BUB1, BUBR1, MPS1, NEK2, HASPIN, Aurora A), among genes known as drivers in cancer and other diseases. Other potential immunosuppressive genes known are described in Liu et al., Database, bax094, 2017 and Rabinovich et al., Annu Rev Immunol, 25:267, 2010. Further, it is specifically contemplated that siRNA can be directed to a variant or mutated gene, rather than a wildtype gene.

One of ordinary skill in the art will understand how to access representative sequences for these targets, which are readily available in public sequence databases. The following table provides sample sequence information:

| Gene Abbreviation | Full gene name | Representative GenBank Accession #s |
| --- | --- | --- |
| STAT3 | Signal transducer and activator of transcription 3 | NM_003150.3; NM_139276.2; NM_213662.1; XM_005257616.3; XM_005257617.3; XM_011525145.2; XM_011525146.2; XM_017024972.1; XM_017024973.1; XM_017024974.1; XM_017024975.1; XM_017024976.1 |
| TGF-β | transforming growth factor beta 1 | NM_000660.6; XM_011527242.1 |
| CD47 | CD47 molecule | NM_001777.3; NM_198793.2; XM_005247908.1; XM_005247909.1; XM_017007536.1; XR_001740374.1; XR_001740375.1; XR_241521.1; XR_241522.1; XR_924218.1; XR_924219.1; XR_924220.1 |
| NOX1 | NADPH oxidase 1 | NM_001271815.1; NM_007052.4; NM_013955.2; XM_017029407.1 |
| NOX2 | cytochrome b-245 beta chain | NM_000397.3 |
| NOX3 | NADPH oxidase 3 | NM_015718.2 |
| NOX4 | NADPH oxidase 4 | NM_001143836.2; NM_001143837.1; NM_001291926.1; NM_001291927.1; NM_001291929.1; NM_001300995.1; NM_016931.4; XM_006718849.3; XM_011542857.2; XM_017017841.1; XM_017017842.1; XM_017017843.1; XM_017017844.1; XM_017017845.1; NR_120406.1 |
| NOX5 | NADPH oxidase 5 | NM_001184779.1; NM_001184780.1; NM_024505.3; NR_033671.2; NR_033672.1 |
| HSP47 | serpin family H member 1 | NM_001207014.1; NM_001235.3; XM_011545327.1 |
| XBP1 | X-box binding protein 1 | NM_001079539.1; NM_005080.3 |
| BCL2 | B-cell lymphoma 2, apoptosis regulator | NM_000633.2; NM_000657.2; XM_011526135.2; XM_017025917.1; XR_935248.2 |
| BCL-XL/S, BCL2L, BCLX, Bcl-X, PPP1R52 | B-cell lymphoma 2 like 1 | NM_001191.3; NM_001317919.1; NM_001317920.1; NM_001317921.1; NM_001322239.1; NM_001322240.1; NM_001322242.1; NM_138578.2; XM_011528964.2; XM_017027993.1; NR_134257.1; XR_001754364.1; XR_936599.2 |
| AKT1 | AKT serine/threonine kinase 1 | NM_001014431.1; NM_001014432.1; NM_005163.2; XM_005267401.1; XM_017021075.1; XM_017021076.1; XM_017021077.1; XM_017021078.1 |
| AKT2 | AKT serine/threonine kinase 2 | NM_001243027.2; NM_001243028.2; NM_001330511.1; NM_001626.5; XM_011526614.1; XM_011526615.1; XM_011526616.1; XM_011526618.1; XM_011526619.1; XM_011526620.1; XM_011526622.2; XM_017026470.1 |
| AKT3 | AKT serine/threonine kinase 3 | NM_001206729.1; NM_005465.4; NM_181690.2; XM_005272994.4; XM_005272995.2; XM_006711726.3; XM_011544012.2; XM_011544013.2; XM_011544014.2; XM_016999985.1 |

-continued

| Gene Abbreviation | Full gene name | Representative GenBank Accession #s |
| --- | --- | --- |
| MYC | MYC proto-oncogene, bHLH transcription factor | NM_002467.4 |
| HER2 | erb-b2 receptor tyrosine kinase 2 | NM_001005862.2; NM_001289936.1; NM_001289937.1; NM_001289938.1; NM_004448.3; NR_110535.1 |
| HER3 | erb-b2 receptor tyrosine kinase 3 | NM_001005915.1; NM_001982.3 |
| AR | androgen receptor | NM_000044.4; NM_001011645.3; NM_001348061.1; NM_001348063.1; NM_001348064.1 |
| Survivin (BIRC5) | baculoviral inhibitor of apoptosis repeat-containing 5 | NM_001012270.1; NM_001012271.1; NM_001168.2; XR_243654.4; XR_934452.2 |
| GRB7 | growth factor receptor bound protein 7 | NM_001030002.2; NM_001242442.1; NM_001242443.1; NM_001330207.1; NM_005310.3; XM_017024536.1; XM_017024538.1 |
| EPS8L1 | EPS8 like 1 | NM_017729.3; NM_133180.2; XM_005259020.1; XM_011527050.1; XM_011527051.2; XM_011527052.2 |
| RRM2 | ribonucleotide reductase regulatory subunit M2 | NM_001034.3; NM_001165931.1 |
| PKN3 | protein kinase N3 | NM_001317926.1; NM_013355.4; XM_005251946.3; XM_006717080.2; XM_017014649.1; XM_017014650.1 |
| EGFR | epidermal growth factor receptor | NM_001346897.1; NM_001346898.1; NM_001346899.1; NM_001346900.1; NM_001346941.1; NM_005228.4; NM_201282.1; NM_201283.1; NM_201284.1 |
| IRE1-alpha (ERN1) | endoplasmic reticulum to nucleus signaling 1 | NM_001433.3; XM_017024347.1; XM_017024348.1 |
| VEGF-R1 (FLT1) | fms related tyrosine kinase 1 | NM_001159920.1; NM_001160030.1; NM_001160031.1; NM_002019.4; XM_011535014.1; XM_017020485.1 |
| RTP801 (DDIT4) | DNA damage inducible transcript 4 | NM_019058.3 |
| Keratin | keratin 1 | NM_006121.3 |
| K6A | keratin 6A | NM_005554.3 |
| LMP2 | proteasome subunit beta 9 | NM_002800.4 |
| LMP7 | proteasome subunit beta 8 | NM_004159.4; NM_148919.3 |
| MECL1 | proteasome subunit beta 10 | NM_002801.3 |
| HIF1α | hypoxia inducible factor 1 alpha subunit | NM_001243084.1; NM_001530.3; NM_181054.2 |
| Furin | furin, paired basic amino acid cleaving enzyme | NM_001289823.1; NM_001289824.1; NM_002569.3 |
| KSP | fibroblast growth factor binding protein 2 | NM_031950.3 |
| eiF-4E | eukaryotic translation initiation factor 4E | NM_001130678.2; NM_001130679.2; NM_001331017.1; NM_001968.4 |
| p53 | tumor protein p53 | NM_000546.5; NM_001126112.2; NM_001126113.2; NM_001126114.2; NM_001126115.1; NM_001126116.1; NM_001126117.1; NM_001126118.1; NM_001276695.1; NM_001276696.1; NM_001276697.1; NM_001276698.1; NM_001276699.1; NM_001276760.1; NM_001276761.1 |
| β-catenin | catenin beta 1 | NM_001098209.1; NM_001098210.1; NM_001330729.1; NM_001904.3; XM_005264886.2; XM_006712983.1; XM_006712984.1; XM_006712985.1; XM_017005738.1 |
| ApoB | apolipoprotein B | NM_000384.2 |
| PCSK9 | proprotein convertase subtilisin/kexin type 9 | NM_174936.3; NR_110451.1 |
| SNALP | synaptosome associated protein 25 | NM_001322902.1; NM_001322903.1; NM_001322904.1; NM_001322905.1; NM_001322906.1; NM_001322907.1; NM_001322908.1; NM_001322909.1; NM_001322910.1; NM_003081.4; NM_130811.3; XM_005260808.4; XM_017028021.1; XM_017028022.1; XM_017028023.1 |
| CD39 | ectonucleoside triphosphate diphosphohydrolase 1 | NM_001098175.1; NM_001164178.1; NM_001164179.1; NM_001164181.1; NM_001164182.1; NM_001164183.1; |

| Gene Abbreviation | Full gene name | Representative GenBank Accession #s |
|---|---|---|
| | | NM_001312654.1; NM_001320916.1; NM_001776.5; XM_011540370.2; XM_011540371.2; XM_011540372.2; XM_011540373.2; XM_011540374.2; XM_011540376.2; XM_011540377.2; XM_017016958.1; XM_017016959.1; XM_017016960.1; XM_017016961.1; XM_017016962.1; XM_017016963.1; XM_017016964.1 |
| CD73 | 5'-nucleotidase ecto | NM_001204813.1; NM_002526.3 |
| PD-L1 | CD274 molecule | NM_001267706.1; NM_001314029.1; NM_014143.3; NR_052005.1 |
| PD-1 | programmed cell death 1 | NM_005018.2; XM_006712573.2; XM_017004293.1 |
| CTLA-4 | cytotoxic T-lymphocyte associated protein 4 | NM_001037631.2; NM_005214.4 |
| MIF | macrophage migration inhibitory factor (glycosylation-inhibiting factor) | NM_002415.1 |
| VEGF | vascular endothelial growth factor A | NM_001025366.2; NM_001025367.2; NM_001025368.2; NM_001025369.2; NM_001025370.2; NM_001033756.2; NM_001171622.1; NM_001171623.1; NM_001171624.1; NM_001171625.1; NM_001171626.1; NM_001171627.1; NM_001171628.1; NM_001171629.1; NM_001171630.1; NM_001204384.1; NM_001204385.1; NM_001287044.1; NM_001317010.1; NM_003376.5; |
| PlGF | phosphatidylinositol glycan anchor biosynthesis class F | NM_002643.3; NM_173074.2; XM_005264369.2; XM_011532908.2 |
| CXCR4 | C-X-C motif chemokine receptor 4 | NM_001008540.2; NM_001348056.1; NM_001348059.1; NM_001348060.1; NM_003467.2 |
| CCR2 | C-C motif chemokine receptor 2 | NM_001123041.2; NM_001123396.1; XM_011534069.1 |
| PLK1 | polo like kinase 1 | NM_005030.5 |
| MTDH | Metadherin | NM_178812.3; XM_005251099.3; XM_011517367.2; XM_011517368.2; XM_011517369.2; XM_011517370.2; XM_017013966.1; XM_017013967.1; XM_017013968.1 |
| PLK2 | Polo-like kinase 2 | NM_001252226.1; NM_006622.3 |
| PLK3 | Polo-like kinase 3 | NM_004073.3; XR_246234.4 |
| PLK4 | Polo-like kinase 4 | NM_001190799.1; NM_001190801.1 NM_014264.4; XM_005262701.2 XM_017007662.1; XM_017007663.1 |
| CDK1 | Cyclin-dependent kinase 1 | NM_001170406.1; NM_001170407.1 NM_001320918.1; NM_001786.4 NM_033379.4; XM_005270303.3 |
| CDK2 | Cyclin-dependent kinase 2 | NM_001290230.1; NM_001798.4 NM_052827.3; XM_011537732.1 |
| CHK1 | Checkpoint kinase 1 | NM_001114121.2; NM_001114122.2 NM_001244846.1; NM_001274.5 NM_001330427.1; NM_001330428.1 XM_011542560.2; XM_011542562.2 XM_017017146.1; NR_045204.1 NR_045205.1 |
| CHK2 | Checkpoint kinase 2 | NM_001005735.1; NM_001257387.1 NM_001349956.1; NM_007194.3 NM_145862.2; XM_006724114.3 XM_006724116.2; XM_011529839.2 XM_011529840.2; XM_011529841.1 XM_011529842.2; XM_011529844.2 XM_011529845.2; XM_017028560.1 XM_017028561.1; XR_937805.2 XR_937806.2; XR_937807.2 |
| BUB1 | budding uninhibited by benzimidazole 1 | NM_001278616.1; NM_001278617.1 NM_004336.4; XR_923001.2 |
| BUBR1 | budding uninhibited by benzimidazole-related 1 | NM_001211.5 |
| MPS1 | Monopolar spindle 1 kinase | NM_001039396.1 |

-continued

| Gene Abbreviation | Full gene name | Representative GenBank Accession #s |
|---|---|---|
| NEK2 | NIMA related kinase 2 | NM_001204182.1; NM_001204183.1 NM_002497.3; XM_005273147.1 |
| HASPIN | Histone H3 Associated Protein Kinase | NM_031965.2 |

Such embodiments are not limited to a particular manner of assessing the delivery profile of the siRNA in vitro and/or in vivo. In some embodiments, labelling the siRNA molecules with an imaging agent (e.g., fluorescent dye FITC, RITC, Cy™ dyes, Dylight® dyes, or Alexa Fluor® dyes) or a radiotracer permits visualization of the biodistribution of siRNA molecules at the organ level and also the intracellular delivery profile. In some embodiments, RT-PCR, FISH, IHC, flow cytometry, and western blot are used to analyze the target protein at the mRNA level and protein level, respectively.

In certain embodiments, the present disclosure provides methods for inhibiting a target gene in a cell including introducing into the cell a siRNA capable of inhibiting the target gene by RNA interference, wherein the siRNA includes two RNA strands that are complementary to each other, wherein the siRNA is loaded on to an immunotherapeutic construct. In some embodiments, the siRNA is modified with cholesterol at the 3' sense strand. In some embodiments, the cell is within a human being or an animal subject (e.g., horses, dogs, cats, or other domestic, farm, or other animals with cancer).

MicroRNAs (miRNAs) or miRNA mimics are short, non-coding RNAs that can target and substantially silence protein coding genes through 3'-UTR elements. Important roles for miRNAs in numerous biological processes have been established, but comprehensive analyses of miRNA function in complex diseases are lacking. miRNAs are initially transcribed as primary miRNAs (pri-miRNAs) that are then cleaved by the nuclear RNAses Drosha and Pasha to yield precursor-miRNAs (pre-miRNAs). These precursors are further processed by the cytoplasmic RNAse III dicer to form short double stranded miR-miR* duplexes, one strand of which is then integrated into the RNA Induced Silencing Complex (RISC) that includes the enzymes dicer and Argonaute (Ago). The mature miRNAs (~17-24nt) direct RISC to specific target sites located within the 3'UTR of target genes. Once bound to target sites, miRNAs represses translation through mRNA decay, translational inhibition and/or sequestration into processing bodies (P-bodies) (Eulalio et al., *Cell*, 132:9-14, 2008; Behm-Ansmant et al., *Cold Spring Harb. Symp. Quant. Biol.*, 71:523-530, 2006; Chu and Rana, *Plos. Biology.*, 4:e210, 2006). Recent estimates find that over 60% of protein coding genes carry 3'-UTR miRNA target sites (Friedman et al., *Genome Res.*, 19:92-105, 2009). In this regard, miRNAs act as key regulators of processes as diverse as early development (Reinhart et al., *Nature*, 403:901-906, 2000), cell proliferation and cell death (Brennecke et al., *Cell*, 113(1):25-36, 2003), apoptosis and fat metabolism (Xu et al., *Curr. Biol.*, 13(9):790-795, 2003), and cell differentiation (Chen et al., *Mol. Microbiol.*, 53843-856, 2004; Dostie et al., *RNA-A Publication of the RNA Society*, 9:180-186, 2003). In addition, studies of miRNA expression in chronic lymphocytic leukemia (Calin et al., *Proc. Natl. Acad. Sci. USA*, 105:5166-5171, 2008), colonic adenocarcinoma (Michael et al., *Mol. Cancer Res.*, 1:882-891, 2003), Burkitt's lymphoma (Metzler et al., *Genes Chromosomes Cancer*, 39:167-169, 2004), cardiac disease (Zhao et al., *Cell*, 129:303-317, 2007) and viral infection (Pfeffer et al., *Science*, 304:734-736, 2004) suggest vital links between miRNA and numerous diseases.

miRNAs thus far observed have usually been 21-22 nucleotides in length and they arise from longer precursors, which are transcribed from non-protein-encoding genes. Reviewed in Carrington and Ambros (*Science*, 301(5631): 336-338, 2003). The precursors form structures that fold back on each other in self-complementary regions; they are then processed by the nuclease Dicer in animals (or DCL1 in plants). miRNA molecules interrupt translation through precise or imprecise base-pairing with their targets. In some embodiments, a miRNA may be used as a component of a provided immunotherapeutic construct, therapeutically or administered to a subject, such as a human patient, to treat a disease such as, e.g., cancer; alternately, in some embodiments, a nucleic acid that is complementary to the miRNA may be therapeutically administered to a subject in vivo or used in vitro to generate the desired therapeutic outcome (e.g., miRNA-142-3p, miRNA-142-3p, miRNA-124, or miRNA-138). In this way, the complementary nucleic acid may be used as a template to generate the desired therapeutic miRNA (e.g., miRNA-142-3p, miRNA-142-3p, miRNA-124, or miRNA-138).

Particularly contemplated are embodiments in which a therapeutic oligonucleotide is directed to or specific for STAT3. STAT3 refers to the protein "Signal transducer and activator of transcription 3" and homologs thereof; the term includes the human protein, whether wildtype or mutant forms of the protein. In embodiments, "STAT3" refers to the protein associated with Entrez Gene 6774, OMIM 102582, UniProt P40763, and/or RefSeq (protein) NP 003141 (which refer to the protein, and associated nucleic acids, known as of the date of filing of this application). "Phosphorylated STAT3" refers to a STAT3 protein that is phosphorylated and activated by the phosphorylation. In embodiments, a phosphorylated STAT3 is phosphorylated on tyrosine 705 or the residue corresponding to tyrosine 705 in homologs. In embodiments, activation of STAT3 means the STAT3 is capable of activating transcription of other genes. In embodiments, activated STAT3 is phosphorylated on tyrosine 705, or the residue corresponding to tyrosine 705, forms dimers (e.g. homodimers or heterodimers), translocates to the nucleus, and/or activates transcription. In embodiments, activated STAT3 forms homodimers. Examples of proteins that phosphorylate STAT3 and thereby activate STAT3 include JAK2, EGFR, c-MET, and PDGF-R.

Anti-Cancer Agents. The phrase anti-cancer agent is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic agent. In some embodiments, the anti-cancer agent is a targeted therapeutic agent. In some embodiments, the anticancer agent is an immune checkpoint inhibitor. In some embodiments, the anti-cancer agent is an agent identified herein having utility in methods of treating cancer. In some embodiments, the anti-cancer agent is an agent approved by the FDA or similar regulatory agency of a country other than the USA, for treating cancer.

Examples of anti-cancer agents include, but are not limited to, MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766, PD184352, SB239063, BAY 43-9006); alkylating agents such as nitrogen mustards (e.g., mechloroethamine, cyclophosphamide, uramustine, chlorambucil, melphalan, ifosfamide), ethylenimine and methylmelamines (e.g., hexamethlymelamine and thiotepa), alkyl sulfonates (e.g., busulfan and hepsulfam), nitrosoureas (e.g., carmustine, lomusitne, semustine, and streptozocin), and triazenes (e.g., decarbazine); anti-metabolites such as folic acid analogs (e.g., methotrexate, leucovorin, raltitrexed, and pemetrexed), pyrimidine analogs (e.g., fluorouracil, floxouridine, cytarabine, capecitabine, and gemcitabine), and purine analogs (e.g., mercaptopurine, thioguanine, pentostatin, fludarabine, and 5-azathioprine); plant alkaloids (e.g., vincristine, vinblastine, vinorelbine, vindesine, podophyllotoxin, paclitaxel, docetaxel, cabazitaxel, and homoharringtonine); topoisomerase inhibitors such as camptothecin derivatives (e.g., irinotecan and topotecan), amsacrine, and epipodophyllotoxins (e.g., etoposide (VP16), etoposide phosphate, and teniposide); antibiotics such as anthracenediones (e.g., mitoxantrone), anthracyclines (e.g., doxorubicin, daunorubicin, epirubicin, and fluorodaunorunicin hydrochloride), *streptomyces*-derived antibiotics or derivatives thereof (e.g., dactinomycin, bleomycin, mitomycin, geldanamycin, plicamycin, and 17-N-allylamino-17-demethoxygeldanamycin (17-AAG; tanespimycin), clofazimine, and beta lactam derivatives; platinum-based chemotherapeutic agents (e.g., cisplatin, oxaliplatin, carboplatin); substituted urea (e.g., hydroxyurea); methyl hydrazine derivative (e.g., procarbazine), adrenocortical suppressant (e.g., mitotane and aminoglutethimide); angiogenesis-inhibiting enzymes (e.g., L-asparaginase and arginine deiminase); PI3K inhibitors (e.g., wortmannin and LY294002); mTOR inhibitors (e.g., sertraline); DNA methyltransferase inhibitors (e.g., 5-aza-2'-deoxycytidine); antisense oligonucleotides; apoptosis gene modulators; apoptosis regulators (e.g., deoxyadenosine and triptolide); BCR/ABL antagonists; bFGF inhibitor; casein kinase inhibitors (ICOS); gallium nitrate; gelatinase inhibitors; glutathione inhibitors (e.g., etanidazole); immunostimulant peptides; insulin-like growth factor-1 receptor inhibitor; leukemia inhibiting factor; matrilysin inhibitors; matrix metalloproteinase inhibitors; MIF inhibitor; mismatched double stranded RNA; mycobacterial cell wall extract; nitric oxide modulators; phosphatase inhibitors; plasminogen activator inhibitor; proteasome inhibitors (e.g., bortezomib); protein A-based immune modulator; protein kinase C inhibitors; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors/modulators (e.g., itraconazole); single chain antigen-binding protein; stem cell inhibitor; stromelysin inhibitors; synthetic glycosaminoglycans; telomerase inhibitors; thyroid stimulating hormones; translation inhibitors; urokinase receptor antagonists; gonadotropin-releasing hormone agonists (GnRH) such as goserelin and leuprolide (leuprorelin); steroids such as adrenocorticosteroids (e.g., prednisone and dexamethasone); progestins (e.g., hydroxyprogesterone caproate, megestrol acetate, medroxyprogesterone acetate); antiprogestrogens (e.g., mifepristone); estrogens (e.g., di-ethlystilbestrol and ethinyl estradiol); antiestrogens such as aromatase inhibitors (e.g., exemestane, fadrozole, letrozole, pentrozole, and anastrozole), selective estrogen receptor modulators (e.g., tamoxifen, tamoxifen methiodide, panomifene, and clomifene analogues); androgens (e.g., testosterone propionate and fluoxymesterone); antiandrogen (e.g., flutamide, finasteride, and bicalutamide); immunostimulants, levamisole, interleukins (e.g., interleukin-2) and interferons/interferon agonists (e.g., alpha-interferon); monoclonal antibodies such as anti-CD20 (e.g., rituximab), anti-HER2 (e.g., trastuzumab), anti-CD52, anti-CD25 (e.g., daclizumab), anti-HLA-DR, and anti-VEGF monoclonal antibodies); immunotoxins (e.g., anti-CD33 monoclonal antibody-calicheamicin conjugate, anti-CD22 monoclonal antibody-*pseudomonas* exotoxin conjugate, etc.); radio immunotherapeutic agents (e.g., anti-CD20 monoclonal antibody conjugated to $^{111}$In, $^{90}$Y, or $^{131}$I, etc.); statins (e.g., cerivastatin and pitavastatin); 5-T1$_B$ receptor agonists (e.g., 5-nonyloxytryptamine); BRAF kinase inhibitors (e.g., vemurafenib and dabrafenib); tyrosine kinase inhibitors such as inhibitors of one or more of EGFR, HER2, KDR, FLT4, EphB4, and Src (e.g., gefitinib (Iressa™), erlotinib (Tarceva™), cetuximab (Erbitux™) lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, AG-1478, dacomitinib/PF299804, OSI-420/desmethyl erlotinib, AZD8931, ARRY-380, AEE788, pelitinib/EKB-569, CUDC-101, WZ8040, WZ4002, WZ3146, AG-490, XL647, PD153035, BMS-599626, sorafenib, imatinib (Gleevec®), sunitinib, and dasatinib; immune-checkpoint inhibitors (e.g., anti-CTLA4, anti-PD1/L1 antibodies); PLK1 inhibitors (GSK461364, B12536, Tak960, NMS-P937, volasertib), or the like, or mixtures thereof (e.g., leuprolide+estrogen+progesterone).

Additionally, the immunotherapeutic constructs described herein can be co-administered with conventional immunotherapeutic agents including, but not limited to, immunostimulants (e.g., Bacille Calmette-Guerin (BCG), levamisole, interleukin-2, alpha-interferon, etc.), therapeutic monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), immune-checkpoint inhibitors (e.g., anti-CTLA4, anti-PD1, antiPD-L1 antibodies), and radioimmunotherapy (e.g., anti-CD20 monoclonal antibody conjugated to $^{111}$In, $^{90}$Y, or $^{131}$I, etc.). These immunotherapeutic agents can also be loaded directly onto the immunotherapeutic constructs to enhance their therapeutic effect, reduce toxicity, and reduce administration time.

In a further embodiment, the immunotherapeutic constructs described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$mSn, $^{149}$Pm, $^{153}$Sm, $^{166}$Ho, $^{177}$Lu, $^{186}$Re, $^{188}$Re, $^{211}$At and $^{212}$Bi. These radiotherapeutic agents can also be loaded directly onto the immunotherapeutic constructs to enhance the therapeutic effect, reduce toxicity, and reduce administration time.

Instead of oligonucleotides, antibodies and small molecule inhibitors interfering with or boosting the activity of target genes and proteins can be used in a similar manner.

For example, instead of siRNA against PD-1, PD-1 antibody can also be loaded on the nanoparticle as the therapeutic agent component in the herein-provided immunotherapeutic construct.

(III) ADJUVANTS

The immunotherapeutic constructs provided herein include at least one adjuvant component, e.g., contained within or otherwise associated with the delivery vehicle. The immunotherapeutic construct embodiments are not limited to a particular type of adjuvant, though specific examples are provided herein. Adjuvants may also be part of or conjugated with therapeutic agents. For example, siRNA that knocks down a target gene can be designed to contain immune-stimulatory sequence. In some embodiments, the at least one adjuvant makes up 0.5 to 20% by weight of the immunotherapeutic construct.

Generally, adjuvants are any substance whose admixture into a vaccine composition increases or otherwise modifies the immune response to a (cancer) antigen. Specifically contemplated are adjuvants with immunostimulatory activity. Adjuvants induce a nonspecific activation of the immune system, unless they are associated with antigens (e.g., adjuvants in vaccines). The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased antigen-specific T cell proliferation, death of target cells, or cytokine secretion. An adjuvant may also alter an immune response, for example, by changing a primarily humoral or Th2 response into a primarily cellular, or Th1 response.

Suitable adjuvants include TLR-binding DNA substituents such as CpG oligonucleotides (e.g., ISS 1018; Amplivax; CpG ODN 7909, CpG ODN 1826, CpG ODN D19, CpG ODN 1585, CpG ODN 2216, CpG ODN 2336, ODN 1668, ODN 1826, ODN 2006, ODN 2007, ODN 2395, ODN M362, and SD-101), DNA TLR agonists that contain a CpG sequence (e.g., dSLIM), non-CpG DNA TLR agonists (e.g., EnanDIM), and cationic peptide-conjugated CpG oligonucleotides (e.g., IC30, IC31); RNA TLR agonists (e.g., Poly I:C and Poly-ICLC); aluminum salts (e.g., aluminum hydroxide, aluminum phosphate, aluminum chloride, and aluminum potassium sulfate); anti-CD40 antibodies (e.g., CP-870,893); cytokines, such as granulocyte-macrophage colony-stimulating factor (GM-CSF); small molecule TLR agonists (e.g., imiquimod, resiquimod, gardiquimod, and 3M-052); fusion proteins (e.g., ImuFact IMP321, CyaA, and ONTAK); oil- or surfactant-based adjuvants such as MF59, Montanide IMS 1312, Montanide ISA 206, Montanide ISA 50V, and Montanide ISA-51; a plant extract such as QS21 stimulon (Aquila Biotech, Worcester, Mass., USA), which is derived from saponin; mycobacterial extracts and synthetic bacterial cell wall mimics, such as lipopolysaccharides (e.g., monophosphoryl lipid A, OM-174, OM-197-MP-EC, and Pam3Cys); xanthenone derivatives (e.g., vadimezan); mixtures thereof (e.g., AS-15); and other proprietary adjuvants such as Ribi's Detox, Quil, or Superfos. Several immunological adjuvants (e.g., MF59 specific for dendritic cells and their preparation have been described previously (Dupuis et al., Cell Immunol. 186(1): 18-27, 1998; Allison, Dev Biol Stand.; 92:3-11, 1998).

Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589) and acting as immunoadjuvants (e.g., IL-12) (Gabrilovich et al., J Immunother Emphasis Tumor Immunol. (6):414-418, 1996). Toll like receptors (TLRs) or agents that activate TLRs may also be used as adjuvants, and are important members of the family of pattern recognition receptors (PRRs) which recognize conserved motifs shared by many micro-organisms, termed "pathogen-associated molecular patterns" (PAMPS).

In some embodiments, the adjuvant includes a CpG oligonucleotide. CpG immunostimulatory oligonucleotides have also been reported to enhance the effects of adjuvants in a vaccine setting. Without being bound by any particularly mechanistic theory, CpG oligonucleotides act at least in part by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of $T_H1$ cells and strong cytotoxic T-lymphocyte (CTL) generation, even in the absence of CD4 T-cell help. The $T_H1$ bias induced by TLR9 stimulation is maintained even in the presence of vaccine adjuvants such as alum or incomplete Freund's adjuvant (IFA) that normally promote a $T_H2$ bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by two orders of magnitude, with comparable antibody responses to the full-dose vaccine without CpG in some experiments (Krieg, Nature Reviews, Drug Discovery, 5:471-484, 2006). U.S. Pat. No. 6,406,705 describes the combined use of CpG oligonucleotides, non-nucleic acid adjuvants and an antigen to induce an antigen-specific immune response. A commercially available CpG TLR9 agonist is dSLIM (double Stem Loop Immunomodulator) by Mologen (Berlin, GERMANY). Other TLR binding molecules such as RNA binding TLR 7, TLR 8 and/or TLR 9 may also be used.

Xanthenone derivatives such as, for example, vadimezan or AsA404 (also known as 5,6-dimethylaxanthenone-4-acetic acid (DMXAA)), may also be used as adjuvants according to embodiments of the invention. Alternatively, such derivatives may also be administered in parallel to the vaccine of the invention, for example via systemic or intratumoral delivery, to stimulate immunity at the tumor site. Without being bound by theory, it is believed that such xanthenone derivatives act by stimulating interferon (IFN) production via the stimulator of IFN gene ISTING) receptor (see e.g., Conlon et al., J Immunology, 190:5216-5225, 2013; and Kim et al., ACS Chem Biol, 8:1396-1401, 2013). Other examples of useful adjuvants include chemically modified CpGs (e.g. CpR, Idera), Poly(I:C) (e.g. polyi: CI2U), non-CpG bacterial DNA or RNA as well as immunoactive small molecules and antibodies such as cyclophosphamide, sunitinib, bevacizumab, Celebrex™, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

Poly-ICLC is a synthetically prepared double-stranded RNA including polyI and polyC strands of average length of 5000 nucleotides, which has been stabilized to thermal denaturation and hydrolysis by serum nucleases by the addition of poly-lysine and carboxymethylcellulose. The compound activates TLR3 and the RNA helicase-domain of MDA5, both members of the PAMP family, leading to DC and natural killer (NK) cell activation and production of a "natural mix" of type I interferons, cytokines, and chemokines. Furthermore, poly-ICLC exerts a more direct, broad host-targeted anti-infectious and possibly antitumor effect mediated by the two IFN-inducible nuclear enzyme systems, the 2' 5'-OAS and the PI/eIF2a kinase, also known as the PKR (4-6), as well as RIG-I helicase and MDA5.

Examples of immunological adjuvants that can be associated with the immunotherapeutic constructs include TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives thereof including monophosphoryl lipid A (MPL), glycopyranosyl lipid A, PET-lipid A, and 3-O-desacyl-4'-monophosphoryl lipid A. In a specific embodiment, the immunological adjuvant is MPL. In another embodiment, the immunological adjuvant is LPS. TLR ligands can also include TLR3 ligands (e.g., polyinosinic-polycytidylic acid (poly(I:C)), TLR7 ligands (e.g., imiquimod and resiquimod), and TLR9 ligands.

As used herein, the term "TLR-binding DNA substituent" refers to a substituent or moiety capable of binding to a toll-like receptor ("TLR"), including at least one deoxyribonucleic acid. In embodiments, a TLR-binding DNA substituent is a nucleic acid. In embodiments, the TLR-binding DNA substituent includes at least one nucleic acid analog. In embodiments, the TLR-binding DNA substituent includes at least one nucleic acid analog having an alternate backbone (e.g. phosphodiester derivative (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite), peptide nucleic acid backbone(s), LNA, or linkages). In embodiments, a TLR-binding DNA substituent includes DNA. In embodiments, all nucleotide sugars in a TLR-binding DNA substituent are deoxyribose (e.g., all nucleotides are DNA). In embodiments, a TLR-binding DNA substituent includes or is DNA having internucleotide linkages selected from phosphodiesters and phosphodiester derivatives (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite, or combinations thereof). In embodiments, a TLR-binding DNA substituent includes DNA having internucleotide linkages selected from phosphodiesters and phosphorothioates. In embodiments, a TLR-binding DNA substituent includes or is DNA having backbone linkages selected from phosphodiesters and phosphorodithioates. In embodiments, a TLR-binding DNA substituent includes or is DNA including phosphodiester backbone linkages. In embodiments, a TLR-binding DNA substituent includes or is DNA including phosphorothioate backbone linkages. In embodiments, a TLR-binding DNA substituent includes or is DNA including phosphorodithioate backbone linkages. In embodiments, a TLR-binding DNA substituent preferentially binds TLR9 over other TLR. In embodiments, a TLR-binding DNA substituent specifically binds TLR9. In embodiments, a TLR-binding DNA substituent specifically binds TLR3. In embodiments, a TLR-binding DNA substituent specifically binds TLR7. In embodiments, a TLR-binding DNA substituent specifically binds TLR8. In embodiments, a TLR-binding DNA substituent specifically binds a cellular sub-compartment (e.g. endosome) associated TLR (e.g. TLR3, TLR7, TLR8, or TLR9). In embodiments, a TLR-binding DNA substituent includes or is a G-rich oligonucleotide. In embodiments, a TLR-binding DNA substituent includes a CpG motif, wherein C and G are nucleotides and p is the phosphate connecting the C and G. In embodiments, the CpG motif is unmethylated. In embodiments, a TLR-binding DNA substituent is a Class A CpG oligodeoxynucleotide (ODN). In embodiments, a TLR-binding DNA substituent is a Class B CpG oligodeoxynucleotide (ODN). In embodiments, a TLR-binding DNA substituent is a Class C CpG oligodeoxynucleotide (ODN). In embodiments, a TLR-binding DNA substituent (e.g., TLR9-binding DNA substituent) include deoxyribonucleic acids with A, G, C, or T bases and phosphodiester linkages and/or phosphodiester derivative linkages (e.g., phosphorothioate linkage(s)).

The phrase "CpG motif" refers to a 5' C nucleotide connected to a 3' G nucleotide through a phosphodiester internucleotide linkage or a phosphodiester derivative internucleotide linkage. In embodiments, a CpG motif includes a phosphodiester internucleotide linkage. In embodiments, a CpG motif includes a phosphodiester derivative internucleotide linkage.

As used herein, the term "Class A CpG ODN" or "A-class CpG ODN" or "D-type CpG ODN" or "Class A CpG DNA sequence" is used in accordance with its common meaning in the biological and chemical sciences and refers to a CpG motif including oligodeoxynucleotide including one or more of poly-G sequence at the 5', 3', or both ends; an internal palindrome sequence including CpG motif; or one or more phosphodiester derivatives linking deoxynucleotides. In embodiments, a Class A CpG ODN includes poly-G sequence at the 5', 3', or both ends; an internal palindrome sequence including CpG motif; and one or more phosphodiester derivatives linking deoxynucleotides. In embodiments, the phosphodiester derivative is phosphorothioate. Examples of Class A CpG ODNs include ODN D19, ODN 1585, ODN 2216, and ODN 2336.

The terms "Class B CpG ODN" or "B-class CpG ODN" or "K-type CpG ODN" or "Class B CpG DNA sequence" are used in accordance with their common meaning in the biological and chemical sciences, and refer to a CpG motif including oligodeoxynucleotide including one or more of a 6mer motif including a CpG motif; phosphodiester derivatives linking all deoxynucleotides. In embodiments, a Class B CpG ODN includes one or more copies of a 6mer motif including a CpG motif and phosphodiester derivatives linking all deoxynucleotides. In embodiments, the phosphodiester derivative is phosphorothioate. In embodiments, a Class B CpG ODN includes one 6mer motif including a CpG motif. In embodiments, a Class B CpG ODN includes two copies of a 6mer motif including a CpG motif. In embodiments, a Class B CpG ODN includes three copies of a 6mer motif including a CpG motif. In embodiments, a Class B CpG ODN includes four copies of a 6mer motif including a CpG motif. Examples of Class B CpG ODNs include ODN 1668, ODN 1826, ODN 2006, and ODN 2007.

The terms "Class C CpG ODN" or "C-class CpG ODN" or "C-type CpG DNA sequence" are used in accordance with their common meaning in the biological and chemical sciences and refers to an oligodeoxynucleotide including a palindrome sequence including a CpG motif and phosphodiester derivatives (phosphorothioate) linking all deoxynucleotides. Examples of Class C CpG ODNs include ODN 2395 and ODN M362.

(IV) OPTIONAL ADDITIONAL COMPONENTS

Targeting Moieties

One or more targeting moieties (a.k.a., targeting molecules) can be included, e.g., loaded into, attached to the surface of, and/or enclosed within the delivery vehicle. In embodiments, the targeting moiety is displayed on the exterior surface of the delivery vehicle. In certain embodiments, such targeting moieties allow specific cell targeting (e.g., preventing delivery of toxic therapeutic agents to immune cells, enriching/targeting delivery of therapeutic agents with cell-specific function). In certain embodiments, targeting moieties may also have therapeutic activity and thus also serve as therapeutic agents of the herein-provided immunotherapeutic construct (e.g., PD-L1 antibody). Such targeting moieties may be particularly beneficial for systemic delivery.

Exemplary targeting molecules include proteins, peptides, ligands, nucleic acids, lipids, saccharides, antibodies, aptamers, affibody molecules, ligands, small molecules, or polysaccharides that bind to one or more targets associated with an organ, tissue, cell, or extracellular matrix, or specific type of tumor or infected cell. The degree of specificity with which the delivery vehicles are targeted can be modulated through the selection of a targeting molecule with the appropriate affinity and specificity. For example, antibodies are very specific. These can be polyclonal, monoclonal, fragments, recombinant, or single chain, many of which are commercially available or readily obtained using standard techniques. T-cell specific molecules, antigens, and tumor targeting molecules can be bound to the surface of the immunotherapeutic constructs. The targeting molecules may be conjugated to the terminus of one or more PEG chains present on the surface of the particle.

In some embodiments, the targeting moiety is an antibody or antigen binding fragment (e.g., single chain variable fragments) thereof that specifically recognizes a cell or tumor marker that is present exclusively or in elevated amounts on a target cell, such as a malignant cell (e.g., a tumor antigen). Suitable targeting molecules that can be used to direct immunotherapeutic constructs to cells and tissues of interest, as well as methods of conjugating target molecules to nanoparticles, are known in the art. See, for example, Ruoslahti et al. (Nat. Rev. Cancer, 2:83-90, 2002). Exemplary tumor antigens that can be targeted with antigen binding molecules such as antibodies are discussed above with respect to vaccine antigens. In certain cases, therapeutic agents can be toxic to both cancer and immune cells, resulting in suboptimal efficacy. Thus, in certain embodiments, immunotherapeutic constructs can be conjugated with a targeting moiety to enrich the delivery of therapeutic agent and adjuvant to only cancer cells. Examples include antibodies against HER2, EGFR, PSMA, PD-L1, etc. that are expressed or optionally overexpressed on cancer cells. In some embodiments, immunotherapeutic constructs can be conjugated with a targeting moiety to enrich the delivery of therapeutic agent and adjuvant to only immune cells.

Targeting molecules can also include neuropilins and endothelial targeting molecules, integrins, selectins, adhesion molecules, bone targeting molecules such as zoledronic acid and alendronic acid (e.g., to target cancer metastasized to bone), stroma, and fibroblast targeting molecules.

In some embodiments, the targeting moiety targets the immunotherapeutic construct to antigen-presenting cells (APCs), and particularly to a subclass of APCs known as dendritic cells. Dendritic cells express a number of cell surface receptors that can mediate endocytosis. In some embodiments, immunotherapeutic construct enhances the activity of DC to process tumor antigen and thus better trigger in situ tumor vaccination. Targeted delivery to DC may be performed. Targeting exogenous antigens to internalizing surface molecules on systemically-distributed antigen presenting cells facilitates uptake of the particle and can overcomes a major rate-limiting step in the therapy.

Dendritic cell targeting molecules include monoclonal or polyclonal antibodies or fragments thereof that recognize and bind to epitopes displayed on the surface of dendritic cells. Dendritic cell targeting molecules also include ligands which bind to a cell surface receptor on dendritic cells. One such receptor, the lectin DEC-205, has been used in vitro and in mice to boost both humoral (antibody-based) and cellular (CD8 T cell) responses by 2-4 orders of magnitude (Hawiger et al., J. Exp. Med., 194(6):769-79, 2001; Bonifaz et al., J. Exp. Med., 196(12):1627-38 2002; Bonifaz et al., J. Exp. Med., 199(6):815-24, 2004). In these reports, antigens were fused to an anti-DEC205 heavy chain and a recombinant antibody molecule was used for immunization.

A variety of other endocytic receptors, including a mannose-specific lectin (mannose receptor) and IgG Fc receptors, have also been targeted in this way with similar enhancement of antigen presentation efficiency. Other suitable receptors which may be targeted include DC-SIGN, 33D1, SIGLEC-H, DCIR, CD11c, heat shock protein receptors and scavenger receptors. Targeting moieties for these receptors can be attached to the immunotherapeutic constructs for their preferential uptake into immune cells that express these receptors. Example is mannose attached on the immunotherapeutic constructs for targeted delivery to macrophages and DCs that have high levels of mannose receptors.

Other receptors which may be targeted include the toll-like receptors (TLRs). TLRs recognize and bind to pathogen-associated molecular patterns (PAMPs). PAMPs target the TLR on the surface of the dendritic cell and signals internally, thereby potentially increasing DC antigen uptake, maturation and T-cell stimulatory capacity. PAMPs conjugated to the particle surface or co-encapsulated include unmethylated CpG DNA (bacterial), double-stranded RNA (viral), lipopolysaccharide (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

Targeting molecules can be covalently bound to delivery vehicles using a variety of methods known in the art. In preferred embodiments the targeting moiety is attached to the delivery vehicle by PEGylation or a biotin-avidin bridge.

CD40 Agonist. In a particular embodiment, the targeting moiety targets CD40. The moiety can be a CD40 agonist. The cell surface molecule CD40 is a member of the tumor necrosis factor receptor superfamily and is broadly expressed by immune, hematopoietic, vascular, epithelial, and other cells, including a wide range of tumor cells. As a potential target for cancer therapy, CD40 may mediate tumor regression through both an indirect effect of immune activation and a direct cytotoxic effect on the tumor, resulting in a "two-for-one" mechanism of action of CD40 agonists. CD40 agonists are known in the art and reviewed in Vonderheide (*Clin Cancer Res,* 13(4):1083-1088, 2007). Exemplary agonists include recombinant CD40L (recombinant human trimer), CD-870, 893 (fully human IgG2 mAb), SGN-40 (humanized IgG1), and HCD 122 (fully human IgG1 mAb). Soluble agonistic CD40 antibodies have been shown to substitute for T-cell help provided by CD4+ lymphocytes in murine models of T cell-mediated immunity (Khalil et al., *Update Cancer Ther.,* 2:61-65, 2007).

Integrin Ligand. In another embodiment, the targeting moiety is a ligand for an integrin. Studies show that integrins are overexpressed on the surface of tumor cells and can thus serve as a marker that distinguishes between tumor cells and normal cells. Certain integrins also activate TGF-β through an extracellular pathway. After latent TGF-β is released from a tumor cell, it binds with integrin on the surface of the tumor cell, leading to the activation of the latent TGF-β. Increased TGF-β concentrations in the tumor microenvironment support immune suppression and recruit regulatory T cells to the tumor environment.

RGD peptide can serve a dual function: it is not only a typical integrin-targeting ligand (Ruoslahti et al., *Annu. Rev. Cell Dev. Biol.,* 12:697-715, 1996) but also serves as an immune danger signal, activating APCs (Altincicek et al., *Biol Chem.,* 390, 1303-11, 2009). Therefore, in a preferred embodiment, RGD peptide is loaded into, attached to the surface of, and/or enclosed within the delivery vehicle.

T Cell Receptor that Recognizes the p53 Antigen. In a particular embodiment, the targeting moiety is a T cell receptor (TCR) that recognizes the p53 antigen within the context of human MHC. T cell receptor recombinant proteins derived from bacterial, eukaryotic or yeast cells including T cell receptors composed of the alpha, beta chains or gamma/delta chains (α/β TCR or γ/Δ TCRs).

IL-15/IL-15Rα. In another embodiment, the targeting moiety is an IL-15/1L-15Rα complex. Interleukin-15 (IL-15) is a cytokine that shares certain receptor subunits with IL-2 and thus has some overlapping mechanisms of action. IL-15 is expressed by dendritic cells and provides a critical signal for the proliferation and priming of natural killer (NK) cells. Accordingly, IL-15/1L-15Rα complex can be used to target nanoparticulate compositions to, for example, natural killer (NK) cells.

(V) DELIVERY SYSTEMS

Embodiments of the herein-provided immunotherapeutic constructs are agnostic as to the delivery system employed for delivery of the therapeutic agent and adjuvant. Thus, in various embodiments, the delivery system can use or be based on any type of known or to-be-developed particulate delivery vehicle. These include nanoparticles, fullerenes, endohedral metallofullerenes, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, lipid-based nanoparticles, lipoplex, polymeric nanoparticles, calcium phosphate particles, aluminum salt particles, polyplex, nanoshells, dendrimers, microparticles, quantum dots, superparamagnetic nanoparticles, nanorods, cellulose nanoparticles, glass and polymer micro- and nano-spheres, biodegradable PLGA micro- and nano-spheres, gold nanoparticles, adjuvant particles (e.g., virosomes or other virus-like particles), silver nanoparticles, carbon nanoparticles, iron nanoparticles, porous and non-porous silica nanoparticles, and modified micelles. Hybrid particles that include several classes of materials can also be used. Particles in nanometer and micron sizes can be used. The particles can be of any shape, structure, and porosity. Therapeutic agents, adjuvants, and any additional compounds can be included with the delivery agent by any suitable means, e.g., loaded into, attached to the surface of, coupled to, enclosed within, or contained within the delivery system. Such agents may be encapsulated, covalently bound, or non-covalently bound (e.g., by electrostatic, hydrophobic, van der Waals, or compound-specific interaction (such nucleic acid base pairing, ligand-receptor, antibody-antigen, biotin-avidin, etc.).

In some embodiments, the delivery system includes a mesoporous silica nanoparticle (MSNP), such as those described in U.S. Patent Publication No. US2017/0173169 or No. US2017/0172923, the MSNPs described therein are hereby incorporated by reference.

In some embodiments, the mean particle size of the mesoporous nanoparticle (or a different nanoparticle) is about 5 nm to about 200 nm, about 5 nm to about 90 nm, about 5 nm to about 20 nm, about 30 nm to about 100 nm, about 30 nm to about 80 nm, about 30 nm to about 60 nm, about 40 nm to about 80 nm, about 70 nm to about 90 nm, or about 5 nm, about 10 nm, about 20 nm, about 30 nm, about 40 nm, about 50 nm, about 60 nm, about 70 nm, about 80 nm, about 90 nm, or about 100 nm. In some embodiments, the mesoporous silica nanoparticle is coated with cationic polymers or other compounds. The cationic polymer may bind to the surface of the nanoparticle using any appropriate means. In some embodiments, the cationic polymer binds to the nanoparticle via electrostatic interaction. The cationic polymer may be any polymer with a positive charge, such as, but not limited to, PEI, polyamidoamine, poly(allylamine), poly(diallyldimethylammonium chloride), chitosan, poly(N-isopropyl acrylamide-co-acrylamide), poly (N-isopropyl acrylamide-co-acrylic acid), poly(L-lysine), diethylaminoethyl-dextran, poly-(N-ethyl-vinylpyridinium bromide), poly(dimethylamino)ethyl methacrylate), or poly (ethylene glycol)-co-poly(trimethylaminoethylmethacrylate chloride). Other cationic polymers will be apparent to those of skill in the art, and may be found, for example, in Polymer Handbook, 4th Edition, Edited by: Brandrup, E. H. Immergut, and E. A. Grukle; John Wiley & Sons, 2003).

The cationic polymers may be linear or branched. In some embodiments, the cationic polymers may range in size from about 500 Da to 25 kDa and may be branched or linear. For example, branched PEI with an average size of 1.8 kDa to 10 kDa may be loaded onto the nanoparticle core. The ratio of cationic polymer to nanoparticle may be varied depending on the desired result. The cationic polymer may be present at 1 to 50 wt. % of the nanoconstruct, e.g., 5 to 40 wt. %, 10 to 30 wt. %, 20 to 30 wt. %, 5 to 15 wt. %, 5 to 20 wt. %, 5 to 25 wt. %, 5 to 30 wt. %, 10 to 20 wt. %, 10 to 25 wt. %, or 25 to 40 wt. %, e.g., about 5, 10, 15, 20, 25, 30, or 35 wt. %. In some embodiments, the cationic polymer is present at 10 to 20 wt. %.

In some embodiments, the cationic polymer is cross-linked, e.g., with a cleavable disulfide bond, pre- or post-coating on the nanoparticle. In some embodiments, the attached cationic polymer is crosslinked after binding to the nanoparticles, e.g., MSNP, using, for example, DSP (dithiobis[succinimidyl propionate]), DTSSP (3,3'-dithiobis (sulfosuccinimidyl propionate), and DTBP (dimethyl 3,3'-dithiobispropionimidate). The crosslinking may occur in the absence or presence of free cationic polymer in solution. In other embodiments, the cationic polymer is not crosslinked.

A stabilizer may be conjugated to the MSNP (or a different nanoparticle) and/or the cationic polymer, e.g., by any appropriate means. In some embodiments, a stabilizer is conjugated to an amine or other reactive group of a crosslinked cationic polymer coated on the nanoparticle (e.g., a MSNP). Exemplary stabilizers include, but are not limited to, PEG, dextran, polysialic acid, hyaluronic acid, polyvinyl pyrrolidone, polyvinyl alcohol, and polyacrylamide, or a combination thereof.

A stabilizer may have multiple chemically reactive groups, e.g., for attachment to the nanoparticle, cationic polymer, and/or other component. For example, a reactive stabilizer, e.g., a PEG derivative, may have two electrophilic moieties, such as maleimide-PEG-N-hydroxysuccinimidyl ester (Mal-PEG-NHS), which contains both a Michael acceptor and an activated ester. The stabilizer, e.g., PEG, used in conjunction with the compositions and methods of the invention generally has a molecular weight ranging between 500 Da-40 kDa, e.g., 2-10 kDa. The stabilizer may be present at 1 to 50 wt. % of the nanoconstruct, e.g., 5 to 30 wt. %, 10 to 20 wt. %, 10 to 25 wt. %, 5 to 15 wt. %, 5 to 20 wt. %, 5 to 25 wt. %, or 1 to 10 wt. %, e.g., about 5, 10, 15, 20, 25, 35, 40 or 45 wt. %.

"Mean particle size" as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean hydrodynamic particle size can be measured using methods known in the art, such as dynamic light scattering.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% of the distribution lies within 15% of the median particle size, more preferably within 10% of the median particle size, most preferably within 5% of the median particle size.

"Nanoparticle", as used herein, generally refers to a particle having a diameter from 5 nm up to, but not including, 1 micron, preferably from 20 nm to 1 micron. The particles can have any shape. Nanoparticles having a spherical shape are generally referred to as "nanospheres". The present disclosure is not limited to specific types or kinds of nanoparticles for complexing with adjuvants and therapeutically agents configured for treating or preventing cancer and related hyperproliferative disorders.

Examples of nanoparticles include fullerenes (a.k.a. $C_{60}$, $C_{70}$, $C_{76}$, $C_{80}$, $C_{84}$), endohedral metallofullerenes (EMI's), which contain additional atoms, ions, or clusters inside their fullerene cage), trimetallic nitride templated endohedral metallofullerenes (TNT EMEs, high-symmetry four-atom molecular cluster endohedrals, which are formed in a trimetallic nitride template within the carbon cage), single-walled and multi-walled carbon nanotubes, branched and dendritic carbon nanotubes, gold nanorods, silver nanorods, single-walled and multi-walled boron/nitrate nanotubes, carbon nanotube peapods (nanotubes with internal metallo-fullerenes and/or other internal chemical structures), carbon nanohorns, carbon nanohorn peapods, lipid particles liposomes, lipoplex, polymeric nanoparticles, polyplex, nanoshells, dendrimers, quantum dots, superparamagnetic nanoparticles, nanorods, adjuvant particles (e.g., virosomes or other virus-like particles), and cellulose nanoparticles. Other exemplary nanoparticles include glass and polymer micro- and nano-spheres, biodegradable PLGA micro- and nano-spheres, gold, silver, platinum, carbon, and iron nanoparticles.

In some embodiments, the nanoparticle is a modified micelle. In these embodiments, the modified micelle includes polyol polymers modified to contain a hydrophobic polymer block. The term "hydrophobic polymer block" as used in the present disclosure indicates a segment of the polymer that on its own would be hydrophobic. The term "micelle" as used herein refers to an aggregate of molecules dispersed in a liquid. A typical micelle in aqueous solution forms an aggregate with the hydrophilic "head" regions in contact with surrounding solvent, sequestering the hydrophobic single tail regions in the micelle center. In some embodiments the head region may be, for example, a surface region of the polyol polymer while the tail region may be, for example, the hydrophobic polymer block region of the polyol polymer.

The invention further encompasses use of particles on the micrometer scale in addition to the nanometer scale. Where microparticles are used, it is preferred that they are relatively small, on the order of 1-50 micrometers. For ease of discussion, the use herein of "nanoparticles" encompasses true nanoparticles (sizes of from 1 nm to 1000 nm), microparticles (e.g., from 1 micrometer to 50 micrometers), or both.

Examples of nanoparticles include, by way of example and without limitation, paramagnetic nanoparticles, superparamagnetic nanoparticles, metal nanoparticles, fullerene-like materials, inorganic nanotubes, dendrimers, dendrimers with covalently attached metal chelates, nanofibers, nanohorns, nano-onions, nanorods, nanoropes, adjuvant particles (e.g., virosomes or other virus-like particles), and quantum dots. In some embodiments, a nanoparticle is a metal nanoparticle (for example, a nanoparticle of gold, palladium, platinum, silver, copper, nickel, cobalt, iridium, or an alloy of two or more thereof). Nanoparticles can include a core or a core and a shell, as in core-shell nanoparticles. Hybrid particles that include several classes of materials can also be used.

Immunotherapeutic construct-containing compositions including one or more active agents and one or more adjuvant compounds each loaded into, attached to the surface of, and/or enclosed within a delivery vehicle, are disclosed. The nanoparticulate compositions offer a number of advantages over delivering the active agent or agents to the target cells in solution. For example, the nanoparticulate compositions present a localized concentration of the one or more active agents on or in a nanoparticle leading to increased avidity when the nanoparticle encounters the target cells. The nanoparticulate compositions can also serve as a depot of active agent with tunable release kinetics that can extend over several days to prolong effective systemic half-life and efficacy of the agent or agents.

Typically, two or more active agents (including one therapeutic agent and one adjuvant) are loaded into, attached to the surface of, and/or enclosed within a delivery vehicle. The relative concentrations of each of the two or more active agents and their location on or within the delivery vehicle can be manipulated during manufacture of the compositions to adapt a preferred dosage and presentation that will be received by the target cell. Loading of two or more active agents into or onto the same delivery vehicle allows the two or more active agents to be presented to the target cell or same tumor microenvironment simultaneously or in an otherwise predetermined order to the target cell.

The delivery vehicles can be, for example, nanolipogels, polymeric particles, silica particles, liposomes, or multilamellar vesicles. In the certain embodiments, the particulate delivery vehicles are nanoscale compositions, for example, 10 nm up to, but not including, 1 micron. However, it will be appreciated that in some embodiments, and for some uses, the particles can be smaller, or larger (e.g., microparticles, etc.). Although example immunotherapeutic constructs disclosed herein may be referred to nanoparticulate compositions, it will be appreciated that in some embodiments and for some uses the particulate compositions can be somewhat larger than nanoparticles. For example, particulate compositions can also be between 1 micron to 1000 microns. Such compositions can be referred to as microparticulate compositions.

In embodiments for treating cancer it is desirable that the particle be of a size suitable to access the tumor microenvironment. In particular embodiments, the particle is of a size suitable to access the tumor microenvironment and/or the tumor cells by enhanced permeability and retention (EPR) effect. EPR refers to the property by which certain sizes of molecules (e.g., the particulate compositions discussed herein) tend to accumulate in tumor tissue much more than they do in normal tissues. Therefore, in compositions for treatment of cancer, the delivery vehicle is preferably in the range of 25 nm to 500 nm inclusive, more preferably in the range of 30 nm to 300 nm inclusive.

Nanolipogels. Nanolipogels are core-shell nano-particulates that combine the advantages of both liposomes and polymer-based particles for sustained delivery of active agents. In some of these embodiments and applications nanolipogels can exhibit, increased loading efficiency, increased sustained release, and improved therapeutic efficacy for combinations of macromolecules and molecules compared to conventional nanoparticle compositions.

Typically, the outer shell of the nanolipogel protects cargo and, provides biocompatibility as well as a surface for functionalization with targeting molecule(s). The outer shell encapsulates components so they are not exposed until desired, for example, in response to environmental conditions or stimuli, creating monodisperse, reproducible particle populations, and mediating internalization into desired cell types. The inner core, which can be a dendrimer or other polymer, has separate and additive functionalities to the outer shell. For example, the inner shell allows for secondary deposition of drug, vaccine, or imaging agent; increases loading of components with different physiochemical properties into the particle; allows for tunable release of contents from particles; increases cytosolic availability of DNA/RNA, drug, and/or protein by disrupting endosomes, all leading to enhanced drug effects, antigen presentation, and transfection/silencing Nanolipogels have a polymer matrix core containing one or more host molecules. The polymeric matrix is preferably a hydrogel, such as a crosslinked block copolymer containing one or more poly(alkylene oxide) segments, such as polyethylene glycol, and one or more aliphatic polyester segments, such as polylactic acid. One or more cargo molecules is dispersed within or covalently bound to the polymeric matrix. The hydrogel core is surrounded by a liposomal shell.

Nanolipogels can be constructed to incorporate a variety of active agents that can subsequently be released in a controlled fashion. Active agents can be dispersed within the hydrogel matrix, dispersed within the liposomal shell, covalently attached to the liposomal shell, and combinations thereof. Active agents can be selectively incorporated at each of these locales within the nanolipogel. Furthermore, the release rate of active agents from each of these locales can be independently tuned. Because each of these locales possesses distinct properties, including size and hydrophobicity/hydrophilicity, the chemical entities independently incorporated at each of these locales can differ dramatically with respect to size and composition. For example, nanolipogels can be loaded with one or more compounds dispersed within the polymeric matrix as well as small molecule hydrophobic drugs associated and adjuvant(s). Nanolipogels can be loaded provide simultaneous sustained release of agents that differ widely in chemical composition and molecular weight.

Nanolipogels are typically spherical in shape, with average particle sizes ranging between 50 nm and 1000 nm, more preferably between 75 nm and 300 nm, most preferably between 90 nm and 200 nm. In certain embodiments, the nanolipogels possess an average particle size between 100 nm and 140 nm. Particles may be non-spherical.

Depending upon the nature of the lipids present in the liposomal shell of the nanolipogels, nanolipogels having a positive, negative, or near neutral surface charge may be prepared. In certain embodiments, the nanolipogels possess a near neutral surface charge. In certain embodiments, the nanolipogels possess a $\zeta$-potential of between 10 mV and −10 mV, more preferably between 5 mV and −5 mV, more preferably between 3 mV and −3 mV, most preferably between 2 mV and −2 mV.

Hydrophobic active agents, such as proteins, may be covalently connected to the surface of the nanolipogel, whereas hydrophilic active agents may be covalently connected to the surface of the nanolipogel or dispersed within the liposomal shell. In certain embodiments, the liposomal shell includes one or more PEGylated lipids. In these cases, one or more active agents may be conjugated to the terminus of one or more PEG chains present on the surface of the liposomal shell.

In another embodiment, the lipid is modified to include an avidin moiety, enabling a biotinylated targeting moiety, detectable label, or other active agent to be coupled thereto, if so desired.

In particular embodiments, one or more active agents are covalently connected to the surface of the nanolipogel via a linking group that is cleaved in response to an external chemical or physical stimulus, such as a change in ambient pH, so as to trigger release of the active agent at a desired physiological locale.

Core. The nanolipogel core is formed from a polymeric matrix. The matrix can include one or more host molecules as discussed in more detail below. The nanolipogel core may further include one or more active agents. The active agents may be complexed to a host molecule, dispersed with polymeric matrix, or combinations thereof.

The polymeric matrix of the nanolipogels may be formed from one or more polymers or copolymers. By varying the composition and morphology of the polymeric matrix, one can achieve a variety of controlled release characteristics, permitting the delivery of moderate constant doses of one or more active agents over prolonged periods of time.

The polymeric matrix may be formed from non-biodegradable or biodegradable polymers; however, preferably, the polymeric matrix is biodegradable. The polymeric matrix can be selected to degrade over a time period ranging from one day to one year, more preferably from seven days to 26 weeks, more preferably from seven days to 20 weeks, most preferably from seven days to 16 weeks. Biodegradable cross-linkers may be used to increase molecular weight of polymers, which are clearable from the body as small fragments after degradation of the cross-linkers.

In general, synthetic polymers are preferred, although natural polymers may be used. Representative polymers include poly(hydroxy acids) such as poly(lactic acid), poly(glycolic acid), poly(lactic acid-co-glycolic acids), polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); poly(glycolide-co-caprolactones); polycarbonates such as tyrosine polycarbonates; polyamides (including synthetic and natural polyamides), polypeptides, and poly(amino acids); polyesteramides; other biocompatible polyesters; poly(dioxanones); poly(alkylene alkylates); hydrophilic polyethers; polyurethanes; polyetheresters; polyacetals; polycyanoacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), polyvinyl alcohols, polyvinylpyrrolidone; poly(alkylene oxides) such as polyethylene glycol (PEG); derivativized celluloses such as alkyl celluloses (e.g., methyl cellulose), hydroxyalkyl celluloses (e.g., hydroxypropyl cellulose), cellulose ethers, cellulose esters, nitrocelluloses, polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), as well as derivatives, copolymers, and blends thereof.

As used herein, "derivatives" include polymers having substitutions, additions of chemical groups and other modifications to the polymeric backbones described above routinely made by those skilled in the art. Natural polymers, including proteins such as albumin, collagen, gelatin, prolamines, such as zein, and polysaccharides such as alginate and pectin, may also be incorporated into the polymeric matrix. While a variety of polymers may be used to form the polymeric matrix, generally, the resulting polymeric matrix will be a hydrogel. In certain cases, when the polymeric matrix contains a natural polymer, the natural polymer is a biopolymer which degrades by hydrolysis, such as a polyhydroxyalkanoate.

The polymeric matrix may optionally contain one or more crosslinkable polymers. Preferably, the crosslinkable polymers contain one or more photo-polymerizable groups, allowing for the crosslinking of the polymeric matrix following nanolipogel formation. Examples of suitable photo-polymerizable groups include vinyl groups, acrylate groups, methacrylate groups, and acrylamide groups. Photo-polymerizable groups, when present, may be incorporated within the backbone of the crosslinkable polymers, within one or more of the sidechains of the crosslinkable polymers, at one or more of the ends of the crosslinkable polymers, or combinations thereof.

The polymeric matrix may be formed from polymers having a variety of molecular weights, so as to form nanolipogels having properties, including drug release rates, optimal for specific applications. Generally, the polymers which make up the polymeric matrix possess average molecular weights ranging between 500 Da and 50 kDa. In cases where the polymeric matrix is formed from non-crosslinkable polymers, the polymers typically possess average molecular weights ranging between 1 kDa and 50 kDa, more preferably between 1 kDa and 70 kDa, most preferably between 5 kDa and 50 kDa. In cases where the polymeric matrix is formed from crosslinkable polymers, the polymers typically possess lower average molecular weights ranging between 500 Da and 25 kDa, more preferably between 1 kDa and 10 kDa, most preferably between 3 kDa and 6 kDa. In particular embodiments the polymeric matrix is formed from a crosslinkable polymer having an average molecular weight of 5 kDa.

In some embodiments, the polymeric matrix is formed from a poly(alkylene oxide) polymer or a block copolymer containing one or more poly(alkylene oxide) segments. The poly(alkylene oxide) polymer or poly(alkylene oxide) polymer segments may contain between 8 and 500 repeat units, more preferably between 40 and 300 repeat units, most preferably between 50 and 150 repeat units. Suitable poly(alkylene oxides) include polyethylene glycol (also referred to as polyethylene oxide or PEG), polypropylene 1,2-glycol, poly(propylene oxide), polypropylene 1,3-glycol, and copolymers thereof.

In some embodiments, the polymeric matrix is formed from an aliphatic polyester or a block copolymer containing one or more aliphatic polyester segments. Preferably the polyester or polyester segments are poly(lactic acid) (PLA), poly(glycolic acid) PGA, or poly(lactide-co-glycolide) (PLGA).

In some embodiments, the polymeric matrix is formed from a block copolymer containing one or more poly(alkylene oxide) segments, one or more aliphatic polyester segments, and optionally one or more photo-polymerizable groups. In these cases, the one or more poly(alkylene oxide) segments imbue the polymer with the necessary hydrophilicity, such that the resultant polymer matrix forms a suitable hydrogel, while the polyester segments provide a polymeric matrix with tunable hydrophobicity/hydrophilicity and/or the desired in vivo degradation characteristics.

The degradation rate of the polyester segments, and often the corresponding drug release rate, can be varied from days (in the case of pure PGA) to months (in the case of pure PLA), and may be readily manipulated by varying the ratio of PLA to PGA in the polyester segments. In addition, the poly(alkylene oxides), such as PEG, and aliphatic polyesters, such as PGA, PLA, and PLGA have been established as safe for use in humans; these materials have been used in human clinical applications, including drug delivery systems, for more than 30 years.

In certain embodiments, the polymeric matrix is formed from a tri-block copolymer containing a central poly(alkylene oxide) segment, adjoining aliphatic polyester segments attached to either end of the central poly(alkylene oxide) segment, and one or more photo-polymerizable groups. Preferably, the central poly(alkylene oxide) segment is PEG, and aliphatic polyesters segments are PGA, PLA, or PLGA.

Generally, the average molecular weight of the central poly(alkylene oxide) segment is greater than the average molecular weight of the adjoining polyester segments. In certain embodiments, the average molecular weight of the central poly(alkylene oxide) segment is at least three times greater than the average molecular weight of one of the adjoining polyester segments, more preferably at least five times greater than the average molecular weight of one of the adjoining polyester segments, most preferably at least ten times greater than the average molecular weight of one of the adjoining polyester segments.

In some cases, the central poly(alkylene oxide) segment possesses an average molecular weight ranging between 500 Da and 10,000 Da, more preferably between 1,000 Da and 7,000 Da, most preferably between 2,500 Da and 5,000 Da. In particular embodiments, average molecular weight of the central poly(alkylene oxide) segment is 4,000 Da. Typically, each adjoining polyester segment possesses an average molecular weight ranging between 100 Da and 3,500 Da, more preferably between 100 Da and 1,000 Da, most preferably between 100 Da and 500 Da.

Examples of natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the microparticles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of non-biodegradable polymers include ethylene vinyl acetate, poly(meth)acrylic acid, polyamides, copolymers and mixtures thereof.

The matrix can also be made of gel-type polymers, such as alginate, produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (for instance, 100-170 RPM) ionic hardening bath is positioned below the extruding device to catch the forming microdroplets. The microparticles are left to incubate in the bath for twenty to thirty minutes in order to allow sufficient time for gelation to occur. Microparticle size is controlled by using various size extruders or varying either the nitrogen gas or polymer solution flow rates. Chitosan microparticles can be prepared by dissolving the polymer in acidic solution and crosslinking it with tripolyphosphate. Carboxymethyl cellulose (CMC) microparticles can be prepared by dissolving the polymer in acid solution and precipitating the microparticle with lead ions. In the case of negatively charged polymers (e.g., alginate, CMC), positively charged ligands (e.g., polylysine, polyethyleneimine) of different molecular weights can be ionically attached.

Perhaps the most widely used are the aliphatic polyesters, specifically the hydrophobic poly(lactic acid) (PLA), more hydrophilic poly(glycolic acid) PGA and their copolymers, poly(lactide-co-glycolide) (PLGA). The degradation rate of these polymers, and often the corresponding drug release rate, can vary from days (PGA) to months (PLA) and is easily manipulated by varying the ratio of PLGA to PGA. Second, the physiologic compatibility of PLGA and its homopolymers PGA and PLA have been established for safe use in humans; these materials have a history of over 30 years in various human clinical applications including drug delivery systems. PLGA nanoparticles can be formulated in a variety of ways that improve drug pharmacokinetics and biodistribution to target tissue by either passive or active targeting. The microparticles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. Specifically the hydrophobic poly(lactic acid) (PLA), more hydrophilic poly (glycolic acid) PGA and their copolymers, poly(lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

Shell Components. Nanolipogels include a liposomal shell composed of one or more concentric lipid monolayers or lipid bilayers. The shell can further include one or more active agents, targeting molecules, or combinations thereof.

Nanolipogels include a liposomal shell composed of one or more concentric lipid monolayers or lipid bilayers. The composition of the liposomal shell may be varied to influence the release rate of one or more active agents in vivo. The lipids may also be covalently crosslinked, if desired, to alter in vivo drug release.

The lipid shell can be formed from a single lipid bilayer (unilamellar) or several concentric lipid bilayers (multilamellar). The lipid shell may be formed from a single lipid; however, in preferred embodiments, the lipid shell is formed from a combination of more than one lipid. The lipids can be neutral, anionic, or cationic at physiologic pH.

Suitable neutral and anionic lipids include sterols and lipids such as cholesterol, phospholipids, lysolipids, lysophospholipids, and sphingolipids. Neutral and anionic lipids include phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids, such as sphingomyelin; sphingoglycolipids (also known as 1-ceramidyl glucosides), such as ceramide galactopyranoside, gangliosides and cerebrosides; fatty acids, sterols containing a carboxylic acid group such as cholesterol or derivatives thereof; and 1,2-diacyl-sn-glycero-3-phosphoethanolamines, including 1,2-dioleoyl-sn-Glycero-3-phosphoethanolamine or 1,2-dioleolylglyceryl phosphatidylethanolamine (DOPE), 1,2-dihexadecylphosphoethanolamine (DHPE), 1,2-distearoylphosphatidylcholine (DSPC), 1,2-dipalmitoylphosphatidylcholine (DPPC), and 1,2-dimyristoylphosphatidylcholine (DMPC). Also suitable are natural (e.g., tissue derived L-.alpha.-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of these lipids.

Suitable cationic lipids include N-[1-(2,3-dioleoyloxy) propyl]-N,N,N-trimethyl ammonium salts, also referred to as TAP lipids, for example as a methylsulfate salt. Suitable TAP lipids include DOTAP (dioleoyl-), DMTAP (dimyristoyl-), DPTAP (dipalmitoyl-), and DSTAP (distearoyl-). Other suitable cationic lipids include dimethyldioctadecyl ammonium bromide (DDAB), 1,2-diacyloxy-3-trimethyl-ammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N- trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanam-inium trifluoro-acetate (DOSPA), .beta.-alanyl cholesterol, cetyltrimethylammonium bromide (CTAB), $diC_{14}$-amidine, N-tert-butyl-N'-tetradecyl-3-tetradecylamino-propionamidine, N-(alpha-trimethylammonio-acetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide, 1-[2-(acyloxy)ethyl]2-alkyl(alkenyl)-3-(2-hydroxyethyl)-imidazolinium chloride derivatives, such as 1-[2-(9(Z)-octadecenoyloxy)ethyl]-2-(8(Z)-heptadecenyl-3-(2-hydroxyethyl)-imidazolinium chloride (DOTIM) and 1-[2-(hexadecanoyloxy)ethyl]-2-pentadecyl-3-(2-hydroxyethyl) imidazolinium chloride (DPTIM), and 2,3-dialkyloxypropyl quaternary ammonium derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Other suitable lipids include PEGylated derivatives of the neutral, anionic, and cationic lipids described above. Incorporation of one or more PEGylated lipid derivatives into the lipid shell can result in a nanolipogel which displays polyethylene glycol chains on its surface. The resulting nanolipogels may possess increased stability and circulation time in vivo as compared to nanolipogels lacking PEG chains on their surfaces. Examples of suitable PEGylated lipids include distearoylphosphatidylethanlamine-polyethylene glycol (DSPE-PEG), including DSPE PEG (2000 MW) and DSPE PEG (5000 MW), dipalmitoyl-glycero-succinate polyethylene glycol (DPGS-PEG), stearyl-polyethylene glycol and cholesteryl-polyethylene glycol.

In certain embodiments, the lipid shell is formed from a combination of more than one lipid. In certain embodiments the lipid shell is formed from a mixture of at least three lipids. In particular embodiments, the lipid shell is formed from a mixture of phosphatidyl choline (PC), 1,2-distearoyl-sn-glycero-3-phosphoethanolamine-N-[amino(polyethylene glycol)-2000] (DSPE-PEG), and cholesterol.

In some embodiments, the lipid shell is formed from a mixture of one or more PEGylated phospholipids and one or more additional lipids or sterols. In certain instances, the molar ratio of the one or more PEGylated lipids to the one or more additional lipids or sterols ranges from 1:1 to 1:6, more preferably from 1:2 to 1:6, most preferably from 1:3 to 1:5. In particular embodiments, the molar ratio of the one or more PEGylated lipids to the one or more additional lipids or sterols is 1:4.

In some embodiments, the lipid shell is formed from a mixture of one or more phospholipids and one or more additional lipids or sterols. In certain instances, the molar ratio of the one or more phospholipids to the one or more additional lipids or sterols ranges from 1:1 to 6:1, more preferably from 2:1 to 6:1, most preferably from 3:1 to 5:1. In particular embodiments, the molar ratio of the one or more phospholipids to the one or more additional lipids or sterols is 4:1.

In preferred embodiments, the lipid shell is formed from a mixture of a phospholipid, such as phosphatidyl choline (PC), a PEGylated phospholipid, such as 1,2-distearoyl-sn-glycero-3-phosphoethanolamine-N-[amino(polyethylene glycol)-2000] (DSPE-PEG), and cholesterol. In particular embodiments, the lipid shell is formed from a mixture of phosphatidyl choline, 1,2-distearoyl-sn-glycero-3-phosphoethanolamine-N-[amino(polyethylene glycol)-2000] (DSPE-PEG), and cholesterol in a 3:1:1 molar ratio.

Polymeric Particles. The delivery vehicle can also be a polymeric particle, for example a micro- or a nanoparticle. The particles can be biodegradable or non-biodegradable. Exemplary polymers that can be used to manufacture polymeric particles are discussed above with respect to the polymeric matrix component of nanolipogels.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof. In preferred embodiments, the particles are composed of one or more polyesters.

For example, particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(.epsilon.-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker. Alginate polymers may also be used.

In some embodiments, the particles are composed of PLGA. PLGA is a safe, FDA approved polymer. PLGA particles are advantageous because they can protect the active agent (i.e., the encapsulant), promote prolonged release, and are amenable to the addition of targeting moieties.

The particles can contain one or more polymer conjugates containing end-to-end linkages between the polymer and a targeting moiety, detectable label, or other active agent. For example, a modified polymer can be a PLGA-PEG-phosphonate. In another example, the particle is modified to include an avidin moiety and a biotinylated targeting moiety, detectable label, or other active agent can be coupled thereto.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the particles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of non-biodegradable polymers include ethylene vinyl acetate, poly(meth)acrylic acid, polyamides, copolymers and mixtures thereof.

Nanolipogels. A nanolipogel is a nanoparticle that combines the advantages of both liposomes and polymer-based particles for sustained delivery of nucleic acids, proteins and/or small molecules. The nanolipogel can be in the form of spheres, discs, rods or other geometries with different aspect ratios. The nanosphere can be larger, i.e., microparticles. The nanolipogel is typically formed of synthetic or natural polymers capable of encapsulating agents by remote loading and tunable in properties so as to facilitate different rates of release. Release rates are modulated by varying the polymer to lipid ratio from 0.05 to 5.0, more preferably from 0.5 to 1.5.

Nanolipogels are designed to be loaded with agents either prior to, during or after formation and subsequently function as controlled-release vehicles for the agents. The nanolipogel can be loaded with more than one agent such that controlled release of the multiplicity of agents is subsequently achieved.

The nanolipogel is loaded with one or more therapeutic agents and/or adjuvants during formation and/or following formation by the process of rehydration of the nanolipogel in the presence of the agents. For example, the nanolipogel is loaded with a molecule that serves as an adjuvant and the nanolipogel thereafter incorporates one or more anti-cancer agents after formation, for the delivery and release of adjuvant together with the anti-cancer agent(s).

Polymeric Nanoparticles

Emulsion Method. In some embodiments, the polymeric nanoparticle is prepared using an emulsion solvent evaporation method. For example, a polymeric material is dissolved in a water immiscible organic solvent and mixed with a drug solution or a combination of drug solutions. The water immiscible organic solvent can be one or more of the following: chloroform, dichloromethane, and acyl acetate. The drug can be dissolved in one or more of the following: acetone, ethanol, methanol, isopropyl alcohol, acetonitrile and dimethyl sulfoxide (DMSO). An aqueous solution is then added into the resulting mixture solution to yield emulsion solution by emulsification. The emulsification technique can be probe sonication or homogenization through a homogenizer. The peptides or fluorophores or drugs may be associated with the surface of, encapsulated within, surrounded by, and/or distributed throughout, the polymeric matrix of the particle.

Nanoprecipitation Method. In another embodiment, the polymeric nanoparticles are prepared using nanoprecipitation methods or microfluidic devices. A polymeric material is mixed with a drug or drug combinations in a water miscible organic solvent. The resulting mixture solution is then added to an aqueous solution to yield a nanoparticle solution.

Exemplary Methods of Preparation. Particles can be fabricated from different polymers using a variety of methods that and can be selected based on criteria including the polymeric composition of the particle, the agent(s) being loaded into or associated with the particle according to method that are known in the art. Exemplary methods are provided below.

Solvent Evaporation. In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid particles. The resulting particles are washed with water and dried overnight in a lyophilizer. Particles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

Hot Melt Microencapsulation. In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting particles are washed by decantation with petroleum ether to give a free-flowing powder. Particles with sizes between 0.5 to 1000 microns are obtained with this method. The external surfaces of spheres prepared with this technique are usually smooth and dense. This procedure is used to prepare particles made of polyesters and polyanhydrides. However, this method is limited to polymers with molecular weights between 1,000-50,000.

Solvent Removal. This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make particles from polymers with high melting points and different molecular weights. Particles that range between 1-300 microns can be obtained by this procedure. The external morphology of spheres produced with this technique is highly dependent on the type of polymer used.

Spray-Drying. In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=-24° C., outlet temperature=13-15° C., aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

Hydrogel Particles. Particles made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (for instance, 100-170 RPM) ionic hardening bath is positioned below the extruding device to catch the forming microdroplets. The particles are left to incubate in the bath for twenty to thirty minutes in order to allow sufficient time for gelation to occur. Particle size is controlled by using various size extruders or varying either the nitrogen gas or polymer solution flow rates. Chitosan particles can be prepared by dissolving the polymer in acidic solution and crosslinking it with tripolyphosphate. Carboxymethyl cellulose (CMC) particles can be prepared by dissolving the polymer in acid solution and precipitating the particle with lead ions. In the case of negatively charged polymers (e.g., alginate, CMC), positively charged ligands (e.g., polylysine, polyethyleneimine) of different molecular weights can be ionically attached.

Other Delivery Vehicles

In some embodiments, the delivery vehicles are liposomes or lipid nanoparticles. Liposomes are typically spherical vesicles composed of a lamellar phase lipid bilayer. The liposomes can be, for example, multilamellar vesicles (MLV), small unilamellar liposome vesicles (SUV), large unilamellar vesicles (LUV), or cochleate vesicles. Liposomes, micelles, and other lipid-based delivery vehicles useful for preparation of the disclosed nanoparticulate compositions are known in the art. See, for example, Torchilin et al. (*Adv Drug Delivery Rev,* 58(14):1532-55, 2006). It is anticipated that a wide variety of liposomes and exosomes may be used with the present invention. Liposomes may include N-[1-(2,3-Dioleoyloxy)propyl]-N,N,N-trimethylammonium methyl-sulfate (DOTAP) or Lipofectamine™. In some embodiments, a delivery system involving chitosan may be used as described, e.g., in Lu et al. (*Cancer Cell,* 18:185-197, 2010). In some embodiments, a nanovector may be used to deliver a miRNA to a subject; nanovectors are described, e.g., in Pramanik et al. (*Mol Cancer Ther,* 10:1470-1480, 2011).

The delivery vehicle can also be silica particles. Suitable silica particles useful for preparation of the disclosed nanoparticulate compositions are also known in the art. See, for example, Barbe et al. (*Adv Materials,* 16(21):1959-1966, 2004), Ngamcherdtrakul et al. (*Adv Func Materials,* 25: 2646-2659, 2015) and Argyo et al. (*Chem. Mater.,* 26(1): 435-451, 2014). For example, in some embodiments, a silicone nanoparticle (e.g., as described in Bharali et al. PNAS, 102(32): 11539-11544, 2005) may be used to deliver an adjuvant and another therapeutically active agent to a cell. Solubility of silica or silicon in the body provides the ability for time-release of the agents that the particles carry. In addition, biodegradable polymers or bioreducible cross-linking agents can be used to modify the silica or silicon particles to provide the time-release ability.

(VI) PHARMACEUTICAL COMPOSITIONS AND ADMINISTRATION FORMULATIONS

Provided herein are compositions for use in treating cancer, precancer, and other proliferative disease. The compositions include at least two active components/agents, one of which is a therapeutically active agent that (1) causes tumor antigen release and/or (2) modulates an immunosuppressive tumor microenvironment; and another of which is an adjuvant. As described herein, the active agents are delivered in/associated with a delivery vehicle, such as a liposome, an organic or inorganic (nano- or micro-) particle, and so forth.

The compositions can be provided to the cells either directly, such as by contacting it with the cell, or indirectly, such as through the action of any biological process. For example, the compositions can be formulated in a physiologically acceptable carrier or vehicle and injected into a tissue or fluid surrounding the cell. The compositions can cross the cell membrane by simple diffusion, endocytosis, or by any active or passive transport mechanism.

When formulated in a pharmaceutical composition, a therapeutic compound (such as delivery system coupled with at least one therapeutic agent and at least one adjuvant) can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human or veterinary subject.

The term "pharmaceutically acceptable derivative" as used herein means any pharmaceutically acceptable salt, solvate or prodrug, e.g. ester, of the desired active agent, which upon administration to the recipient is capable of providing (directly or indirectly) the desired active agent, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice. Pharmaceutically acceptable derivatives include salts, solvates, esters, carbamates, and phosphate esters.

While it is possible to use a composition for therapy as is, it may be preferable to administer it in a pharmaceutical formulation, e.g., in admixture with a suitable pharmaceutical excipient, diluent or carrier selected with regard to the intended route of administration and standard pharmaceutical practice. Accordingly, in one aspect, pharmaceutical composition or formulation includes at least one active composition, or a pharmaceutically acceptable derivative thereof, in association with a pharmaceutically acceptable excipient, diluent and/or carrier. The excipient, diluent and/or carrier is "acceptable" in the sense of being compatible with the other ingredient(s) of the formulation and not significantly deleterious to the recipient thereof.

Any composition formulation disclosed herein can advantageously include any other pharmaceutically acceptable carriers which include those that do not produce significantly adverse, allergic, or other untoward reactions that outweigh the benefit of administration, whether for research, prophylactic and/or therapeutic treatments. Exemplary pharmaceutically acceptable excipients, diluents, and carriers for therapeutic use are well known in the pharmaceutical art, and are described, for example, in Remington: The Science and Practice of Pharmacy. Lippincott Williams & Wilkins (A. R., Gennaro edit. 2005), and in Remington's Pharmaceutical Sciences, 18th Ed. Mack Printing Company, 1990. Moreover, formulations can be prepared to meet sterility, pyrogenicity, general safety and purity standards as required by United States FDA Office of Biological Standards and/or other relevant foreign regulatory agencies. The pharmaceutical excipient(s), diluent(s), and carrier(s) can be selected with regard to the intended route of administration and standard pharmaceutical practice.

Such pharmaceutical formulations may be presented for use in a conventional manner with the aid of one or more suitable excipients, diluents, and carriers. Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol, or mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers, or polysaccharides.

A "therapeutically effective amount" or "therapeutically effective dose" means the amount of a compound that, when administered to a subject for treating a state, disorder or condition, is sufficient to effect such state, disorder, or condition. The "therapeutically effective amount" will vary depending on the compound, the disease and its severity and the age, weight, physical condition and responsiveness of the mammal to be treated. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). In certain cases, "therapeutically effective amount" is used to mean an amount or dose sufficient to modulate, e.g., increase or decrease a desired activity e.g., by 10%, by 50%, or by 90%. Generally, a therapeutically effective amount is sufficient to cause an improvement in a clinically significant condition in the host following a therapeutic regimen involving one or more therapeutic agents. The concentration or amount of the active ingredient depends on the desired dosage and administration regimen, as discussed herein.

The actual dose amount administered to a particular subject can be determined by a physician, veterinarian, or researcher taking into account parameters such as physical, physiological and psychological factors including target, body weight, stage of cancer, the type of cancer, previous or concurrent therapeutic interventions, idiopathy of the subject, and route of administration.

Amounts effective for this use will depend on the severity of the disease and its location, particularly when a metastatic site is implicated, and the weight and general state of the patient being treated. Generally dosages range from 0.01 mg/kg to 100 mg/kg host body weight of immunotherapeutic construct per day, with dosages of from 0.1 mg/kg to 10 mg/kg per day being more commonly used, and for instance dosages of 3-7 mg/kg. Maintenance dosages over a prolonged period of time may be adjusted as necessary. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The selected dosage may be influenced by the desired therapeutic effect, the route of administration, the duration of the treatment desired, and the specific immunotherapeutic complex being employed. Generally, immunotherapeutic construct can be administered in a range of 0.001 mg/kg to 100 mg/kg per administration (e.g., daily; or 2, 3, 4, 5 or more times weekly; or 2, 3, 4, 5 or more times a month, etc., as discussed in more detail below). The route of administration can be a consideration in determining dosage as well. For example, in a particular embodiment, a immunotherapeutic construct is administered in a range of 0.01 mg/kg to 100 mg/kg (e.g., daily; or 2, 3, 4, 5 or more times weekly; or 2, 3, 4, 5 or more times a month, etc.) by intravenous or interpretational routes, or in a range of 0.0001 mg/kg to 1 mg/kg (e.g., daily; or 2, 3, 4, 5 or more times weekly; or 2, 3, 4, 5 or more times a month, etc.) for a subcutaneous route (e.g., local injection into or adjacent to a tumor or into the TME). More exemplary dosage are discussed below.

Suitable dosages may range from 0.01 mg/kg to 100 mg/kg of body weight per day, week, or month. Exemplary doses can include 0.05 mg/kg to 10.0 mg/kg of the active compounds (immunotherapeutic constructs) disclosed herein. The total daily dose can be 0.05 mg/kg to 30.0 mg/kg of an agent administered to a subject one to three times a day, including administration of total daily doses of 0.05-3.0, 0.1-3.0, 0.5-3.0, 1.0-3.0, 1.5-3.0, 2.0-3.0, 2.5-3.0, and 0.5-3.0 mg/kg/day of administration forms of a drug using 60-minute oral, intravenous or other dosing. In one particular example, doses can be administered QD or BID to a subject with, e.g., total daily doses of 1.5 mg/kg, 3.0 mg/kg, 4.0 mg/kg, 5.0 mg/kg, or 7.5 mg/kg of a composition with up to 92-98% wt/v of the compounds disclosed herein.

Additional useful doses can often range from 0.1 to 5 µg/kg or from 0.5 to 1 µg/kg. In other examples, a dose can include 1 µg/kg, 10 µg/kg, 20 µg/kg, 40 µg/kg, 80 µg/kg, 200 µg/kg, 0.1 to 5 mg/kg or from 0.5 to 1 mg/kg. In other examples, a dose can include 1 mg/kg, 10 mg/kg, 20 mg/kg, 40 mg/kg, 80 mg/kg, 200 mg/kg, 400 mg/kg, 450 mg/kg, or more.

Therapeutic materials of the present disclosure may be employed in serious disease states, that is, life-threatening or potentially life-threatening situations. In such cases, it is possible and may be felt desirable by the treating physician to administer substantial excesses of these compositions.

As will be appreciated by those of skill in the art, specific dosages will be influenced by the pharmacokinetics of the active compound. For administration, therapeutically effective amounts (also referred to herein as doses) can be initially estimated based on results from in vitro assays and/or animal model studies. Such information can be used to more accurately determine useful doses in subjects of interest. Useful pre-clinical tests include pharmacodynamic analyses, toxicity analyses, and so forth.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly).

The effective amounts of compounds containing active agents include doses that partially or completely achieve the desired therapeutic, prophylactic, and/or biological effect. The actual amount effective for a particular application depends on the condition being treated and the route of administration. The effective amount for use in humans can be determined from animal models. For example, a dose for humans can be formulated to achieve local (e.g., intratumoral) or circulating levels that have been found to be effective in animals.

Compositions can be administered with one or more anesthetics including ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and/or phenazopyridine.

In particular embodiments that include treating or preventing a cancer (including for instance a cancer metastasis), the compositions disclosed herein can be used in conjunction with other cancer treatments, such as chemotherapeutic agents, radiation therapy, and/or immunotherapy. The compositions described herein can be administered simultaneously with or sequentially with another treatment within a selected time window, such as within 10 minutes, 1 hour, 3 hour, 10 hour, 15 hour, 24 hour, or 48 hour time windows or when the complementary treatment is within a clinically-relevant therapeutic window.

Pharmaceutical compositions can be for administration by parenteral (intramuscular, intraperitoneal, intravenous (IV) or subcutaneous injection), by instillation, or in a depo, formulated in dosage forms appropriate for each route of administration.

In some embodiments, the compositions are administered systemically, for example, by intravenous or intraperitoneal administration, in an amount effective for delivery of the compositions to targeted cells. Other routes include instillation or mucosal.

In certain embodiments, the compositions are administered locally, for example, by injection directly into a site to be treated. In some embodiments, the compositions are injected or otherwise administered directly to one or more tumors or diseased tissues. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps or incorporating the compositions into polymeric implants which can effect a sustained release of the compositions to the immediate area of the implant.

By way of example, in certain embodiments the immunotherapeutic constructs are given locally, for instance to readily accessible tumors such as melanoma, head and neck cancer, breast cancer, and lymphoma; or systemically for other cancers such as lung cancer, liver cancer, pancreatic cancer, prostate cancer, and metastatic cancers.

Thus, the therapeutic compositions described herein can be administered (on their own or as part of a combination therapy) by a variety of routes, including any convenient way for use in human or veterinary medicine. A therapeutically effective amount of the desired active agent(s) can be formulated in a pharmaceutical composition to be introduced parenterally, transmucosally (e.g., orally, nasally, or rectally), or transdermally. In some embodiments, administration is parenteral, for instance, via intravenous injection, or intra-arteriole, intramuscular, intradermal, subcutaneous, intraperitoneal, intraventricular, and intracranial administration. The administered may be as a bolus or by continuous infusion over a period of time, by intramuscular, intraperitoneal, intracerobrospinal, subcutaneous, intra-articular, intrasynovial, intrathecal, oral, topical, or inhalation routes. In certain embodiments, implanted systems that allow local delivery to non-cutaneous tumors can also be used to deliver the herein-provided immunotherapeutic construct, e.g., hepatic artery infusion pump, convection enhanced delivery. In certain embodiments, for instance those involved in treatment of inflammatory conditions that impact joints, the pharmaceutical composition may be administered directly to the synovium, synovial fluid or joint capsule by injection preferably with a syringe. Administration may be local or systemic; the choice may be influenced by the condition being treated, as well as the active agent(s) and compositions being administered.

For injection, compositions can be made as aqueous solutions, such as in buffers such as Hanks' solution, Ringer's solution, or physiological saline. The solutions can contain formulating agents such as suspending, stabilizing and/or dispersing agents. Alternatively, the composition can be in lyophilized and/or powder form for constitution with a suitable vehicle, e.g., sterile pyrogen-free water, before use.

Compositions including an immunotherapeutic construct may be administered in an aqueous solution, by parenteral injection. The injectable formulation can be in the form of a suspension or emulsion, and optionally includes pharmaceutically acceptable diluents, preservatives, solubilizers, emulsifiers, adjuvants and/or carriers. Such injectable compositions can include diluents such as sterile water, buffered saline of various buffer content (e.g., Tris-HCl, acetate, phosphate), pH and ionic strength; and optionally, additives such as detergents and solubilizing agents (e.g., TWEEN™ 20, TWEEN™ 80 also referred to as polysorbate 20 or 80), anti-oxidants (e.g., ascorbic acid, sodium metabisulfite), and preservatives (e.g., Thimerosal, benzyl alcohol). Examples of non-aqueous solvents or vehicles are propylene glycol, polyethylene glycol, vegetable oils, such as olive oil and corn oil, gelatin, and injectable organic esters such as ethyl oleate. The formulations for injection may be lyophilized and resuspended, for instance immediately before use. The injectable formulation may be sterilized by, for example, filtration through a bacteria retaining filter, by incorporating sterilizing agents into the compositions, by irradiating the compositions, or by heating the compositions.

In other embodiments, immunotherapeutic construct-including compositions are applied topically or by instillation. Topical administration can include application to the lungs, nasal, oral (sublingual, buccal), vaginal, or rectal mucosa.

These methods of administration can be made effective by formulating the shell or coating of the delivery vehicle with mucosal transport element(s). Compositions can be delivered to the lungs while inhaling and traverse across the lung epithelial lining to the blood stream when delivered either as an aerosol or spray dried particles having an aerodynamic diameter of less than 5 microns.

A wide range of mechanical devices designed for pulmonary delivery of therapeutic products can be used, including but not limited to nebulizers, metered dose inhalers, and powder inhalers, all of which are familiar to those skilled in the art.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations can include penetration enhancers. Chemical enhancers and physical methods including electroporation and microneedles can work in conjunction with this method.

A microneedle (MN) is a micron-sized needle with a height of 10-2000 μm and a width of 10-50 μm, which can penetrate through the epidermis layer to dermal tissue directly with minimal or no pain (Hao et al., *J Biomed Nanotechnol,* 13(12):1581-1597, 2017). Several types of microneedles can be used. In some embodiments, metal-based or plastic microneedle rollers can be used to physically disrupt skin surface to enhance penetration of the applied topical agents (immunotherapeutic construct in this case). In some embodiments, degradable and dissolvable microneedles can contain immunotherapeutic constructs. Upon administration to skin, microneedles can dissolve and release the construct deep in layers of skin. In some embodiments, non-degradable microneedles may be coated with immunotherapeutic constructs, such that they deliver the coated construct deep in skin layers. Microneedles can be fabricated from many classes of materials, including but not limited to, polymer, saccharides, polysaccharides, peptide, protein, metals, inorganic compound, and so forth (Ye et al., *Adv Drug Deliv Rev,* 127: 106-118, 2018). All materials and fabrication methods known in the art for microneedle technology is applicable to enhance delivery of this immunotherapeutic construct.

Any device that facilitates systemic or localized delivery of therapeutics is also applicable to our immunotherapeutic construct. For example, hepatic arterial infusion (HAI) pump, which is an implanted chemotherapy device that delivers high concentrations of cytotoxic agents directly to liver metastases with minimal systemic toxicities (Cohen et al., *The Oncologist,* 8(6): 553-566, 2003), can also be utilized to deliver the herein described immunotherapeutic constructs.

(VII) EXEMPLARY METHODS OF USE

With the provision herein of immunotherapeutic constructs that include at least one adjuvant and at least one therapeutically active agent(s) capable of inducing antigen release and/or modulating an immunosuppressive environment (such as a tumor microenvironment), there are now enabled methods of treating and/or preventing hyperproliferative diseases, disorders, or conditions, including cancer, symptoms of cancer, cancer progression (including from precancer to cancer), and cancer metastasis. Specific examples of hyperproliferative diseases, disorders, or conditions include cancer. In some embodiments, the cancer may suppress the immune system of the subject or individual with the cancer. In some embodiments, the immunotherapeutic constructs as provided herein can suppress or reverse cancer-mediated immune suppression and allow for immune recognition and clearance of the malignancy.

As used herein, the term "treatment" or "treating" refers to any improvement of the cancer that occurs in a treated subject compared to an untreated subject. Such an improvement can be a prevention of a worsening or progression of the cancer (e.g., improved progression-free survival). Moreover, such an improvement may also be a reduction or cure of the cancer or its accompanying symptoms (e.g., reduction in tumor volume, partial remission, complete remission (e.g., for 6 months, 1 year, 2 years, 3 years, 4 years, or 5 years or more), prevention of cancer recurrence or relapse, reduction of metastasis, or reduction of number of tumors or lesions). It will be understood that a treatment may not be successful for 100% of the subjects to be treated, but successful in certain individual compared to other treatments the individual has received as determined by the person skilled in the art (e.g., physicians). As used herein, the term "preventing" refers to avoiding the onset of cancer as used herein or its accompanying syndromes. It will be understood that prevention refers to avoiding the onset of cancer within a certain time window in the future. Said time window shall, preferably, start upon administration of a compound in the sense of the invention and lasts for at least 1 month, at least 6 months, at least 9 months, at least 1 year, at least 2 years, at least 5 years, at least 10 years or even for the remaining physiological life span of a subject. It will be understood that a prevention may not be successful for 100% of the subjects to be treated, but successful in certain individual compared to other treatments the individual has received as determined by the person skilled in the art (e.g., physicians). Prevention may also be in the context of a recurrence of cancer after remission, e.g., as measured by a reduction in probability for recurrence in a population. Prevention also refers to elimination of cancer cells anywhere in the body that could otherwise regrow and exhibit positive prognosis and disease symptoms at later dates.

The disclosed compositions can be used to treat benign or malignant cancers, and tumors thereof. The treatment can directly target and kill cancer cells, indirectly target the cancer cells by increasing an immune response against the cancer cells; or a combination thereof.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The disclosed compositions can delay or inhibit the growth of a tumor in a subject, reduce the growth or size of the tumor or eliminate it altogether, inhibit or reduce metastasis of the tumor, and/or inhibit or reduce symptoms associated with tumor development or growth. For example, in some embodiments, the compositions reduce tumor burden in the subject or slow or prevent tumor growth over time.

Malignant tumors may be classified according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, vascular cancers such as multiple myeloma, as well as solid cancers, including adenocarcinomas and sarcomas, of bone, bladder, brain, breast, cervix, colon, rectum, esophagus, kidney, liver, lung, nasopharynx, pancreas, prostate, skin, stomach, and uterus. In some embodiments, the disclosed compositions are used to treat multiple cancer types concurrently. The compositions can also be used to treat metastases or tumors at multiple locations.

Administration is not limited to the treatment of an existing tumor but can also be used to prevent or lower the risk of developing such diseases in an individual, i.e., for prophylactic use and to reduce spread of cancer, for instance through metastasis. Potential candidates for prophylactic vaccination include individuals with a high risk of developing cancer, i.e., with a personal or familial history of certain types of cancer.

In one embodiment, an immunotherapeutic construct including an adjuvant agent CpG, siRNA against BRAFV600E to kill melanoma and precursor cells (melanocytes in moles) leading to antigen release, and siRNA against STAT3 to mitigate the immunosuppressive environment, can be used to create adaptive immunity in subjects with high-risk of development melanoma and melanoma patients. The immunotherapeutic construct will not only prevent and treat melanoma, but will also provide the protection from future recurrence or relapse after surgery for later stage melanoma patients. siRNA against other genes along with targeting agents may be incorporated on or in the nanoparticle/construct.

Various therapeutic modalities, including systemic immunotherapy, chemotherapy, and biochemotherapy, have been tested in the adjuvant setting, but they also pose systemic toxicity and side effects that can be overcome with localized treatment with the herein-described immunotherapeutic constructs. In certain embodiments, immunotherapeutic constructs (e.g., containing CpG or another adjuvant, along with a chemodrug, a targeted therapy, and/or siRNA against STAT3) can be used to treat breast cancer in adjuvant settings by intratumoral injection before surgical removal of the primary breast tumors, which will prevent recurrence and metastasis of the cancer without the toxicity of the systemic drugs.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g., triple negative, ER positive, ER negative, chemotherapy resistant, Herceptin® resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g. head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer. The term "precancer", as used herein, refers to a condition or growth that precedes or develops into a cancer. The term "cancer metastasis", as used herein, refers to the spread of cancer cells or a tumor from one organ or part of the body to another organ or part of the body.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairycell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

(VIII) KITS

Active component(s), including particularly at least one described therapeutic construct (including a delivery vehicle containing or associated with at least one therapeutic agent and at least one adjuvant), can be provided as kits. Kits can include one or more containers including (containing) one or more or more compounds or complexes (e.g., anti-cancer agents) as described herein, optionally along with one or more additional agents for use in therapy. For instance, some kits will include an amount of at least one additional anti-cancer composition, or an amount of at least one additional anti-inflammatory agent, or both.

Any active component in a kit may be provided in premeasured dosages, though this is not required; and it is anticipated that certain kits will include more than one dose.

Kits can also include a notice in the form prescribed by a governmental agency regulating the manufacture, use, or sale of pharmaceuticals or biological products, which notice reflects approval by the agency of manufacture, use, or sale for human administration. The notice may state that the provided active ingredients can be administered to a subject. The kits can include further instructions for using the kit, for example, instructions regarding administration; proper disposal of related waste; and the like. The instructions can be in the form of printed instructions provided within the kit or the instructions can be printed on a portion of the kit itself. Instructions may be in the form of a sheet, pamphlet, brochure, CD-ROM, or computer-readable device, or can provide directions to instructions at a remote location, such as a website. In particular embodiments, kits can also include some or all of the necessary medical supplies needed to use the kit effectively, such as applicators, ampules, sponges, sterile adhesive strips, Chloraprep, gloves, and the like. Variations in contents of any of the kits described herein can be made. The instructions of the kit will direct use of the active ingredient(s) included in that kit to effectuate a clinical and/or therapeutic use described herein.

Suitable methods, materials, and examples used in the practice and/or testing of embodiments of the disclosed invention are described herein. Such methods and materials are illustrative only and are not intended to be limiting. Other methods, materials, and examples similar or equivalent to those described herein can be used.

The Exemplary Embodiments and Example(s) below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

(IX) EXEMPLARY EMBODIMENTS

1. An immunotherapeutic construct including: a delivery system; at least one therapeutic agent, e.g., loaded into, attached to the surface of, coupled to, enclosed within, or contained within the delivery system, where the therapeutic agent causes tumor antigen release and/or modulates an immunosuppressive tumor microenvironment; and at least one adjuvant compound, e.g., attached to the surface of, coupled to, enclosed within, or contained within the delivery system, in which the immunotherapeutic construct does not include a tumor-specific antigen or ovalbumin.
2. The immunotherapeutic construct of embodiment 1, wherein the delivery system includes a liposome, a lipid-based particle, a polymeric particle, an inorganic particle, an inorganic particle coated with polymer or lipid, or a hybrid thereof.
3. The immunotherapeutic construct of embodiment 2, wherein the delivery vehicle is a liposome, a lipid-based particle, a polymeric particle, an inorganic particle, or an inorganic particle coated with polymer or lipid.
4. The immunotherapeutic construct of embodiment 3, wherein the delivery vehicle is an inorganic particle and includes one or more of mesoporous silica, gold, aluminum, iron oxide, calcium phosphate, or an antioxidant particle.
5. The immunotherapeutic construct of embodiment 4, wherein the inorganic particle includes an antioxidant particle including cerium oxide.
6. The immunotherapeutic construct of embodiment 4, wherein the delivery vehicle comprises a mesoporous silica particle.
7. The immunotherapeutic construct of embodiment 1, wherein the delivery vehicle includes one or more of fullerenes, endohedral metallofullerenes, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, silicon, silica and polymer micro- and nano-spheres, silica-shells, biodegradable PLGA micro- and nano-spheres, gold particles, cerium oxide particles, zinc oxide particles, silver particles, aluminum particles, carbon particles, iron particles, iron oxide particles, calcium phosphate, adjuvant particles, and/or modified micelles.
8. The immunotherapeutic construct of any one of embodiments 1-7, wherein the delivery vehicle is a polymeric particle including one or more of PLGA, PLL, polyarginine, PEG, PEI, or chitosan.
9. The immunotherapeutic construct of any one of embodiments 1-8, which is a nanoparticle with a hydrodynamic size of 5 nm to 999 nm.
10. The immunotherapeutic construct of any one of embodiments 1-8, which is microparticle with a hydrodynamic size of 1 micron to 1000 microns.
11. The immunotherapeutic construct of embodiment 6, wherein the delivery vehicle comprises a mesoporous silica nanoparticle having a size of about 5-200 nm.
12. The immunotherapeutic construct of embodiment 11, wherein the mesoporous silica nanoparticle is coated with cross-linked polyethyleneimine and polyethylene glycol.
13. The immunotherapeutic construct of any one of embodiments 1-12, wherein the at least one therapeutic agent comprises a siRNA, a miRNA, an antisense oligonucleotide, a mRNA, a DNA, a sgRNA (CRISPR-cas9 element), an oligonucleotide, a polynucleotide, a peptide, a protein, a chemotherapy drug, a toxin, an antioxidant, a small molecule inhibitor, an antibody, or a radio-therapeutic agent.
14. The immunotherapeutic construct of embodiment 13, wherein the at least one therapeutic agent comprises a siRNA, a miRNA, an antisense oligonucleotide, a mRNA, or a DNA.
15. The immunotherapeutic construct of embodiment 14, wherein the at least one therapeutic agent comprises a siRNA.
16. The immunotherapeutic construct of embodiment 15, wherein the at least one therapeutic agent comprises a siRNA that inhibits expression or an activity of STAT3, CD39, CD73, TGF-$\beta$, PD-L1, PD1, CTLA4, MIF, PLK1, HIF, NOX1-4, HER2, EGFR, BCL2, AKT1, HIF1-alpha, NOX1-4, AR, MYC, BRAF, BRAF V600E, or MTDH.
17. The immunotherapeutic construct of embodiment 15 or 16, wherein the at least one therapeutic agent comprises a siRNA that inhibits expression or an activity of STAT3.
18. The immunotherapeutic construct of any one of embodiments 15-17, wherein the at least one therapeutic agent comprises a siRNA that inhibits expression of an activity of HER2.
19. The immunotherapeutic construct of any one of embodiments 1-12, wherein the at least one therapeutic agent inhibits expression or an activity of STAT3, CD39, CD73, TGF-$\beta$, PD-L1, PD1, CTLA4, MIF, PLK1, HIF, NOX1-4, HER2, EGFR, BCL2, AKT1, HIF1-alpha, NOX1-4, AR, MYC, or MTDH.
20. The immunotherapeutic construct of any one of embodiments 1-19, wherein the therapeutic agent is an anticancer agent including one or more of an antibiotic, a plant alkaloid, a PLK1 inhibitor, a mitotic kinase inhibitor, an immune checkpoint inhibitor, a platinum-based chemotherapeutic agent, a HER2 small molecule inhibitor, or a HER2-specific antibody.
21. The immunotherapeutic construct of embodiment 20, wherein therapeutic agent is a checkpoint inhibitor, and the checkpoint inhibitor is an antibody against PD-L1, PD1, or CTLA4.
22. The immunotherapeutic construct of embodiment 21, wherein the checkpoint inhibitor is an antibody against PD-L1.
23. The immunotherapeutic construct of any one of embodiments 1-22, wherein the at least one therapeutic agent comprises a PLK1 inhibitor.
24. The immunotherapeutic construct of embodiment 23, wherein the PLK1 inhibitor is volasertib.

25. The immunotherapeutic construct of any one of embodiments 1-24, wherein the at least one therapeutic agent comprises one or more of docetaxel, mitoxantrone, or cabazitaxel.
26. The immunotherapeutic construct of any one of embodiments 1-25, wherein the at least one therapeutic agent comprises an anti-EGFR antibody,
27. The immunotherapeutic construct of embodiment 26, wherein the anti-EGFR antibody is cetuximab.
28. The immunotherapeutic construct of any one of embodiments 1-25, wherein the at least one therapeutic agent comprises an anti-HER2 antibody.
29. The immunotherapeutic construct of embodiment 28, wherein the anti-HER2 antibody is trastuzumab.
30. The immunotherapeutic construct of any one of embodiments 1-29, wherein the adjuvant has immunostimulatory activity and comprises one or more of a CpG oligonucleotide, a DNA TLR agonist containing a CpG sequence, a non-CpG DNA TLR agonist, an RNA TLR agonist, an aluminum salt, an anti-CD40 antibody, a fusion protein, a cytokine, a small molecule TLR agonist, an oil- or surfactant-based adjuvant, a lipopolysaccharide, a plant extract, or a derivative thereof.
31. The immunotherapeutic construct of any one of embodiments 1-30, wherein the adjuvant compound includes a CpG oligonucleotide, imiquimod, resiquimod, gardiquimod, poly I:C, poly ICLC, dSLIM, or EnanDIM.
32. The immunotherapeutic construct of any one of embodiments 1-31, wherein the adjuvant compound comprises a CpG oligonucleotide.
33. A composition including: the immunotherapeutic construct of any one of embodiments 1-32 and at least one pharmaceutically acceptable carrier, excipient, diluent, or mixture thereof.
34. A method of treating cancer including administering to a subject with cancer an effective amount of the immunotherapeutic construct of any one of embodiments 1-32, or the composition of embodiment 33, to reduce one or more symptoms of the cancer.
35. The method of embodiment 34, wherein the subject is a mammal.
36. The method of embodiment 35, wherein the mammal is a human.
37. A method of treating a cell exhibiting symptoms of cancer including contacting the cell with a therapeutically effective amount of the immunotherapeutic construct of any one of embodiments 1-32, or the composition of embodiment 33.
38. A method of treating a cell obtained from a subject exhibiting symptoms of cancer, including contacting the cell with a therapeutically effective amount of the immunotherapeutic construct of any one of embodiments 1-32, or the composition of embodiment 33.
39. A method, comprising contacting a cell ex vivo with a therapeutically effective amount of the immunotherapeutic construct of any one of embodiments 1-32, or the composition of embodiment 33.
40. The method of embodiment 38 or 39, wherein the cell is a cancer cell.
41. The method of embodiment 38 or 39, wherein the cell is not a cancer cell.
42. The method of embodiment 41, wherein the cell is an immune cell.
43. The method of embodiment 38 or 39, wherein the cell is immortalized.
44. The method of any one of embodiments 37-43, further including administering at least one treated cell back to a subject.
45. A method of treating a subject diagnosed as having a hyperproliferative disease or condition or having a high-risk of developing such disease or condition, including administering to the subject an effective amount of the composition of embodiment 33.
46. The method of embodiment 45, wherein the subject is a mammal.
47. The method of embodiment 46, wherein the mammal is a human.
48. The method of any one of embodiments 45-47, wherein the hyperproliferative disease or condition includes one or more of cancer, pre-cancer, or cancer metastasis.
49. The method of embodiment 45-48, wherein the hyperproliferative disease includes one or more of melanoma, lung cancer, breast cancer, pancreatic cancer, brain cancer, prostate cancer, head and neck cancer, kidney cancer, colorectal cancer, lymphoma, colon cancer, or liver cancer.
50. The method of any one of embodiments 45-49, wherein the administering includes one or more of: injection directly into a tumor in the subject; systemic injection in the subject; or topical application to the subject.
51. The method of any one of embodiments 45-50, wherein the administering includes microneedle application to the subject.
52. A method of enhancing effect of an anti-cancer therapy in a subject in need thereof, including administering to a subject in need thereof: an effective amount of the immunotherapeutic construct of any one of embodiments 1-32, or the composition of embodiment 33; and at least one anti-cancer agent.
53. The method of embodiment 52, wherein the anti-cancer agent is a chemotherapeutic agent or a targeted therapeutic agent.
54. A method of enhancing a checkpoint blockade immunotherapy effect in a subject diagnosed as having a neoplasia, including administering to a subject in need thereof: an effective amount of the immunotherapeutic construct of any one of embodiments 1-32, or the composition of embodiment 33; and at least one immune checkpoint inhibitor.
55. A method of enhancing a radiation therapy effect in a subject diagnosed as having a neoplasia, including administering to a subject in need thereof: an effective amount of the immunotherapeutic construct of any one of embodiments 1-32, or the composition of embodiment 33; and at least one radiation therapy.
56. The method of any one of embodiments 52-55, wherein the immunotherapeutic construct or composition and the anti-cancer therapy are administered sequentially or concurrently.
57. The method of any one of embodiments 52-56, wherein the subject is a mammal.
58. The method of embodiment 57, wherein the mammal is a human.
59. A kit including the immunotherapeutic agent of any one of embodiments 1-32, and an anti-cancer agent.
60. the kit of embodiment 59, wherein the anti-cancer agent is a chemotherapeutic agent, a targeted therapeutic agent, or an immune checkpoint inhibitor.

(X) EXAMPLES

Example 1

Utilizing Nanotechnology to Engineer the Tumor Into a Depot for Cancer Vaccination that Primes Systemic Antitumor Immunity Immune checkpoint inhibitors (ICIs), such as inhibitors for PD-L1/PD-1, CTLA-4, etc., have shown impressive outcome in clinics (Sharon et al., *Chin J Cancer*, 33(9):434-44, 2014; Buchbinder & Desai, *Am J Clin Oncol*, 39(1):98-106, 2016). Immune checkpoint inhibitors release the brake of patients' own immune system to fight cancer, offering immunological memory and resulting in long-lasting immune response even after treatment stops. ICIs can thus provide more durable response in late-stage cancer than chemotherapy and targeted therapy can, as shown in FIG. 1. However, the treatment only works in a subset of patients (~10-40%) (Ribas, *Update Cancer Therapeutics*, 2(3):133-139, 2007; Topalian et al., *N Engl J Med*, 366(26): p. 2443-54, 2012). Lack of response is typically due to the absence of pre-existing antitumor immunity (e.g., effector (CD8+) T cells against tumors) (Santarpia & Karachaliou, *Cancer Biology & Medicine*, 12(2):74-78, 2015; Tumeh et al., *Nature*, 515(7528):568-571, 2014). Therefore, the ability to prime anti-tumor CD8+ T cell repertoires is essential for immunotherapy.

In situ tumor vaccination is a strategy in which tumors are locally killed, releasing tumor antigens in the presence of immunostimulation, which together prime systemic adaptive immunity against tumors (Pierce et al., *Hum Vaccin Immunother*, 11(8):1901-9, 2015). This strategy has great promise because it circumvents the need to pre-identify tumor antigens in conventional cancer vaccine development. This is also a personalized therapy, since a unique set of tumor antigens is released and primes specific immunity for each patient.

The herein provided immunotherapeutic approach for cancer utilizes patients' own tumors as a depot for a personalized set of tumor antigens (in situ tumor vaccination). Examples of the system described herein are referred to as AIRISE (Augmenting Immune Response and Inhibiting Suppressive Environment of Tumors); AIRISE is aimed to improve patient survival outcomes when used alone or together with checkpoint inhibitors (FIG. 1). The provided particles (immunotherapeutic constructs) carry adjuvant (e.g., CpG) and one or more compounds (siRNA, drug, small molecules, etc.) that cause antigen release and/or modulate immunosuppressive tumor microenvironment (e.g., docetaxel, siRNA against STAT3). Upon treatment with a provided immunotherapeutic construct at a tumor site (for instance, through local intratumoral injection or tumor homing via systemic delivery), tumor antigens are released in the presence of immunostimulation (provided by the adjuvant), initiating adaptive immunity. Simultaneously, a compound that modulates the immunosuppressive tumor microenvironment can be co-delivered on the same nanoparticle, maximizing in situ tumor vaccination effect. Tumor antigens can be taken up by AIRISE-activated antigen-presenting cells (APCs), which present the antigen to naïve T cells. T cells (against those tumor antigens) are primed and activated into effector T cells (either in lymph nodes or in tumor site) and proliferate throughout the body. Effector T cells will home specifically to tumors sharing the same tumor antigens wherever they are located in the body (e.g., both locally treated tumor and untreated metastatic tumors elsewhere in the body). Death of cancer cells by cytotoxic T cells releases more tumor antigens, amplifying the process of anti-tumor T cell generation in a positive feedback loop. Notably, even when the treatment is local (e.g., intratumoral injection), the vaccination effect induced locally at the tumor site generates systemic long-lasting anti-tumor immune response (FIG. 2). For example, AIRISE can be injected directly into melanoma lesions, and the treatment may affect both the injected tumor and untreated metastasized melanoma tumors in lung or liver.

These anti-tumor T cells trained to recognize the specific tumor antigens will control tumors both at injected/treated site(s) and elsewhere in the body (FIG. 2). The cargo combination can be applied on any type of micro/nanoparticles to make AIRISE. Examples that follow utilize established mesoporous silica nanoparticles (U.S. Patent Application Publication 2017/0172923) as a proof of concept. Another examples shown in FIG. 11 utilized cationic lipid particles with the hydrodynamic size of 1.1 micron for in situ vaccination with CpG and siSTAT3, and yield similar outcome with FIG. 7, suggesting that various types and sizes of particles can be used.

Methods & Materials

Nanoparticle synthesis and characterization: Mesoporous silica-based nanoparticles were synthesized as previously described (Ngamcherdtrakul et al., *Advanced Functional Materials*, 25(18):2646-2659, 2015; Ngamcherdtrakul et al., *International J Nanomed*, 13:4015-4027, 2018). Briefly, mesoporous silica nanoparticle (MSNP) was synthesized by sol-gel synthesis. The MSNP core was coated layer-by-layer with polyethylenimine (PEI) and polyethyleneglycol (PEG). PEI on the MSNP was also cross-linked for enhanced oligonucleotide delivery efficacy and safety as explained previously (Ngamcherdtrakul et al., *Advanced Functional Materials*, 25(18):2646-2659, 2015). MSNP coated with crosslinked PEI and PEG is referred to henceforth as "NP" in this Example.

Figures 26, 27:
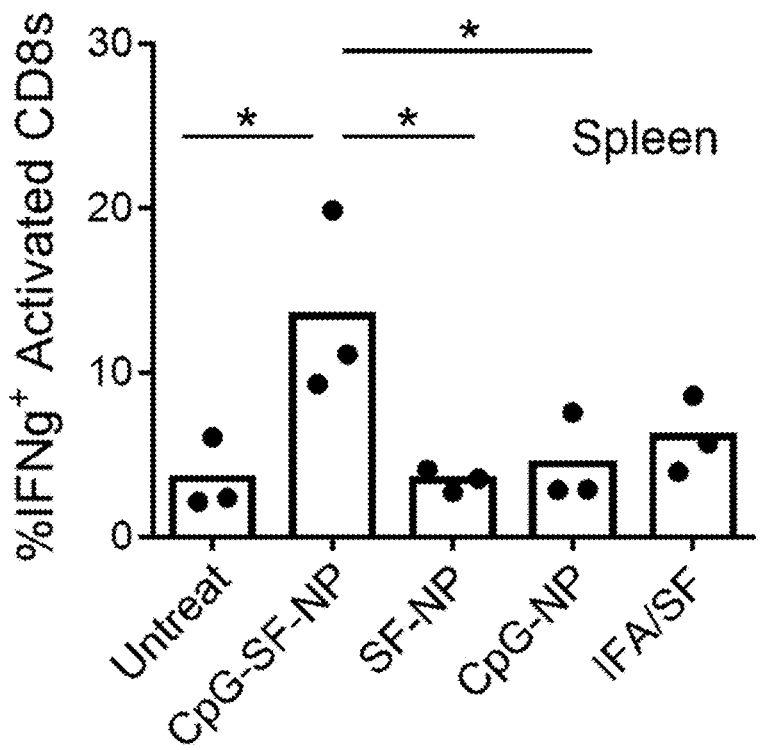
FIG. 26. Hydrodynamic size of mesoporous silica nanoparticles coated with cross-linked PEI and PEG (NP) loaded with different amount of siRNA and CpG, specified as wt % of the whole construct. Average size (Z-average) and polydispersity index (PDI) is shown from 3 measurements using Malvern Zetasizer.
FIG. 27. CpG-NP can generate antigen-specific (adaptive) immune response in the presence of antigen. Figure shows the percentage of IFNγ activated CD8+ T cells after incubation in the presence of SF (SIINFEKL peptide). The cells were obtained from lymph nodes of untreated mice, mice treated with NPs loaded with SF and CpG (CpG-SF-NP), NPs loaded with SF (SF-NP), mice or NP loaded with CpG (CpG-NP), and mice treated with SF formulated with Incomplete Freund's Adjuvant (IFA/SF). *p<0.05. Doses used: 16 µg CpG and 40 µg SF. Route of administration in mice is foodpad injection.
Figure 28:
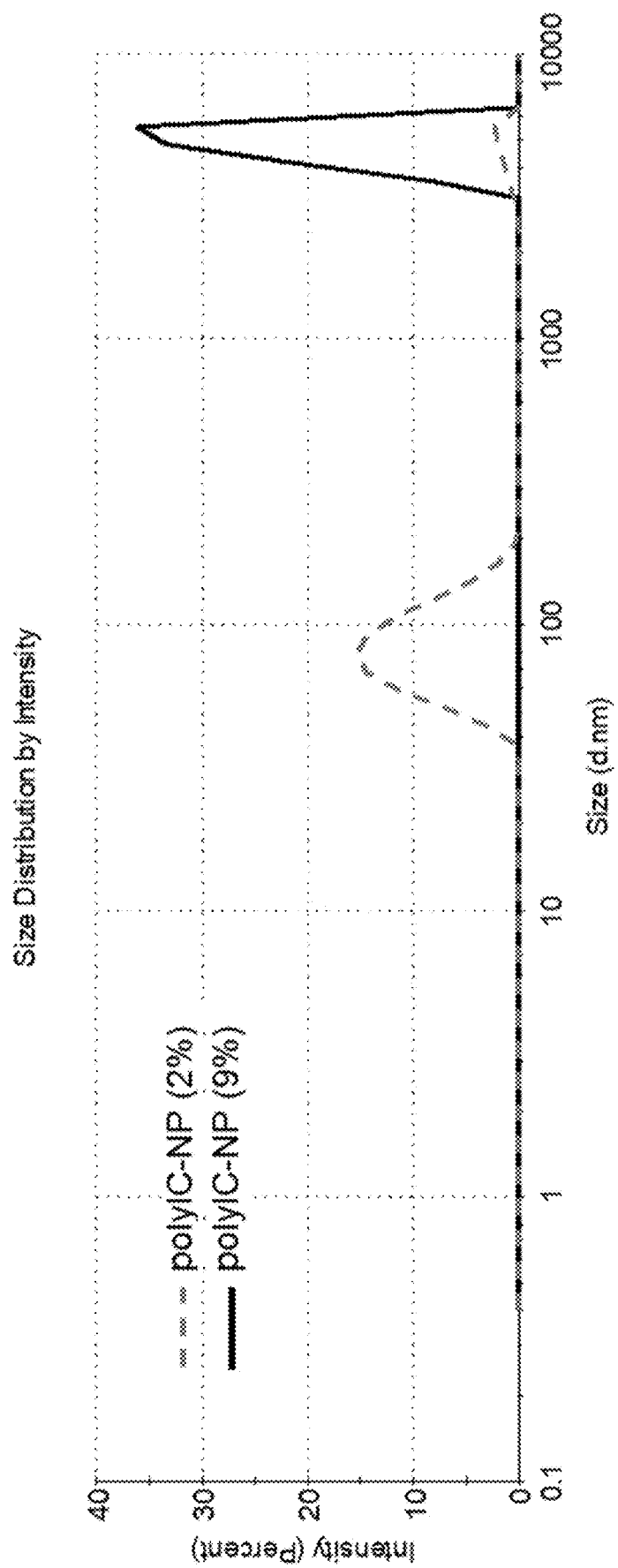
FIG. 28. Hydrodynamic size of nanoparticles (MSNP-PEI-PEG) loaded with poly I:C at about 2 wt. % and 9 wt. %, measured in PBS.

Cargo loading on the NP: siRNA and CpG (ODN 1826; SEQ ID NO: 7) were loaded electrostatically on the nanoparticle (NP) by 10-minute mixing, though a shorter time (2-5 minutes) was also effective. Mitoxantrone was also loaded to the NP by 4-h mixing at room temperature in aqueous solution (e.g., PBS). Loading was performed in a complete binding manner as confirmed by the absence of free cargo molecules in the supernatant upon separating out cargo-loaded NP by centrifugation. The cargo content was measured by spectrophotometry. siRNA was conjugated with Dy677 dye (Dharmacon®) and thus was quantified by fluorescence signal. CpG was measured with Nanodrop Spectrophotometry. Unbound siRNA and CpG could also be measured by gel electrophoresis. Mitoxantrone (MTX) was quantified by absorbance measurement at 658 nm. Final NP with CpG and siRNA was characterized for hydrodynamic size in PBS by Zetasizer (FIGS. 26 and 29).

Docetaxel was loaded in excess on the nanoparticle before PEI binding. Briefly, MSNP was mixed with docetaxel in ethanol overnight before PEI binding. Unbound docetaxel and PEI were washed out in PBS. PEI-NP(DTX) was then conjugated with PEG following previous methods (Ngamcherdtrakul et al., *Advanced Functional Materials*, 25(18): 2646-2659, 2015; Ngamcherdtrakul et al., *International J Nanomed*, 13:4015-4027, 2018). The final products contain 0.5-1.7 wt. % DTX at the starting DTX to MSNP mass ratio of 0.2-0.8. They have the DLS size of 100 nm.

B16F10 bilateral orthotopic murine melanoma tumor model: 6-week-old female C57BL/6 mice were obtained from Charles River NCI colony (Wilmington, Mass.). Each mouse was intradermally implanted with B16F10 cells on the left (local, 250,000 cells) and right (distant, 100,000 cells) shoulders. At 8 days post-implantation, test compound/construct was intratumorally injected to only the left (local) tumor, while the right (distant) tumor was left untreated. Unless otherwise specified, the test compound/construct was given every 3 days for 3 doses. Burden of both local and distant tumors in mice were measured with Vernier Caliper every 1-2 days, and tumor volume was calculated by V=0.5×length×width$^2$. Survival was also monitored. Mice were sacrificed when total tumor burden exceeded 2000 mm$^3$.

For the study that combines NP treatment with immune checkpoint inhibitors, a cocktail of PD-1 Ab (200 µg/mouse) and CTLA-4 Ab (100 µg/mouse) was given intraperitoneally on the same day (3 doses every 3 days) as intratumoral treatment of the NP compounds.

To confirm that the treatment efficacy is immune-mediated, mice treated with test compound/construct was injected intraperitoneally with CD8 antibody (200 µg/mouse), starting one day before first intratumoral treatment and continuing throughout the entire study.

For immune profiling, local and distant tumors and their respective draining lymph nodes were collected and processed into single cells, following an established protocol in the art. Harvested cells were then stained with a set of fluorescently labelled antibodies for different surface proteins (e.g., CD45, CD8, CD4, CD44, TIM3, PD-1, CD39, LAG3, CD3, CD19, CD11b, CD11c, MHCII, CD80, Ly6C, Ly6G, F4/80, CD206) that together identify different immune cell populations and their status. Certain intracellular proteins (e.g., Ki67, FoxP3, STAT3) can also be stained following the manufacturer's protocol (BD Biosciences). Flow cytometry was typically performed in two separate antibody panels (lymphoid and myeloid) by BD Fortessa (4 lasers, up to 18 parameters). Fluorescence compensation was performed to ensure robustness of multi-color flow cytometry analysis following the established protocol known in the art. For AIRISE uptake study in tumor microenvironment (FIG. 18), AIRISE-02 (loaded with Alexa488 dye conjugated siSCR instead of siSTAT3) was injected intratumorally into mice bearing bilateral B16F10 tumors, as described earlier. Two hours after treatment, tumors (treated and untreated) were harvested, processed into single cells, and subjected to surface staining with a panel of antibodies as described herein. The presence of AIRISE-02 in different cell populations in the tumor was analyzed by flow cytometry.

LLC-JSP metastatic murine lung tumor model: LLC-JSP (200,000 cells) were injected intravenously (tail-vein) to 6 week old C57BL/6 mice. Three days after cancer cell injection, mice were randomly grouped and treated with the test compounds/constructs every 3 days for a total of 4 doses. In this model, AIRISE-02 was injected intravenously through the tail-vein instead of intratumorally.

CT26 bilateral ectopic tumor models. 250K and 100K CT26 (murine colorectal cancer) cells were implanted into bilateral abdomens of each mouse (Balb/c). 15 days after tumor implantation, mice were treated with the test compounds/constructs.

4T1 bilateral orthotopic tumor models. 100K and 40K 4T1 cells were implanted into bilateral mammary fat pads of each mouse (Balb/c). 8 or 11 days after tumor implantation (as specified), mice were treated with the test compounds/constructs.

Results & Discussion

CpG-Loaded Nanoparticles Exhibit Better Adjuvant Property than Free CpG.

Figure 3:
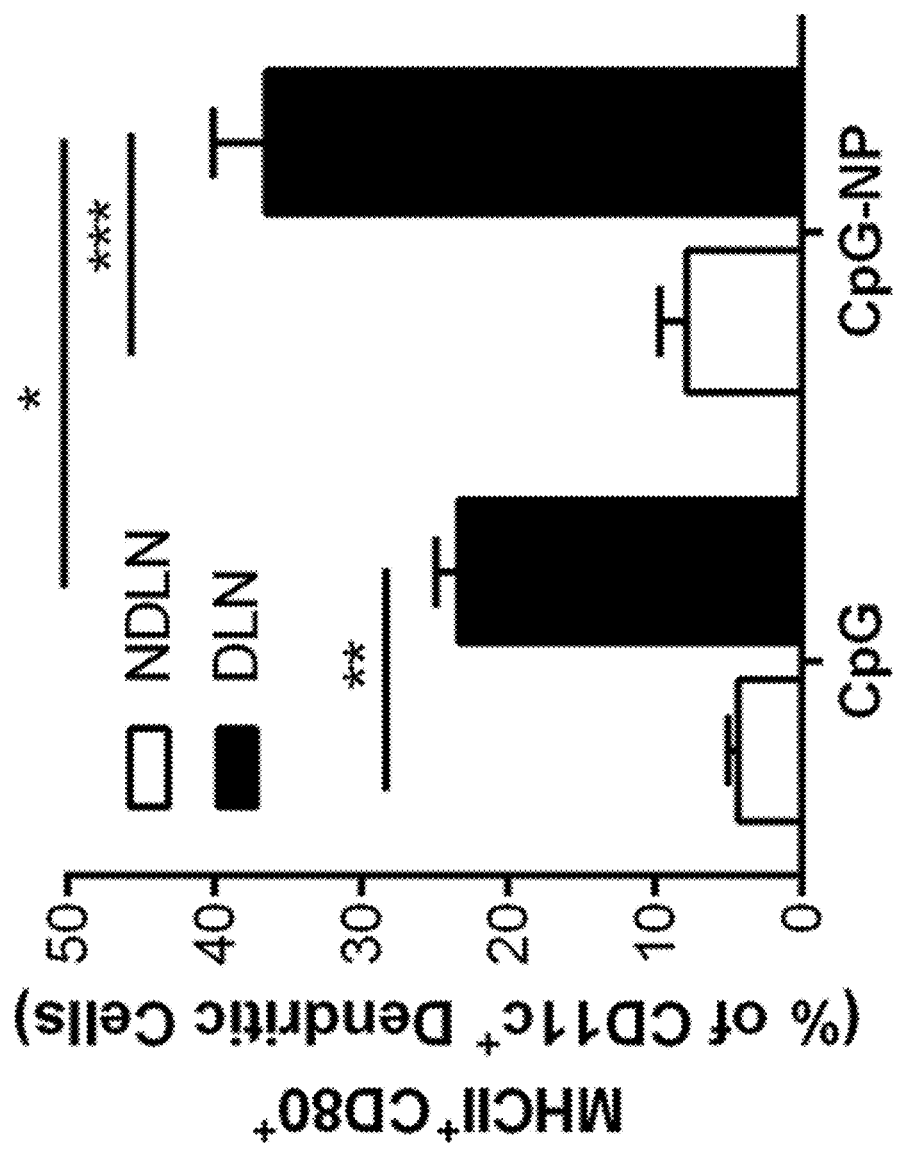
FIG. 3. Greater activation of dendritic cells (MHCII+ CD80+ CD11c+ cells) after treatment with CpG-NP over CpG. CpG or CpG-NP was administered to mice by footpad injection. One day after treatment, draining (DLN) and non-draining lymph nodes (NDLN) were collected and processed into single cells for flow cytometry analysis to identify % activated dendritic cells. *p<0.05, p<0.01, *p<0.0001. The CpG ODN 1826 (SEQ ID NO: 7) was used throughout the examples unless otherwise specified.
Figure 4A:
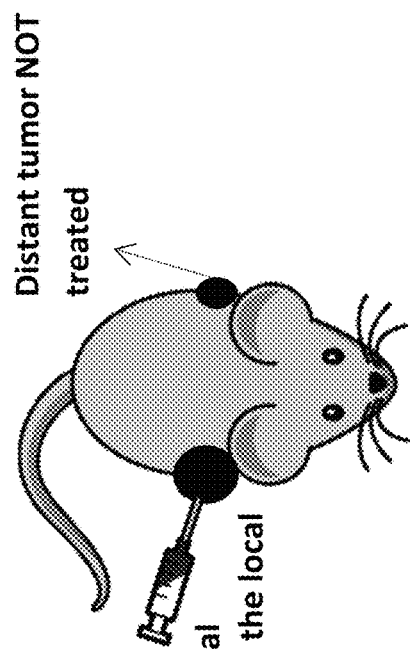
FIGS. 4A-4D. Effectiveness of CpG-NP administered to a melanoma mouse model as in (FIG. 4A, mouse implanted with bilateral tumors) in inducing in situ tumor vaccination as indicated by inhibited tumor growth curves of local treated tumors (FIG. 4B) and distant untreated tumors (FIG. 4C) and prolonged survival curve of the mice (FIG. 4D). 250,000 and 100,000 B16F10 cells were implanted into each mouse (C57BL/6) to establish local and distant tumors, respectively. Eight days after tumor implantation, CpG-NP or saline was intratumorally injected into the local tumor every three days for a total of three doses. Dose (per each injection) was 20 μg CpG and 0.2 mg NP. Tumor volumes are plotted as mean and SEM. Statistical difference (*) was evaluated between CpG-NP and saline. *p<0.05, *p<0.001, **p<0.0001.
Figure 4A:
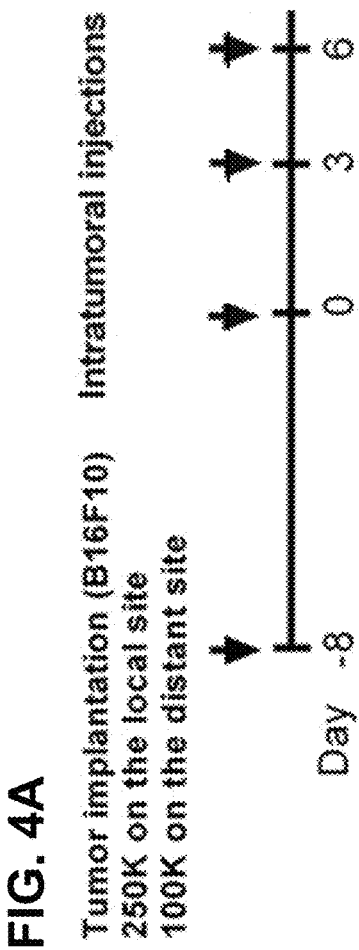
Figure 4B:
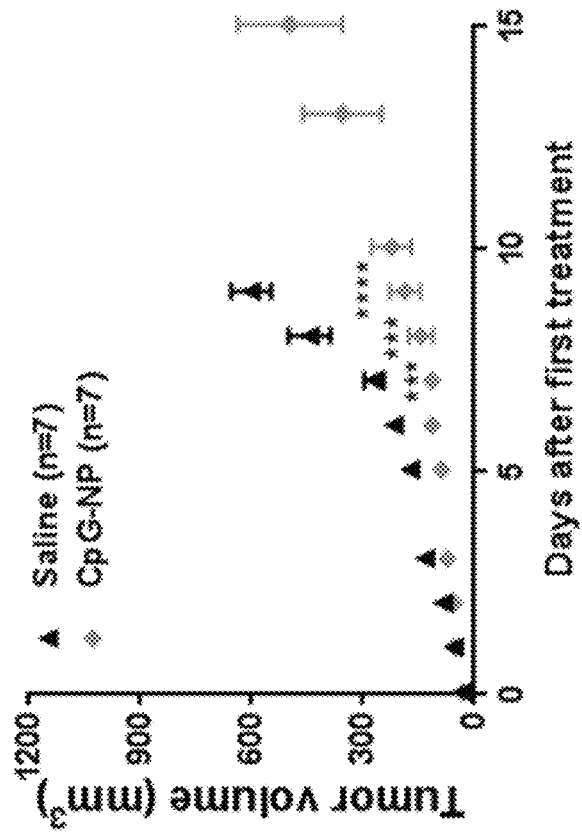
Figure 4C:
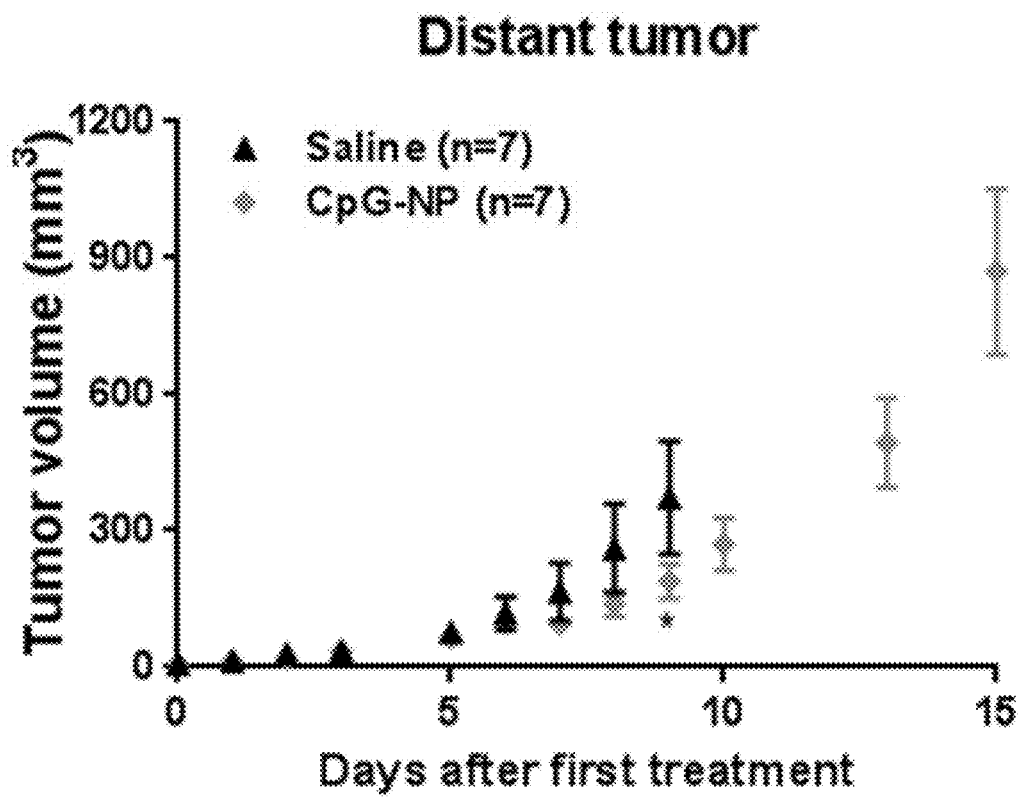
Figure 4D:
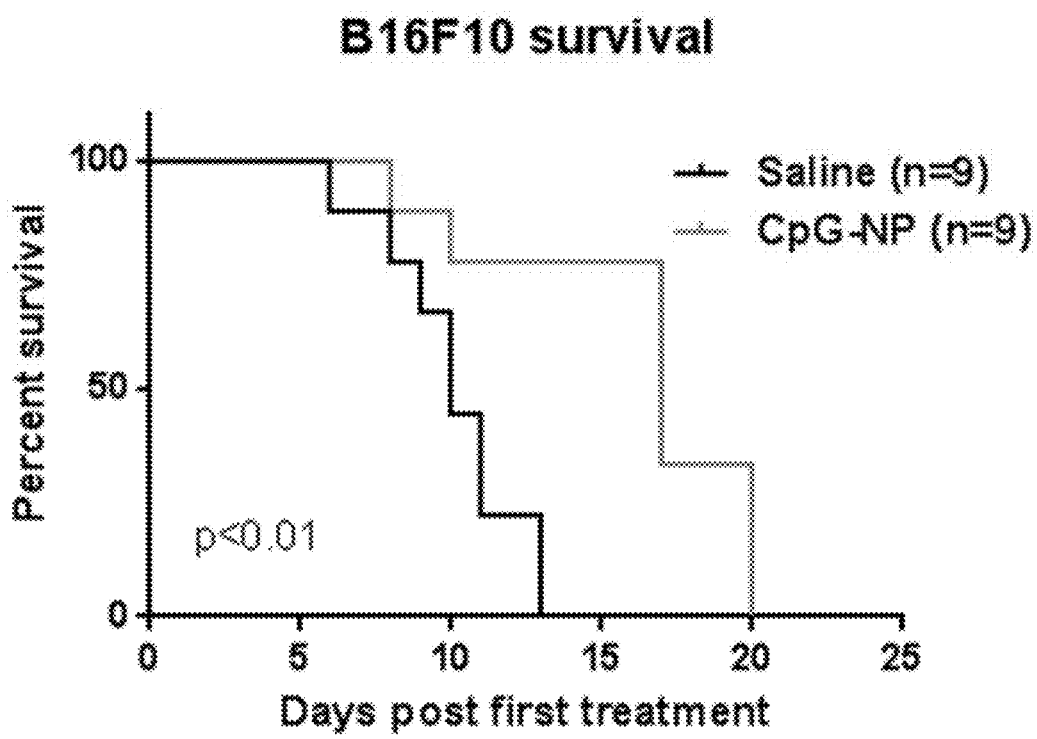
Figure 5A:
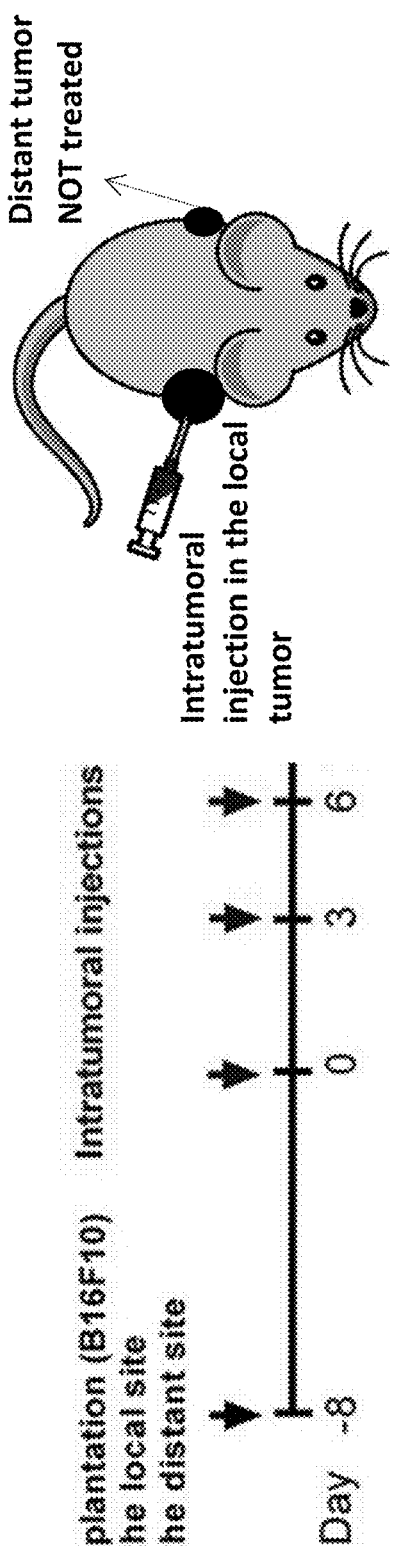
FIGS. 5A-5D. Effectiveness of NP loaded with CpG and/or docetaxel (DTX) (AIRISE-01) administered to a melanoma mouse model as in (FIG. 5A) in inducing in situ tumor vaccination as indicated by inhibited tumor growth curves of local treated tumors (FIG. 5B) and distant untreated tumors (FIG. 5C), and prolonged survival curve of the mice (FIG. 5D). Mice (same model as FIG. 4) were treated with CpG-NP, CpG-DTX-NP or saline. Dose (per each injection): 20 μg CpG; 2 μg DTX; 0.2 mg NP. Tumor volumes are plotted as mean and SEM. * denotes the statistical difference between saline and CpG-NP. $ denotes the statistical difference between saline and CpG-DTX-NP. p and $$p<0.01; **p and $$$$p<0.0001.
Figure 5B:
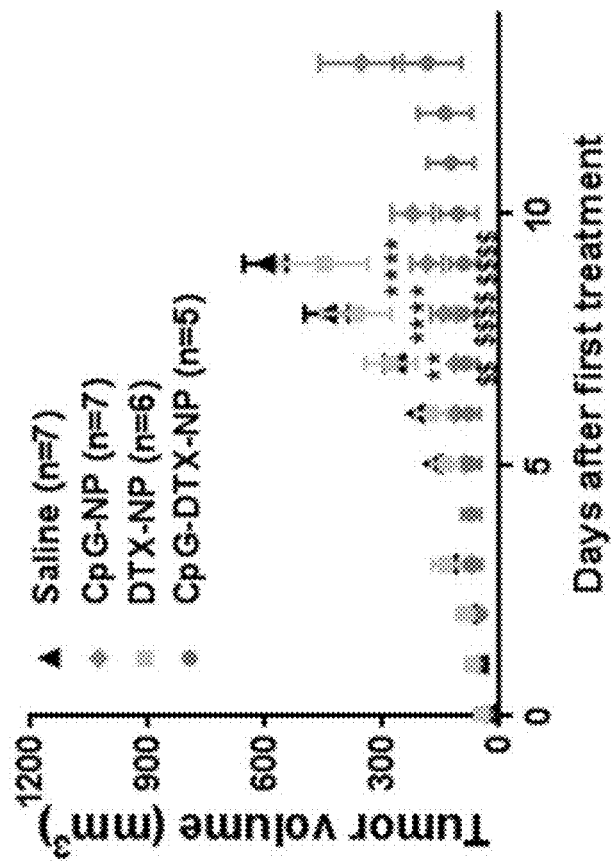
Figure 5C:
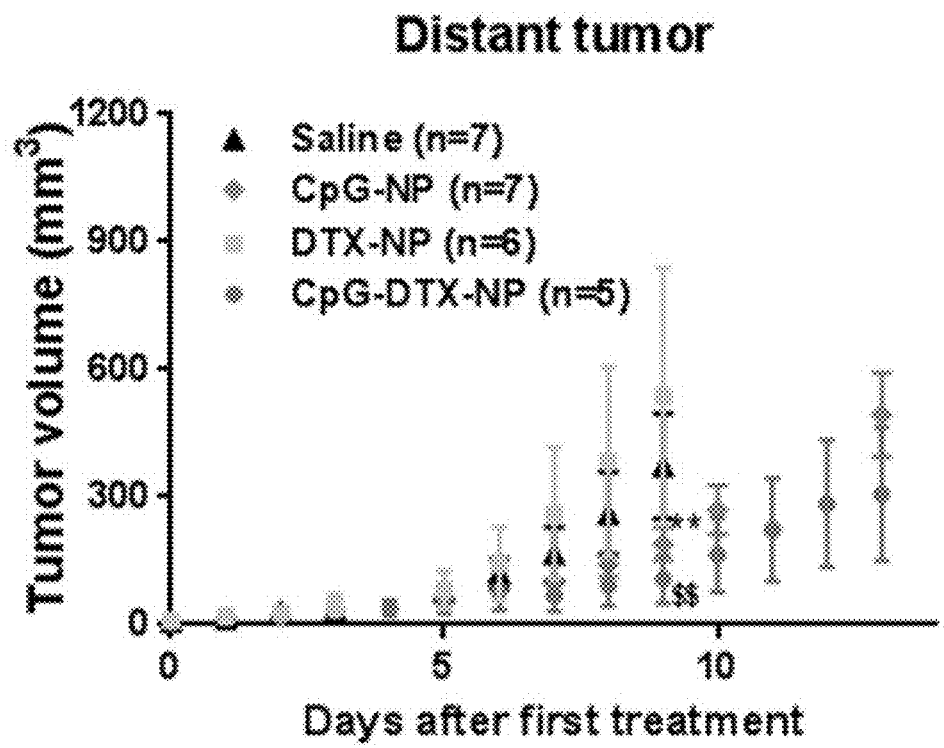
Figure 5D:
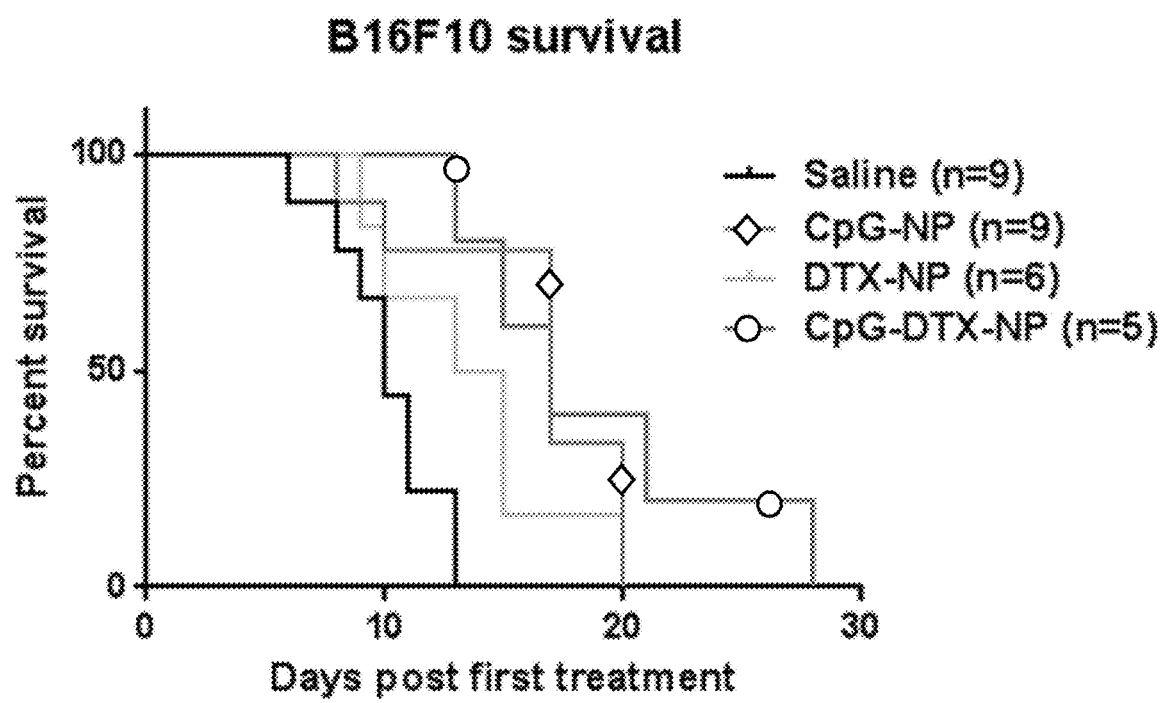

C57BL/6 mice (n=3/group) were injected with 4 µg free CpG or 4 µg CpG on the NP into one footpad of the mouse. Twenty-four hours after injection, local draining lymph nodes (DLN) and non-draining lymph nodes (NDLN) were harvested and analyzed by flow cytometry for CD11c, MCHII, and CD80 expression. CpG-loaded nanoparticles activated dendritic cells in local DLN significantly better than free CpG (FIG. 3). CpG-nanoparticles also have added potential to co-deliver several therapeutic cargos to the same site. Further, the exemplary nanoparticle was highly optimized for delivery of siRNA, which can modulate immunosuppressive characteristics of tumor at the mRNA level. Co-delivering CpG (or another adjuvant) with siRNA or other targeted molecules that tackle several hallmarks of tumor immunosuppression is proposed to beneficially prime immunotherapeutic effects.

Adjuvant-Loaded Nanoparticles Triggers In Situ Tumor Vaccination

To evaluate the ability of CpG-NP to trigger in situ tumor vaccination, mice bearing two (bilateral) melanoma tumors were used. The treatment was injected intratumorally to only one of the two tumors, while the other tumor was left untreated. Growth of both tumors was monitored; the intratumoral treatment of CpG-NP successfully primed a whole-body immune response and induced a strong abscopal effect—inhibition of both locally treated and distant untreated tumors (FIG. 4). As a result, survival is also prolonged. The herein described immunotherapeutic construct technology triggers in situ vaccination, thus there is no need for tumor antigens to be loaded onto or into any of the complexes.

Co-Delivery of Drug and CpG on the Same NP can Induce Effective In Situ Tumor Vaccination Intratumoral injection of chemotherapy drugs to trigger in situ tumor vaccination has not been widely explored. In fact, intratumoral injection of nanoparticle containing chemotherapy drug and adjuvant has not been done before. This is due to potential toxicity of chemotherapy drug to immune cells that may negate any activated immunotherapeutic response.

Surprisingly, co-delivery of the chemotherapeutic drug docetaxel (DTX) and CpG on the same nanoparticle (CpG-DTX-NP) did not worsen the in situ vaccination effect of CpG-NP despite potential chemotherapy's toxicity to immune cells (FIG. 5). In fact, CpG-DTX-NP can control local treated tumor better than CpG-NP. At the same time, CpG-DTX-NP still induces in situ vaccination effect slightly better than CpG-NP, as shown by the control of the distant tumor and prolonged survival of the mice. Also, DTX-NP does not show any significant activity.

Co-Delivery of another chemotherapeutic drug mitoxantrone (MTX) and CpG on the same nanoparticle also triggered in situ vaccination effect of CpG-NP (FIG. 16).

Immune Cell Analysis Shows Significant Increase in Activated CD8+ T Cells in Tumors and Lymph Nodes.

Figure 6:
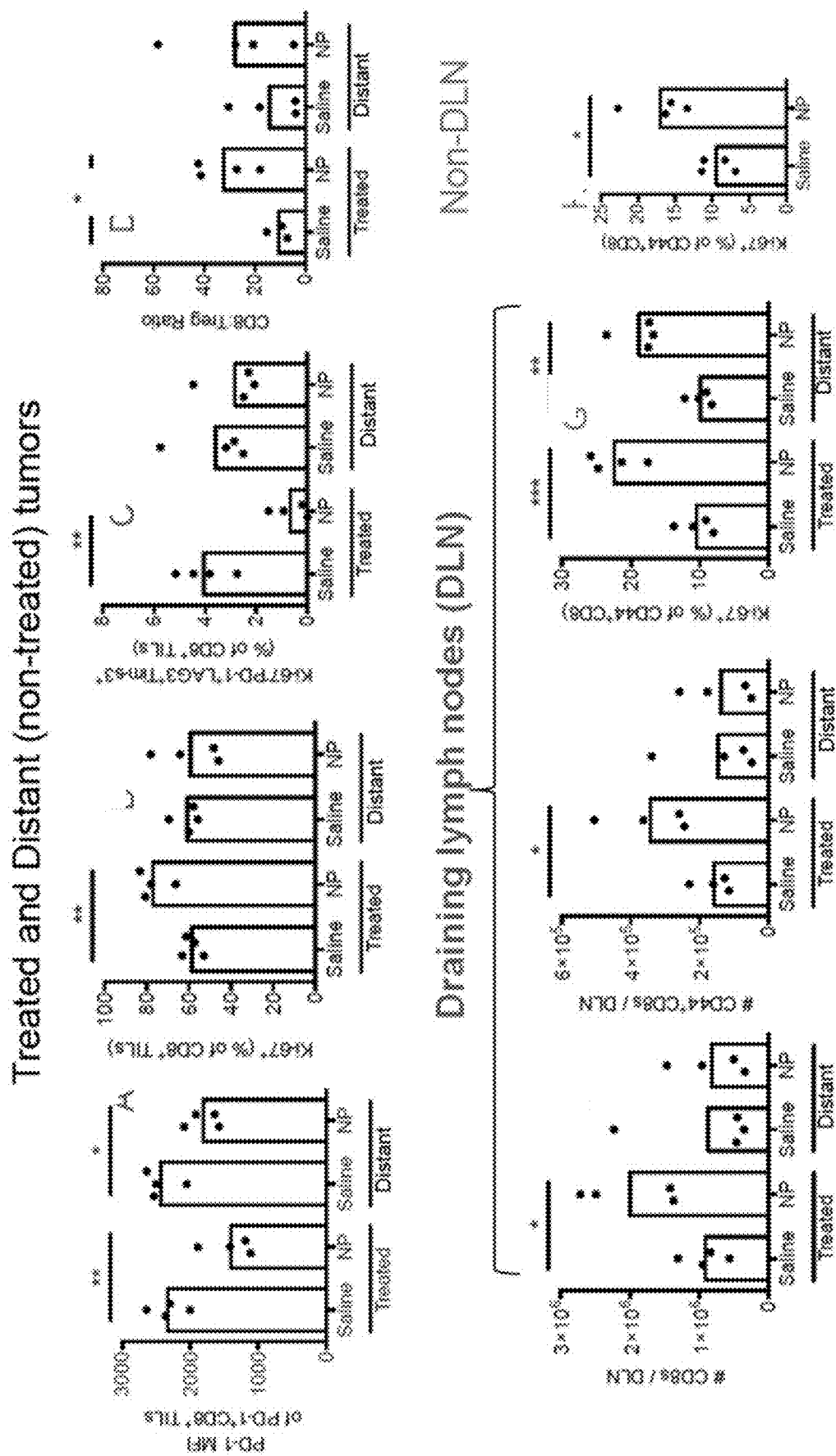
FIG. 6. Increase in cytotoxic CD8+ T cells in the local and distant tumors, DLN of local (treated) and distant tumors, and non-DLN triggered by CpG-DTX-NP (denoted as NP in this figure). All conditions are the same with FIG. 5A. Tumors and lymph nodes (tumor-draining and non-draining) were collected 7 days after the first injection (see FIG. 5A). Cells were stained with a panel of antibodies to evaluate the lymphoid cell population and activity. p-values; *p<0.05. p<0.01, *p<0.001.

After treatment (FIG. 5A), T cell status was characterized in the local and distant tumors at day 7 post first dose. Compared to saline, treatment with CpG-DTX-NP (shortened as "NP" in FIG. 6) led to desirable characteristics of cytotoxic CD8+ T cells as follows: lower expression of PD1 (FIG. 6A) in both treated and distant tumors, higher proliferation of CD8+ T cells in treated tumors (FIG. 6B), less exhausted CD8+ T cells in treated tumors (FIG. 6C), and higher ratio of CD8+ T cells over regulatory T cells (FIG.

6D). Likewise, higher CD8+ T cells were seen in the draining lymph nodes (DLN) of the treated tumors (FIG. 6E), which were also more activated (FIG. 6F). The activated CD8+ T cells were more proliferative (by Ki67 marker) in the DLN of both tumors (FIG. 6G). More proliferating and activated CD8+ T cells were observed in non-DLN (FIG. 6H), suggesting that T cells were transported outside the local lymph node (e.g., in blood), contributing to the abscopal effect of the treatment. These T cell characteristics indicate that the herein-described nanoparticles can increase the beneficial antitumor T cell repertoires (non-exhausted state), generating whole-body immunity. While the DTX on our NP killed tumor cells to release tumor antigens, it did not harm CD8+ T cells, but rather increased the proliferation.

Co-Delivery of siRNA and CpG on the Same NP can Induce Effective In Situ Tumor Vaccination This is the first time that a single NP has be used to co-deliver an adjuvant and a siRNA via intratumoral injection. While delivery of immunogenic chemotherapy drugs, tumor antigens, or adjuvants by nanoparticles has been done before, siRNA has never been co-delivered with adjuvant on nanoparticles.

Figure 7A:
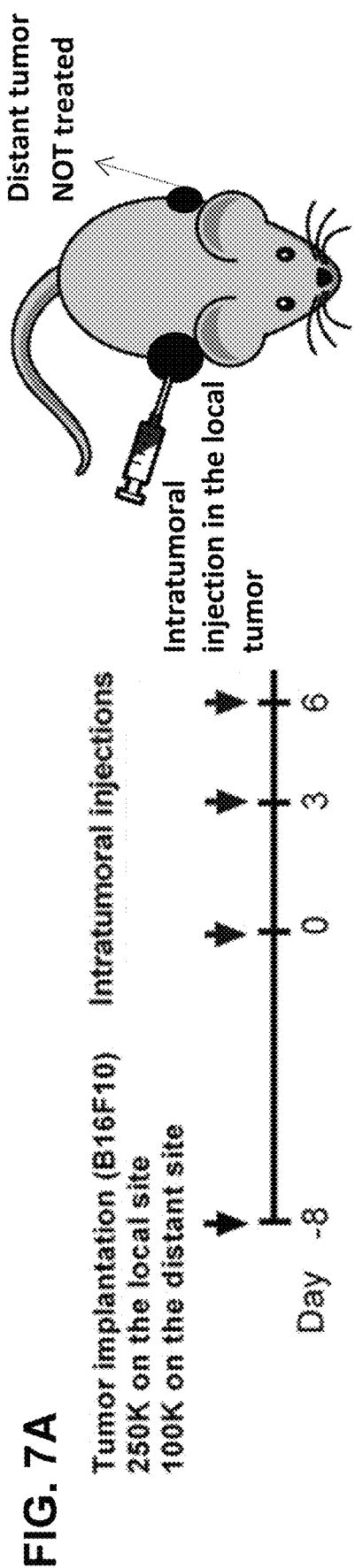
FIGS. 7A-7D. Effectiveness of siSTAT3-CpG-NP (AIRISE-02) administered to a melanoma mouse model as in (FIG. 7A) in inducing in situ tumor vaccination as indicated by inhibited tumor growth curves of local treated tumors (FIG. 7B) and distant untreated tumors (FIG. 7C), and prolonged survival curve of the mice (FIG. 7D). Tumor volumes are plotted as mean and SEM. Dose (per each injection): 20 μg CpG; 4 μg siSTAT3; 0.2 mg NP. Statistical difference (p-values as specified, *) was evaluated between CpG-NP and siSTAT3-CpG-NP (two groups that respond the best).
Figure 7B:
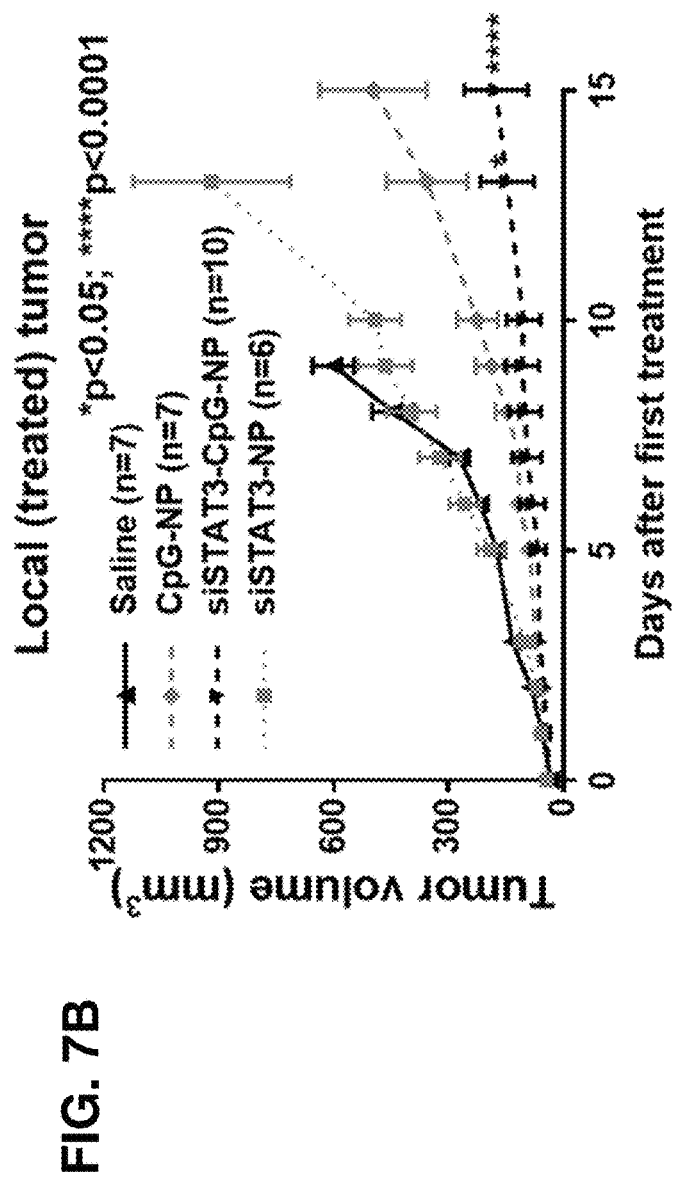
Figure 7C:
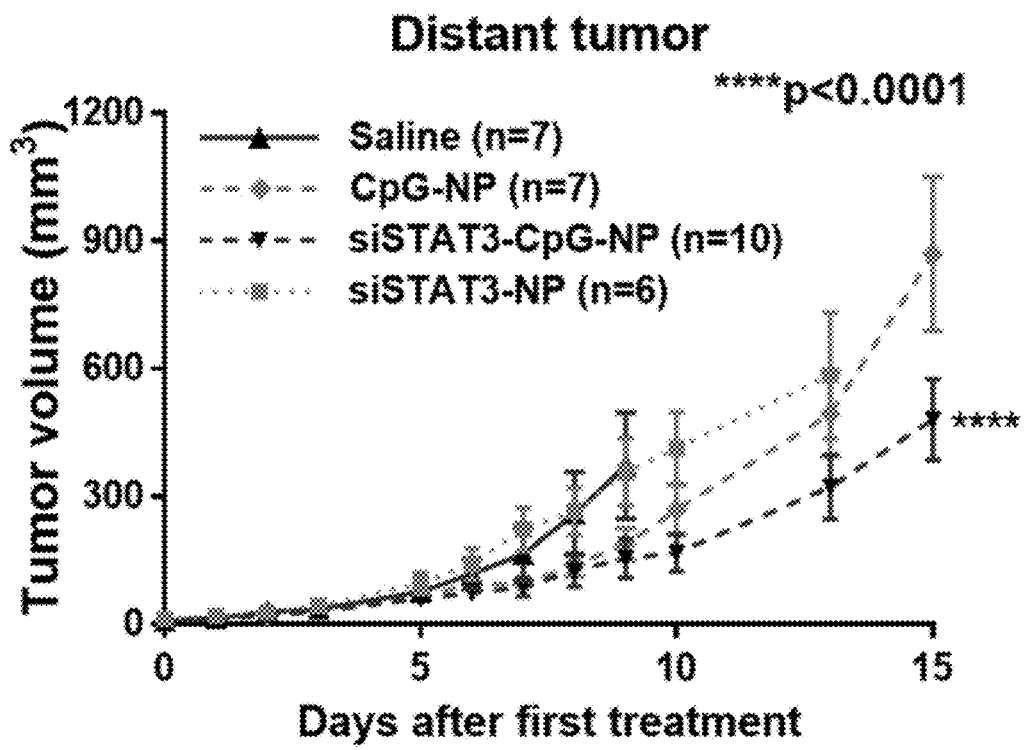
Figure 7D:
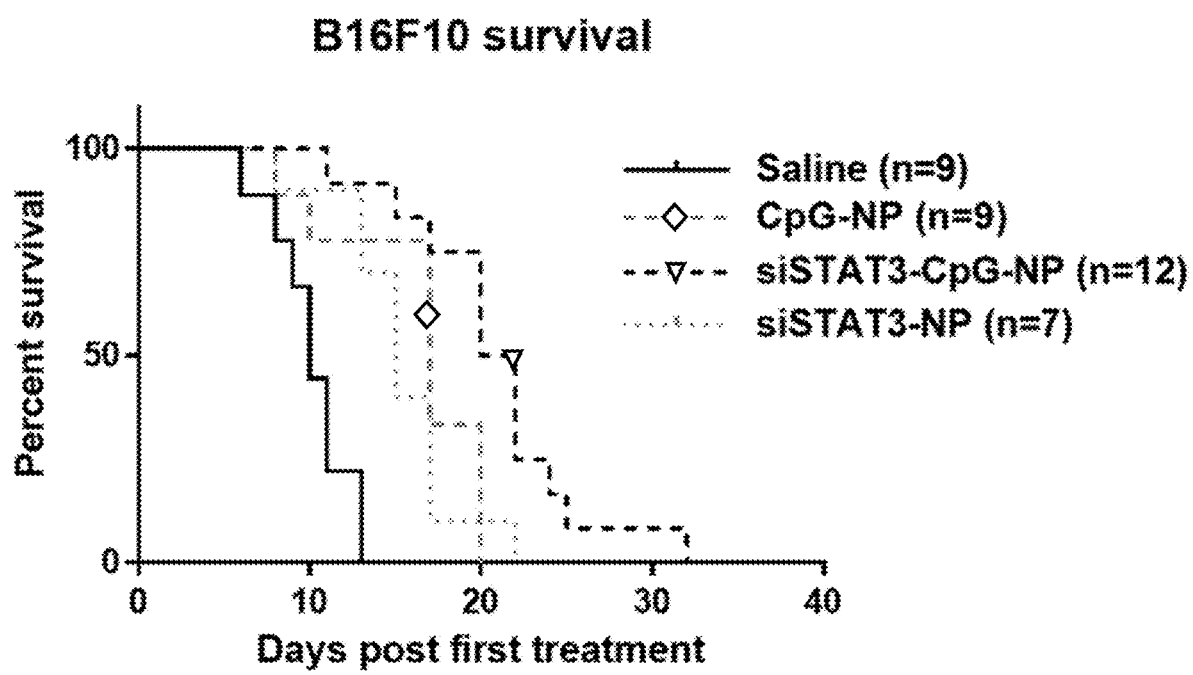

Intratumoral Codelivery of CpG Oligo and siSTAT3 on NP Induced Systemic Antitumor Immune Response in a Melanoma Mouse Model.

siSTAT3 (2 wt %) was loaded in the mesoporous silica core of NP, and CpG oligo (10 wt. %) on the external surface (bound to cationic polymer layer but protected under PEG from enzymatic degradation). It is proposed that tumor antigens (already in the tumor or released by cancer death upon treatment) will prime anti-tumor immunity in the presence of immunostimulation by CpG. siSTAT3 modulates immunosuppressive tumor environment, amplifying immunotherapeutic response. To demonstrate this, siSTAT3-CpG-NP (AIRISE-02) was evaluated in a bilateral B16F10 melanoma tumor model in mice (FIG. 7A). At 8 days post tumor implantation, AIRISE-02 was injected into one of the tumors (local) for three doses total, 3 days apart. AIRISE-02 significantly improved the survival of the mice (FIG. 7D), reduced both local (treated, FIG. 7B) and distant (non-treated, FIG. 7C) tumors, suggesting successful in situ tumor vaccination and the abscopal effect (effect in the site beyond the treated/injected site) of the treatment. FIGS. 7B-7C also shows that siSTAT3-CpG-NP is superior to CpG-NP and siSTAT3-NP.

Figure 17A:
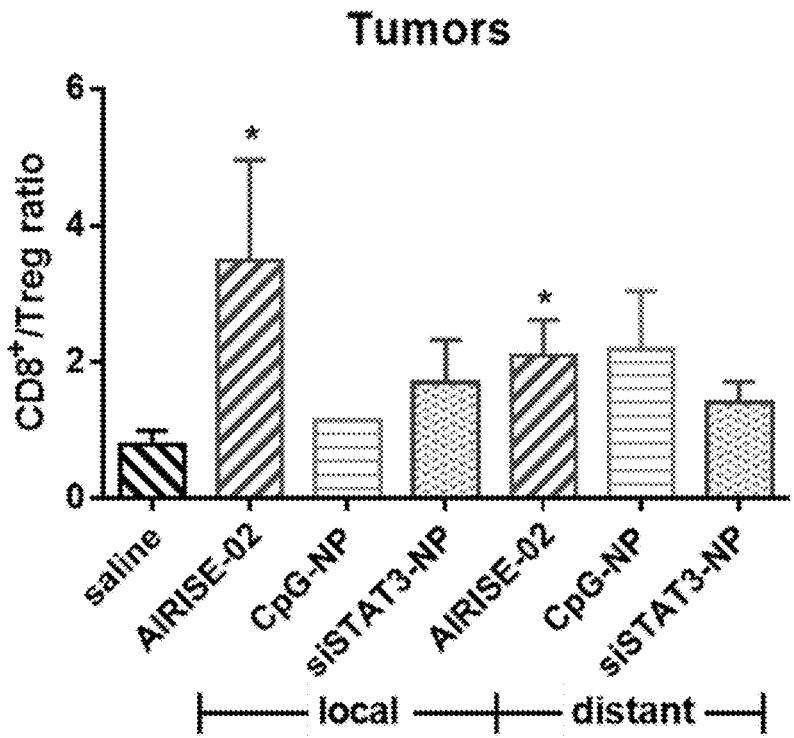
FIGS. 17A-17C. AIRISE-02 enhanced proliferation of CD8+ T cells in local (treated) and untreated tumors and their tumor draining lymph nodes (DLN). Model, treatment dose, and schedule were as in FIG. 7. 7 days after the first treatment, cells harvested from tumors and DLN of both local (treated) and distant (untreated) tumors were analyzed to determine the ratio of CD8+ T cells over CD4+FoxP3+ regulatory T cells in the live CD45+CD3+ T cell populations of tumors (FIG. 17A) and DLNs (FIG. 17B), along with effector (CD44+) CD8+ T cell's proliferation status (Ki-67) in the lymph nodes (FIG. 17C). *$p<0.05$, $p<0.01$, *$p<0.001$, ****$p<0.0001$ (n=3/group) for AIRISE-02 vs. saline, unless the bracket specifies otherwise.
Figure 17B:
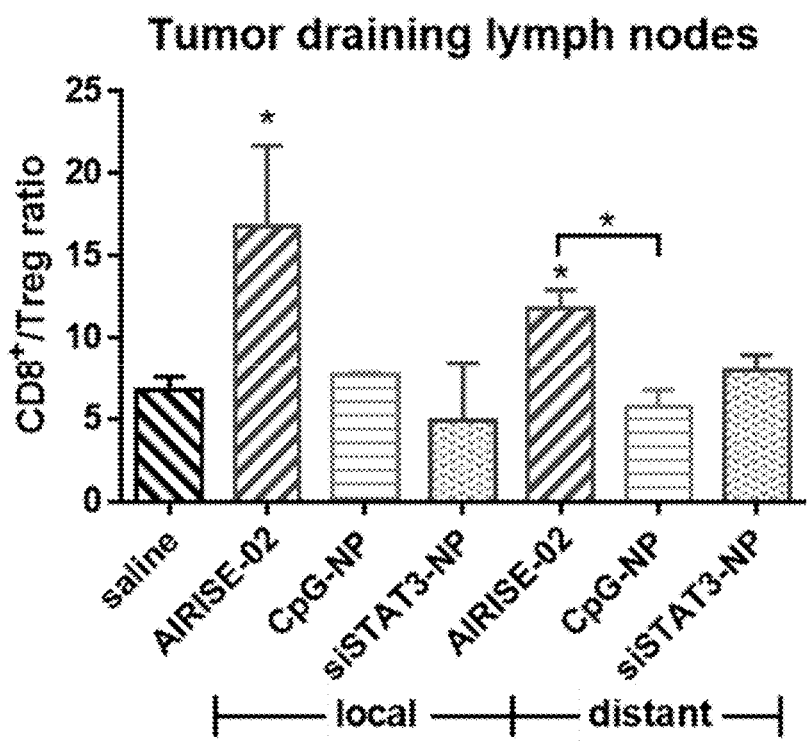
Figure 17C:
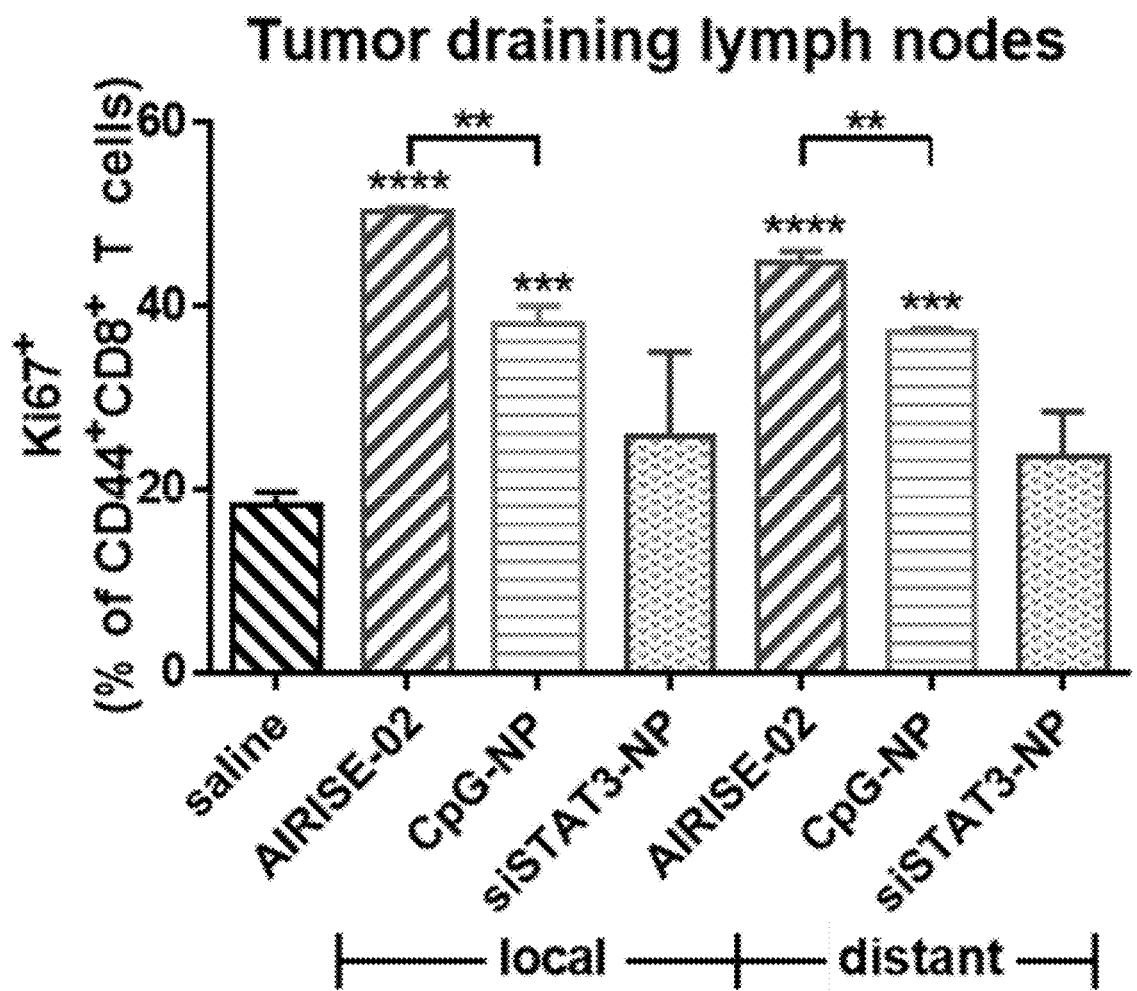

In a separate experiment, mice were treated with AIRISE-02 (siSTAT3-CpG-NP) in the same manner as FIG. 7. Mice were sacrificed one day after the third dose (or 7 days after the first dose). Tumors and associated draining lymph nodes (DLNs) were collected and subjected to immune profiling with multi-color flow cytometry. FIG. 17 shows that AIRISE-02 resulted in significantly higher CD8/Treg ratios in both local (treated) and distant (untreated) tumors and associated DLNs (p<0.05 for AIRISE-02 vs. saline), confirming successful in situ tumor vaccination. Regulatory T cells (Treg) are typically elevated in patients' tumors and suppress anti-tumor immune response, including CD8+ T cell activity. Thus, higher intratumoral CD8/Treg ratio is desirable and is one indicator of prolonged survival in cancer patients. CpG-NP did not significantly increase CD8/Treg in either of the tumors or lymph nodes at this timepoint, corresponding with its poorer efficacy than AIRISE-02 in FIG. 7. Furthermore, the effector CD8+ T cells in the lymph nodes were more proliferative (Ki-67) in AIRISE-02-treated mice than other control groups (FIG. 17C).

Figure 18:
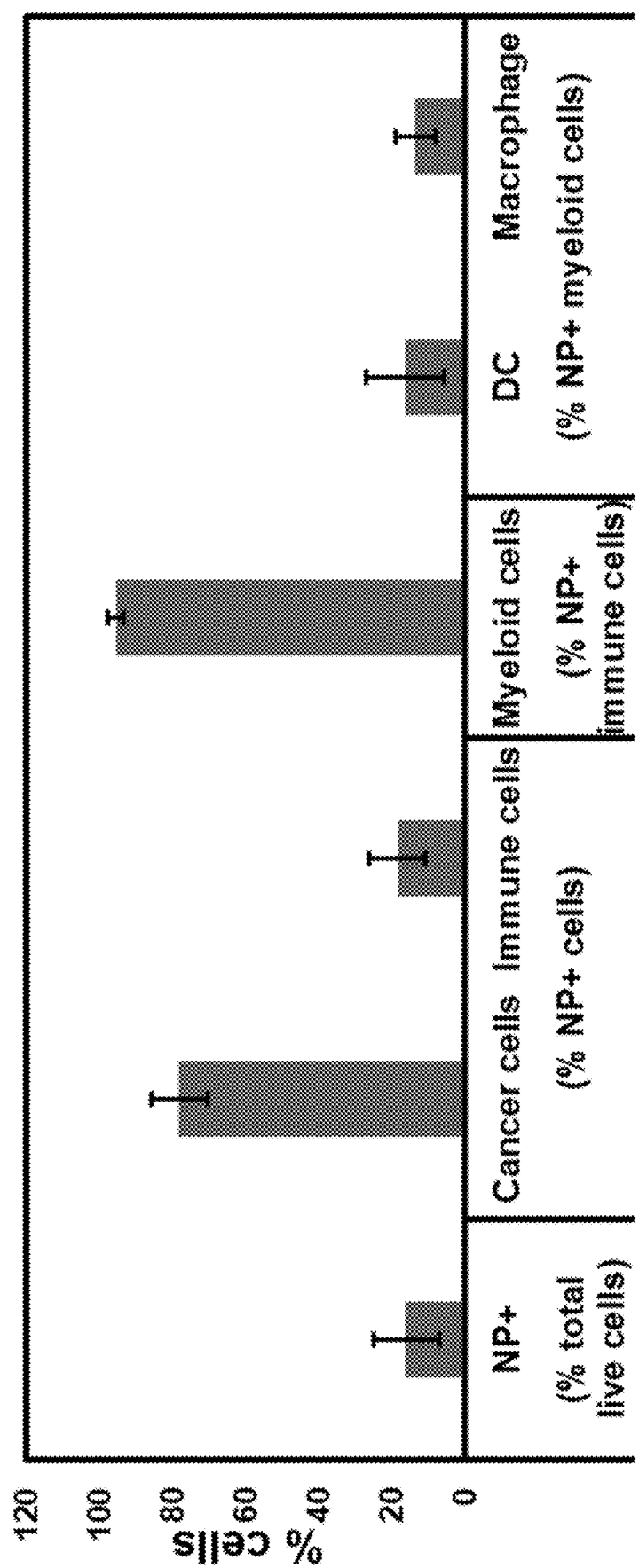
FIG. 18. NP cell uptake in the TME. Mice (same model as in FIG. 7, B16F10 tumor size of ~100 mm$^3$ n=3/group, plotted as mean and SD) were intratumorally injected with Alexa 488-siRNA-CpG-NP. Two hours after injection, cells in the treated tumor were profiled and analyzed for the presence of siRNA-CpG-NP (NP+) in each population.

In a separate experiment, mice were treated (similar model to FIG. 7) by intratumorally injecting siRNA-CpG-NPs (AIRISE-02). siRNA was tagged with Alexa-488. FIG. 18 shows that at two hours after intratumoral injection, siRNA-CpG-NPs were taken up by 15% of cells in the TME, while CpG-siSTAT3 conjugates in prior work were reported to be taken up by only 2% of cells in the TME at 1 and 3 hours after intratumoral injection (Kortylewski et al., Nature biotechnology, 27(10):925-932, 2009). Out of the cells that took up siRNA-CpG-NP, 80% were cancer cells (CD45−), and 20% were immune cells (CD45+), in accordance with our finding that the TME consists of 80-90% cancer cells. In contrast, the aforementioned CpG-siSTAT3 conjugate depends on CpG for processing and is primarily taken up by only TLR9+ cells, and not TLR9− cancer cells. Delivery of siSTAT3 and CpG to both cancer and immune cells is more desirable. Out of the immune cells, myeloid cells (CD45+ CD3−CD19−) took up the most siSTAT3-CpG-NP. These included macrophages (F4/80+) and DCs (CD11c+ MCHII+). NPs were not detected in the distant untreated tumor (not shown), indicating no leachate of NPs to the untreated tumor.

Figure 8A:
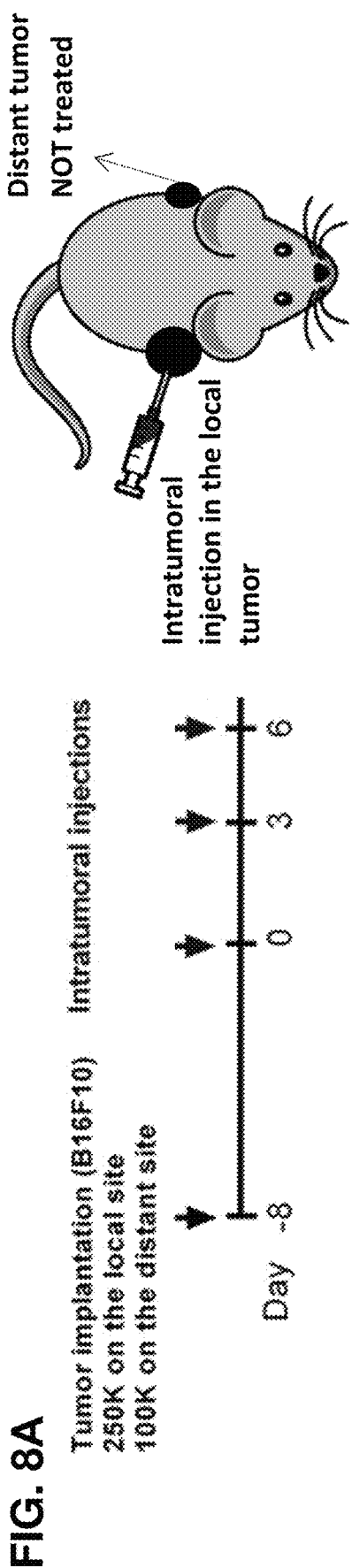
FIGS. 8A-8D. The CD8-dependency of siSTAT3-CpG-NP (AIRISE-02)'s effect. C57/BL6 mice bearing B16F10 tumors were established and treated as in FIG. 8A, and CD8 depleting antibodies (Clone 2.43, BioXcell, 200 μg/mouse, twice weekly, i.p.) were given to a group of mice throughout the entire study, starting 1 day before the first intratumoral treatment of AIRISE-02. CD8 depletion was shown to lessen the efficacy of AIRISE-02 in inhibiting local tumors (FIG. 8B), distant untreated tumors (FIG. 8C), and prolonging the survival of mice (FIG. 8D), indicating that AIRISE-02's effect is immune-dependent rather than directly cytotoxic.
Figure 8B:
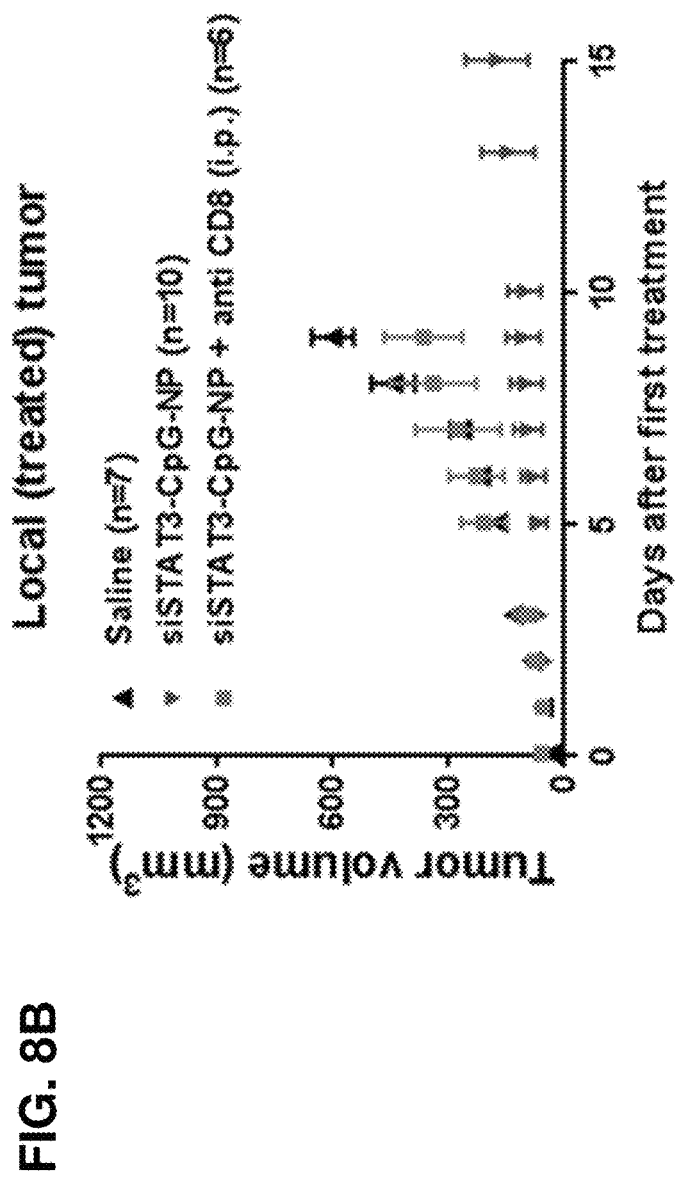
Figure 8C:
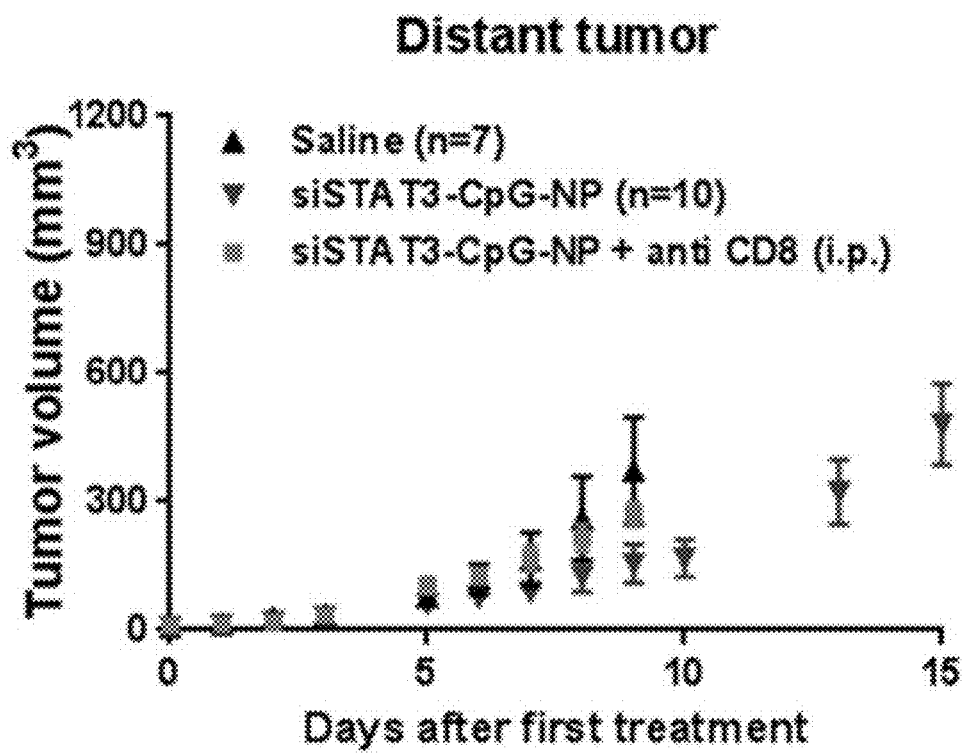
Figure 8D:
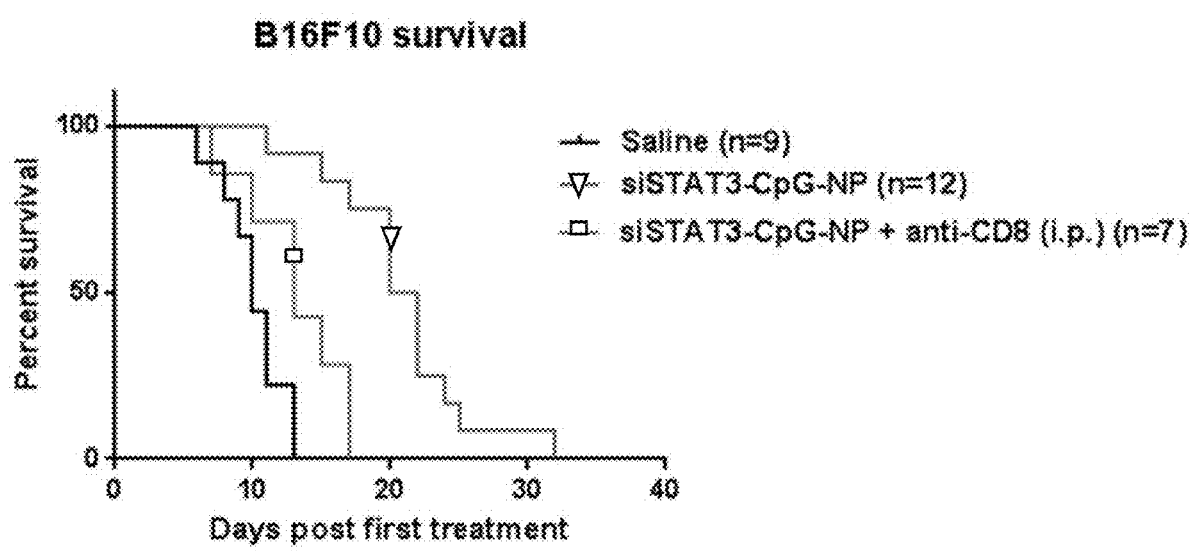

It was also confirmed that the therapeutic action of AIRISE-02 was dependent on the immune response, rather than the direct cytotoxic effect of the therapeutic. When CD8 was depleted from mice (FIG. 8A) using anti-CD8 antibody, the treatment response of siSTAT3-CpG-NP was significantly reduced (FIGS. 8B-8D). This illustrates that the treatment effect was immune-mediated.

Figure 9A:
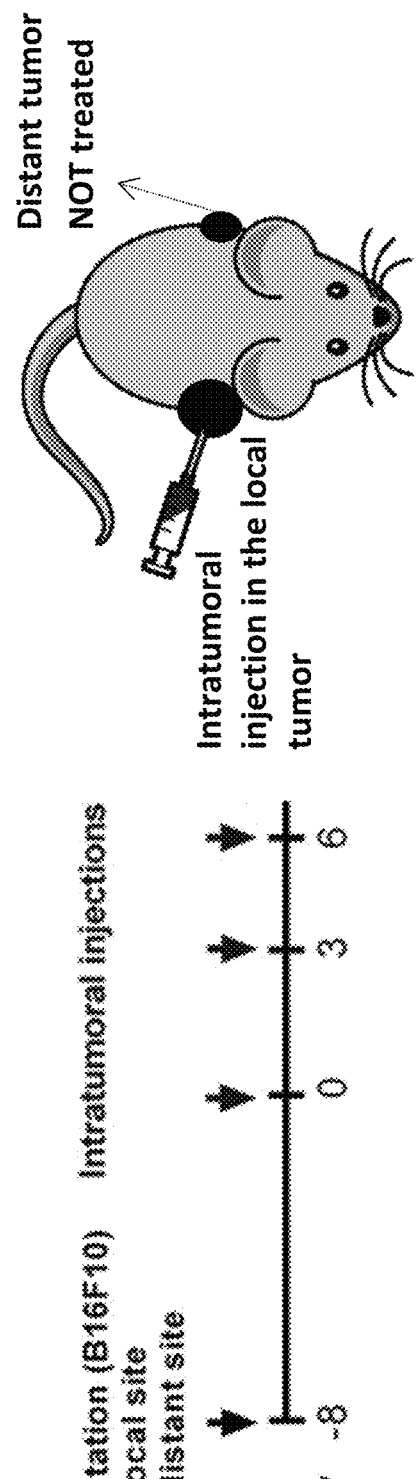
FIGS. 9A-9D. siSTAT3-CpG-NP (AIRISE-02) enhanced the effects of checkpoint inhibitors (PD1 and CTLA4 antibodies). C57/BL6 mice bearing B16F10 tumors were established and treated as in (FIG. 9A). Checkpoint inhibitors (200 μg PD1 mAb/mouse and 100 μg CTLA4 mAb/mouse, i.p.) were given to two groups of mice concurrently with the intratumoral AIRISE-02 in one group and alone in one group (i.e. three doses at three days apart). AIRISE-02 greatly enhanced the effects of checkpoint inhibitor cocktail; the combination controlled both local (FIG. 9B) and distant untreated tumors (FIG. 9C), and prolonged survival of mice (FIG. 9D) better than AIRISE-02 or checkpoint inhibitor cocktail alone. 5 out of 8 mice receiving the combination were cured (tumor-free).
Figure 9B:
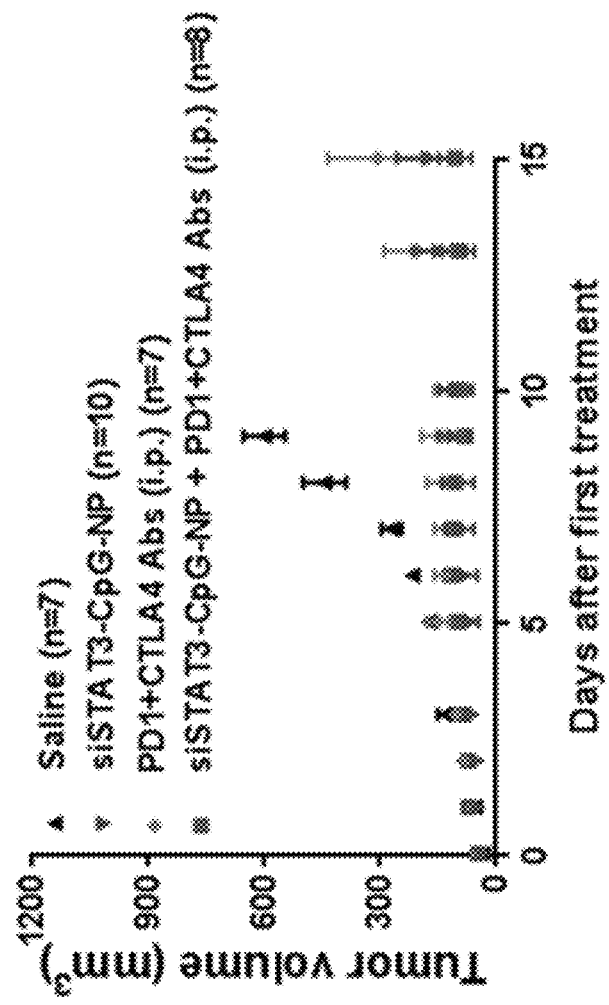
Figure 9C:
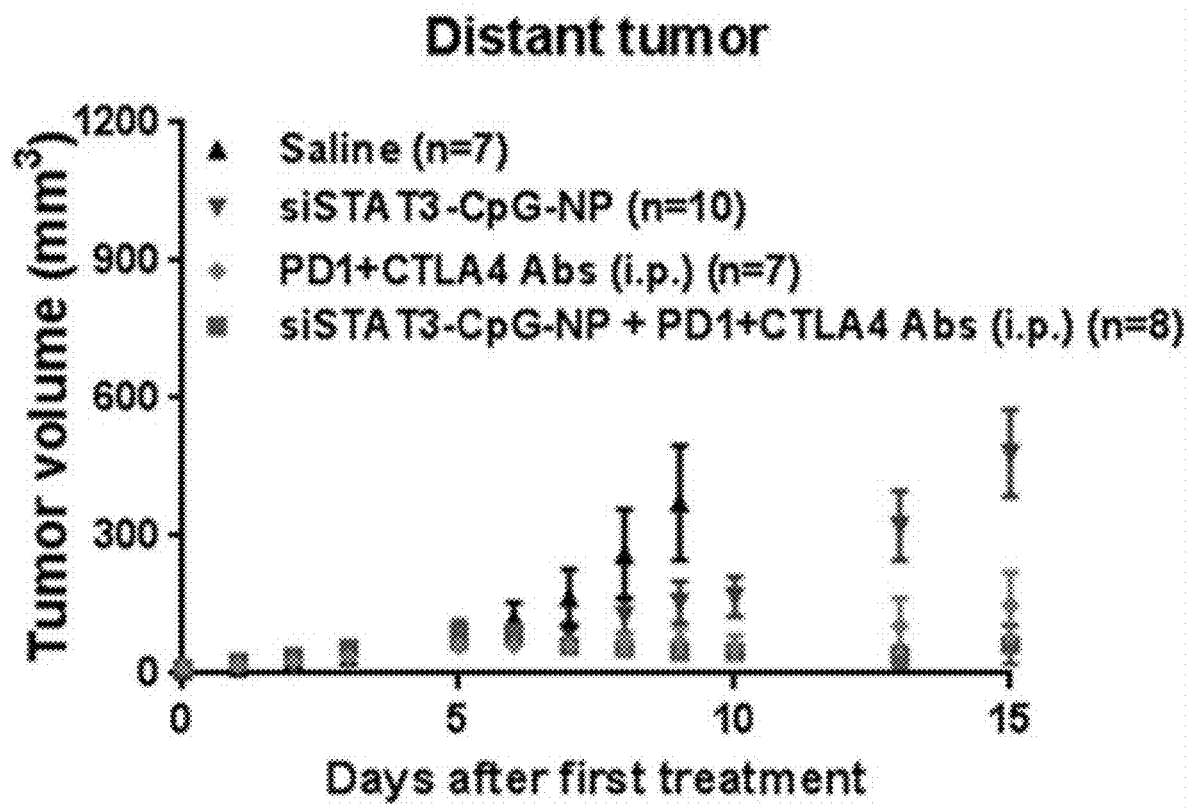
Figure 9D:
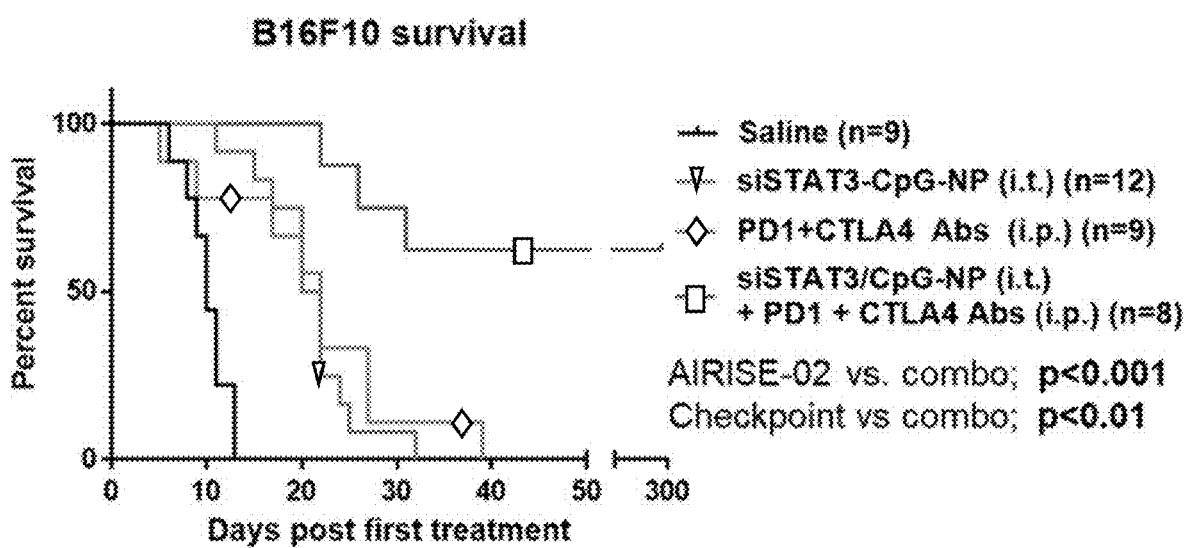

Moreover, since NP treatment generates more CD8+ T cell repertoires, it is proposed that this treatment can be beneficially combined with checkpoint inhibitor treatment to enhance anti-cancer effects. This was tested by using siSTAT3-CpG-NP (AIRISE-02, FIG. 9A) with two checkpoint inhibitors (anti-PD-1 and anti-CTLA4 antibodies) that are current in use in clinics. NP treatment (intratumorally into only one of the two tumors) has similar efficacy to the checkpoint inhibitor cocktail (given intraperitoneally) in terms of survival (FIG. 9D). The combination of AIRISE-02 and checkpoint inhibitor cocktails substantially improved the efficacy in terms of controlling local (FIG. 9B) and distant tumors (FIG. 9C) as well as mouse survival (FIG. 9D). Remarkably, a complete cure in 5 out of 8 mice (which remain tumor-free for 10 months to-date) was achieved, while no mice were cured with AIRISE-02 or ICIs alone (FIG. 10C). Curative effect in B16F10 model is considered impressive because this model is known to be aggressive in literature, and no curative effect is found in prior CpG-based vaccine+ICIs, when treatment started a week after tumor implantation (curative effect is sometimes reported in prophylactic settings). In another set of mice that were cured, a tumor rechallenge was performed by implanting B16F10 cells 3 months after the last treatment. The cured mice rejected the cancer from growing, suggesting successful long-lasting anti-tumor effect (memory effect) of AIRISE+ ICIs.

Systemic Co-Delivery of CpG Oligo and SiSTAT3 on NP Prolonged Survival in Mice, Suggesting Potential Immune Priming and Activation.

Figure 10A:
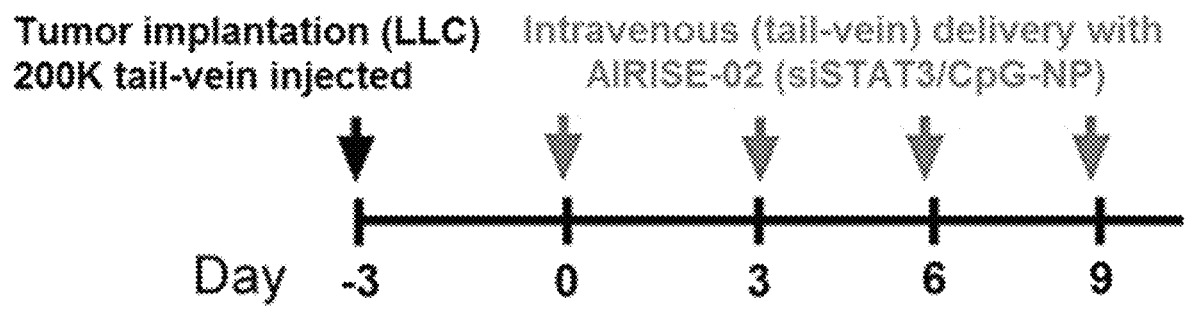
FIGS. 10A-10B. siSTAT3-CpG-NP (AIRISE-02) prolonged survival of mice bearing experimental metastatic lung tumors. C57/BL6 mice was injected (via tail vein) with 200,000 Lewis Lung Carcinoma (LLC-JSP) cells resulting in lung cancer establishment in lung of the mice. Treatments were given intravenously as shown in (FIG. 10A). Survival was significantly prolonged with intravenous AIRISE-02 as shown in (FIG. 10B).
Figure 10B:
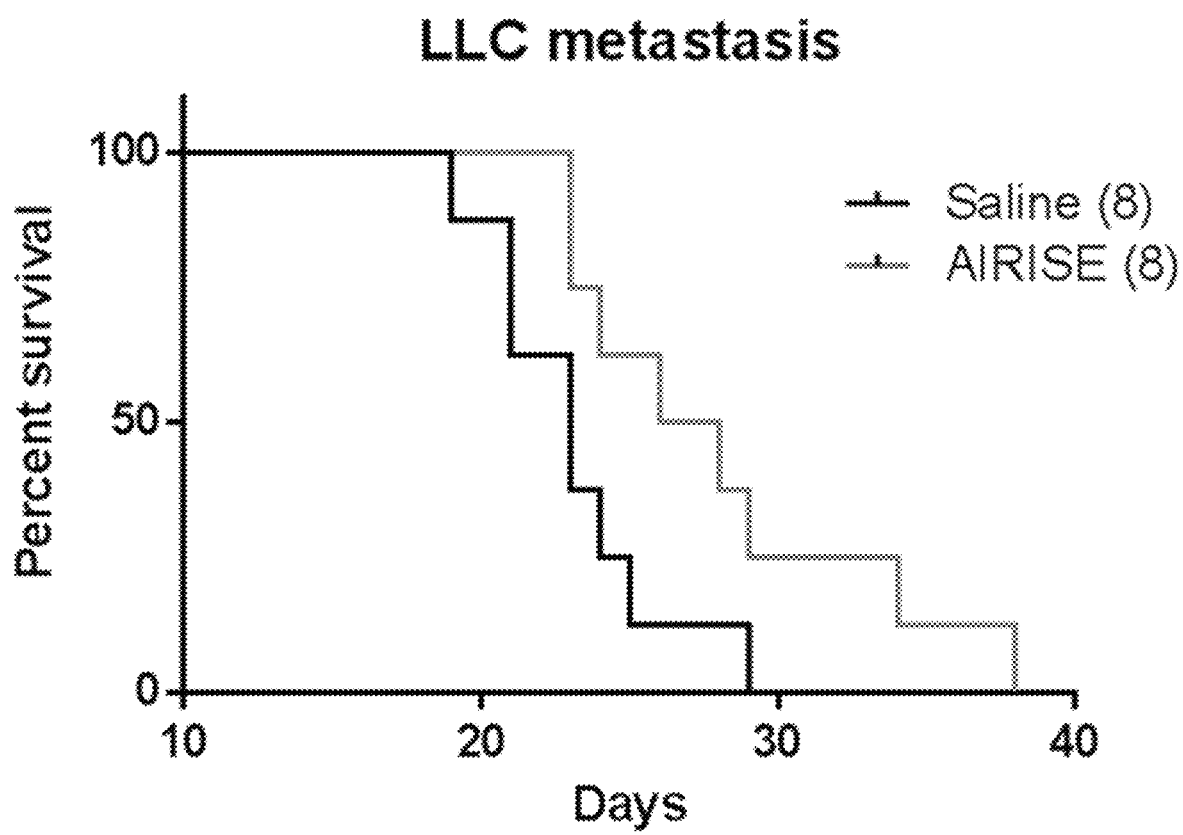

In addition to intratumoral administration, AIRISE-02 can be given systemically to treat cancer that is not easily accessible for intratumoral injection, such as lung cancer. FIG. 10A shows the treatment schedule of AIRISE-02 via tail vein in mice bearing Lewis Lung Carcinoma (LLC-JSP) tumors. Prolonged survival was observed (FIG. 10B), suggesting successful anti-cancer immunotherapy effect.

Figure 11C:
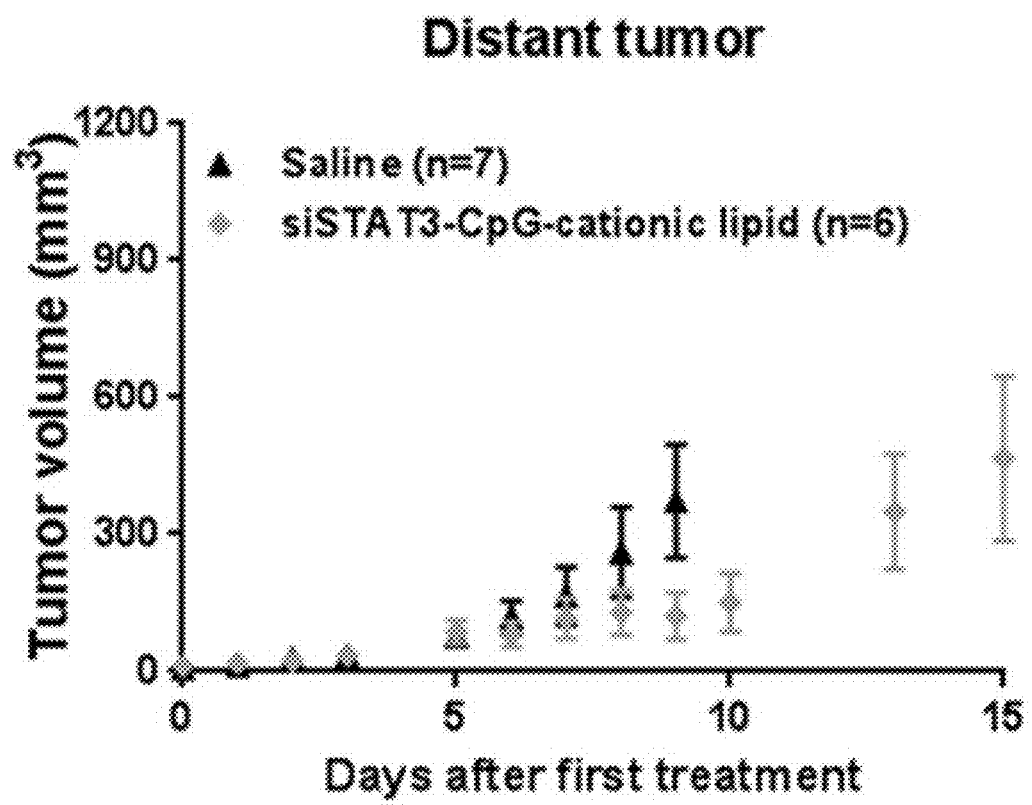

Intratumoral Codelivery of CpG Oligo and siSTAT3 by Cationic Lipid Also Induces In Situ Tumor Vaccination.

siSTAT3 and CpG was mixed with cationic lipid (Dharmafect® from Dharmacon®) to form lipid nanoparticles, which were administered to mice in the same manner as FIG. 7. FIGS. 11A-11C show that a very similar response was achieved with cationic lipid as had been observed with mesoporous silica nanoparticles (FIG. 7). This illustrates that, for intratumoral injection, diverse types of nanoparticles can be used to create the therapeutics with the cargo combinations described herein.

Figure 12A:
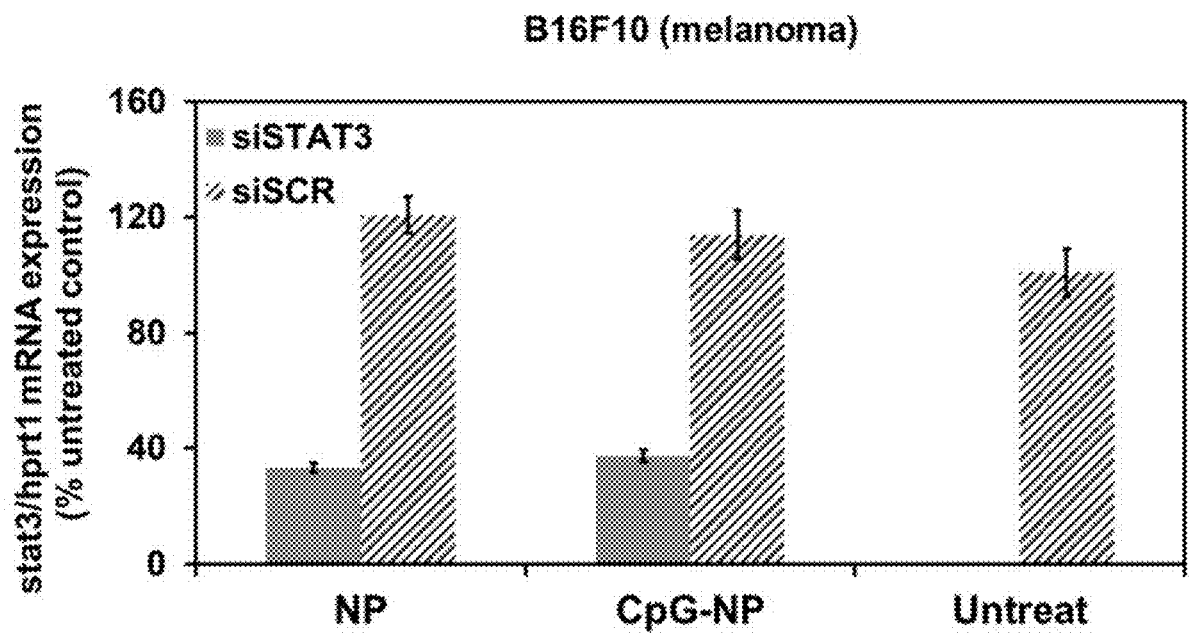
FIGS. 12A-12C. NP-mediated co-delivery of siRNAs and CpG to cancer and immune cells. B16F10 (FIG. 12A) and J774 (FIG. 12B) cells (both were mouse cell lines) and (FIG. 12C) dendritic cells harvested from bone marrow of C3H/HEJ mice (BMDC) were treated with NP or CpG loaded NP (CpG-NP) carrying siRNA against STAT3 or scrambled siRNA (siSCR). Dose of each siRNA was 50 nM and at 2.0 wt. % of NP, and dose of CpG was 2 wt. % of NP for B16F10 and J774 and 4 wt % of NP for BMDC. mRNA was analyzed with qRT-PCR at 48 h post-treatment. Data indicate the efficacy of nanoparticle to transfect siRNA (e.g., siSTAT3) in both cancer and immune cells, which was not highly affected by CpG loaded on the NP. Unless otherwise noted throughout the examples, "NP" denotes mesoporous silica nanoparticles coated with cross-linked PEI and PEG as described in Ngamcherdtrakul et al., Advanced Functional Materials, 25(18):2646-2659, 2015 and U.S. Patent Application Publication No. 2017/0173169.
Figure 12B:
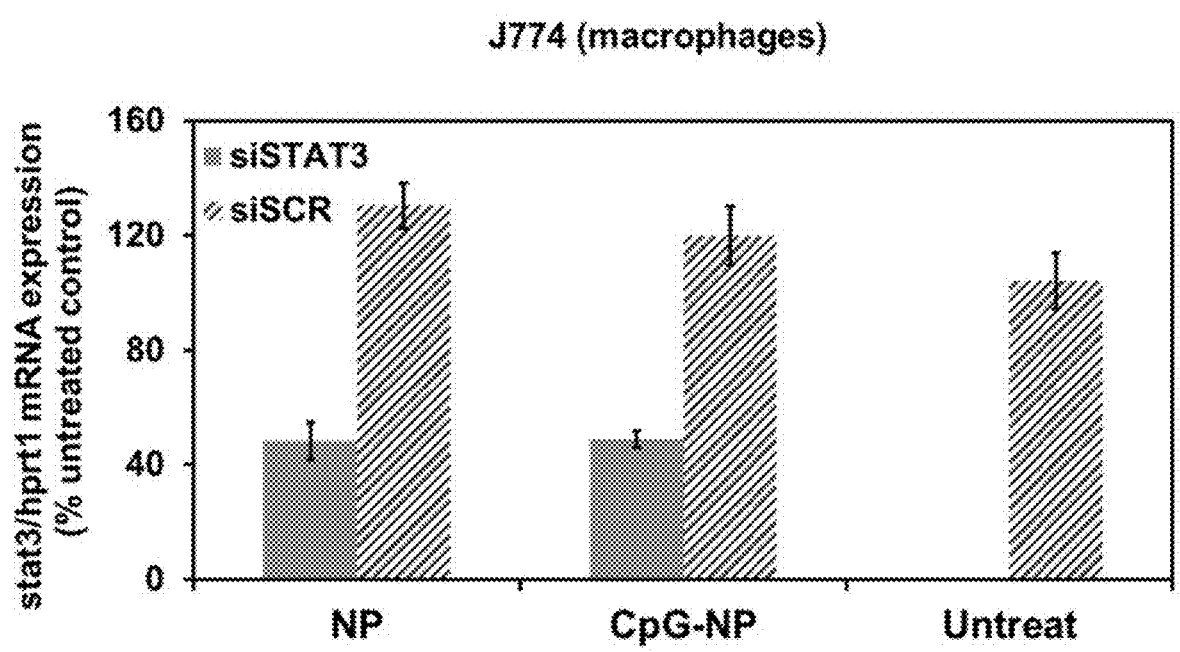
Figure 12C:
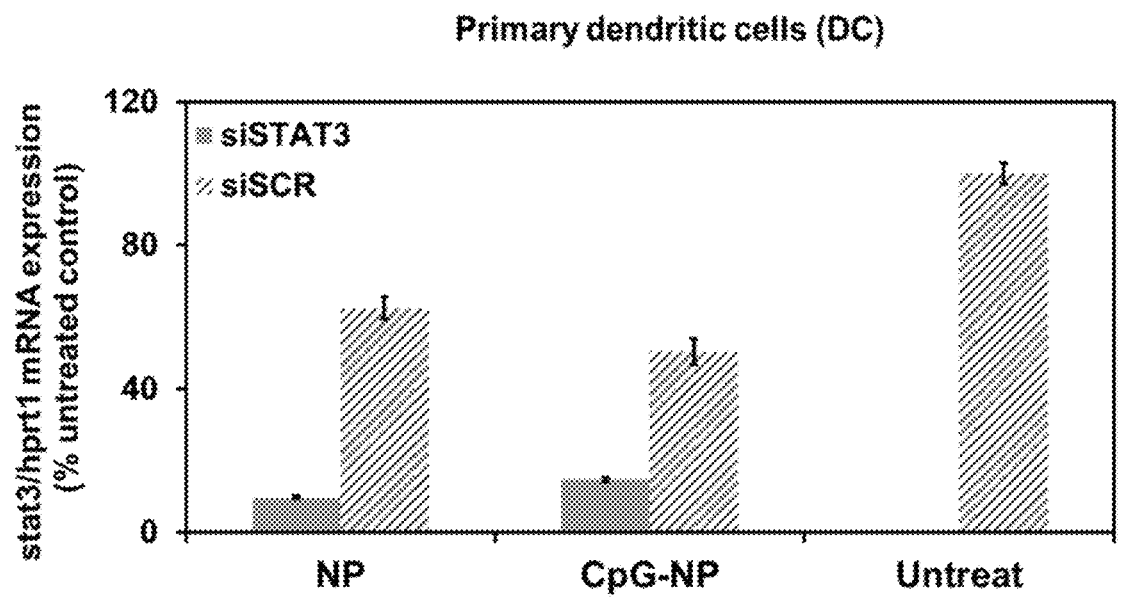
Figure 19:
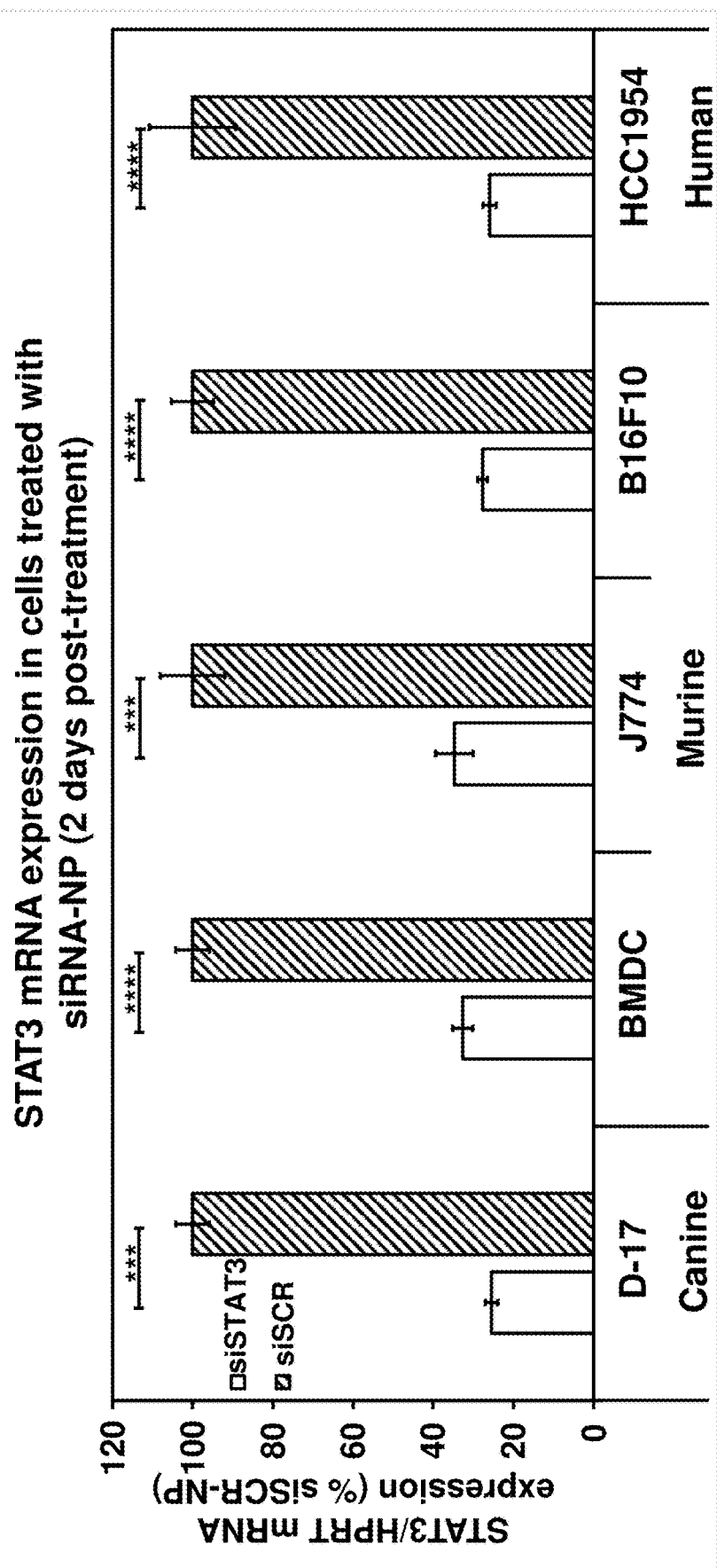
FIG. 19. siSTAT3-NP can knock down STAT3 in multiple cells of multiple species. D-17 (dog osteosarcoma), BMDC (Bone-marrow derived dendritic cells from mice), J774 (mouse macrophage), B16F10 (mouse melanoma), and HCC1954 (human breast cancer) were treated with siSTAT3-NP (50 nM) for 48 hours. qRT-PCR analysis for STAT3 and HPRT mRNA was performed with primers of corresponding species. A single siSTAT3 sequence was used throughout. siSCR=scrambled siRNA control. *$p<0.001$; **$p<0.0001$.
Figure 34A:
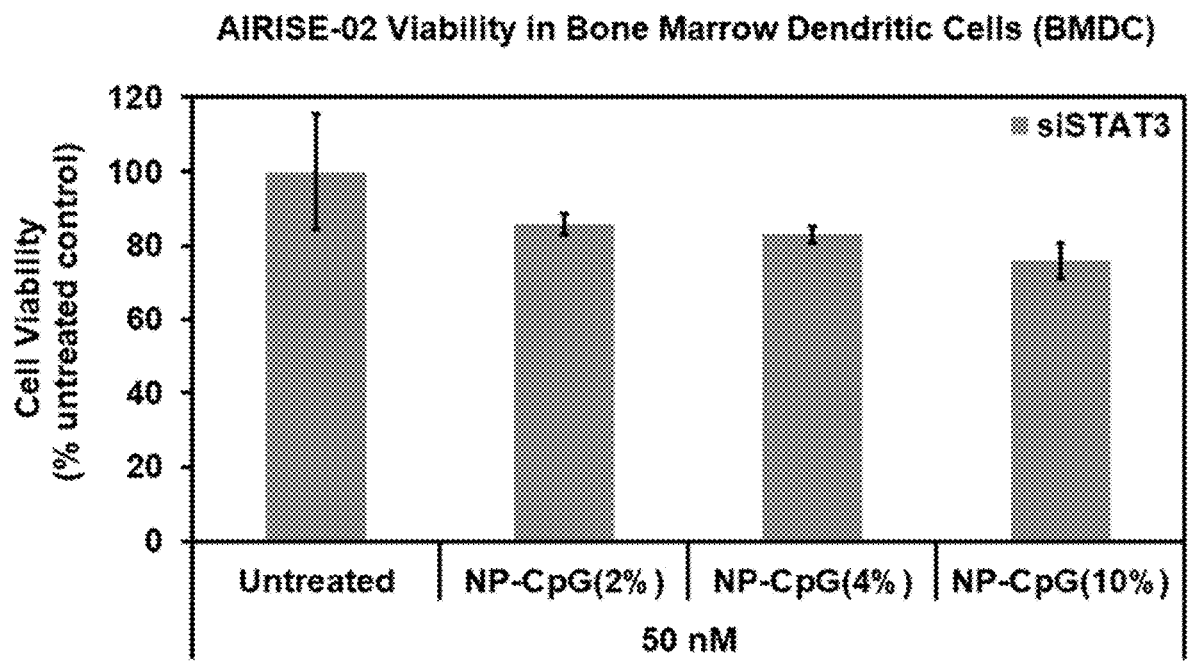
FIGS. 34A-34B. Viability of mouse (FIG. 34A) bone marrow derived dendritic cells and (FIG. 34B) J774 cells, 2 days after treatment with AIRISE-02 containing different amount of CpG and 2 wt % siSTAT3. Dose: 50 nM siRNA.
Figure 34B:
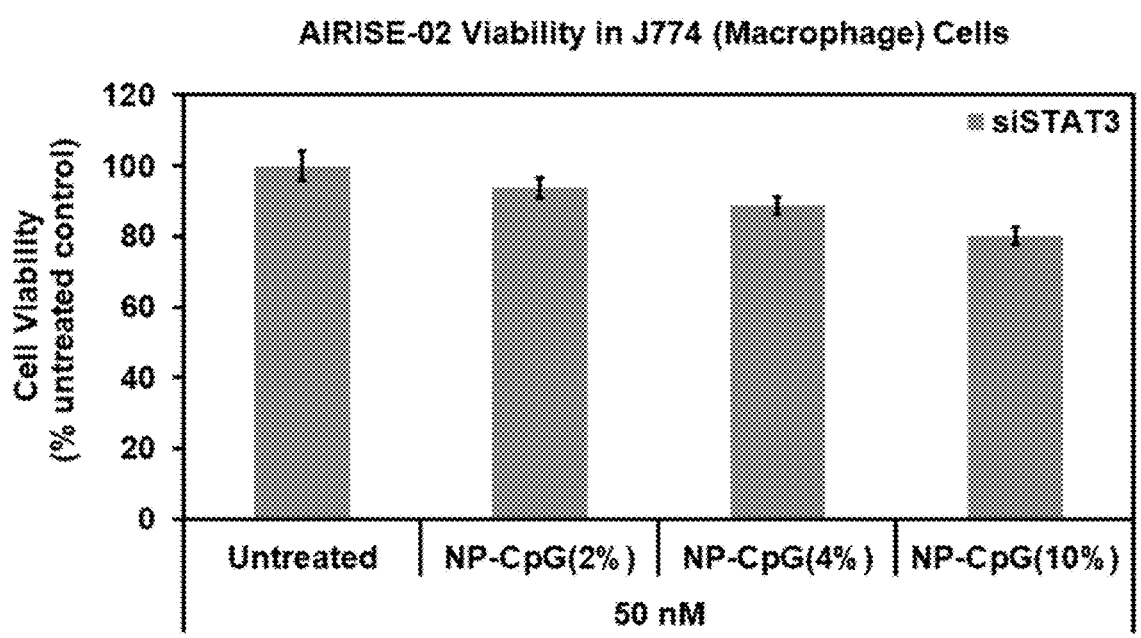
Figure 35:
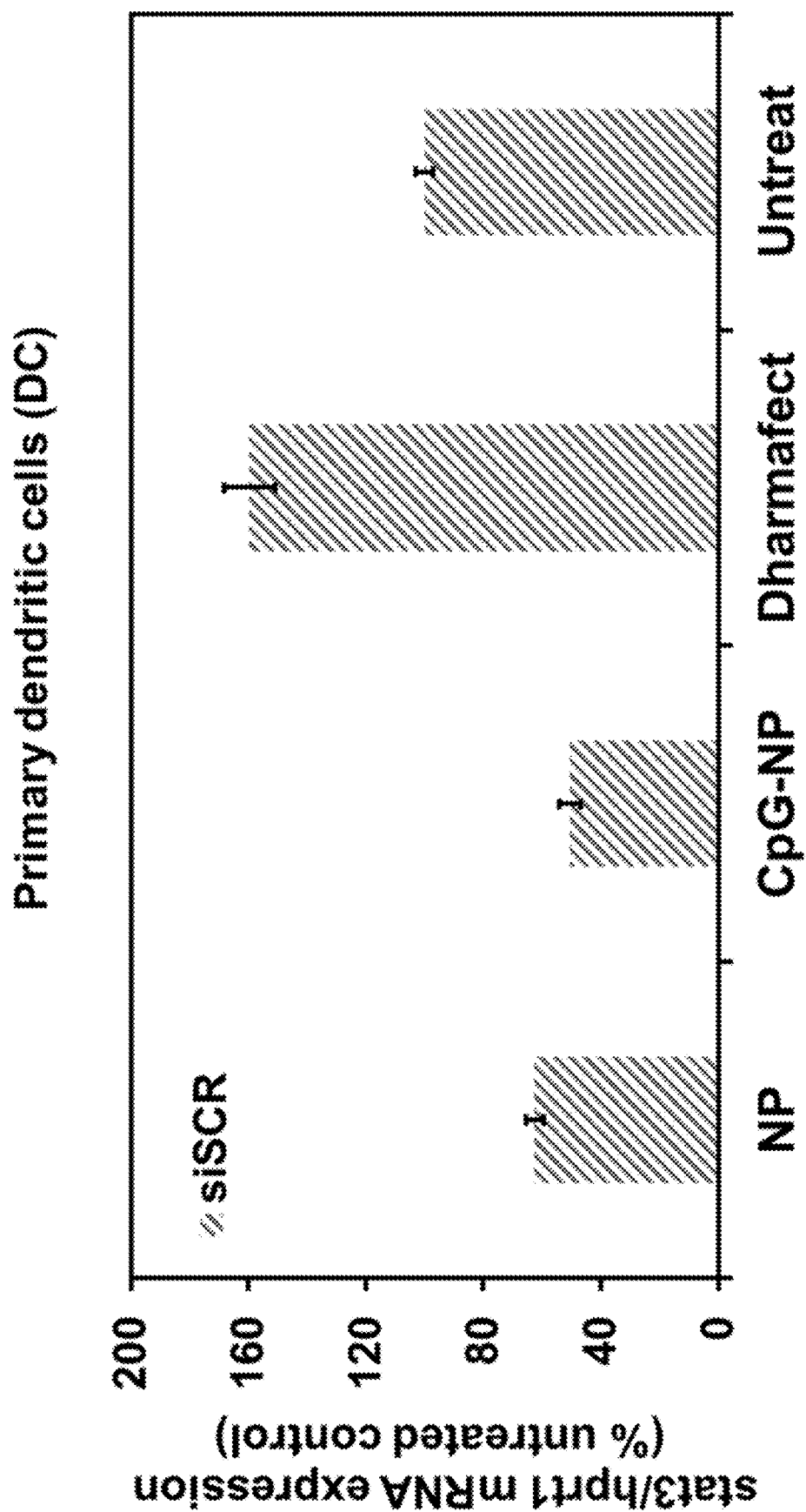
FIG. 35. Co-delivery of non-targeting scrambled siRNA (siSCR) and CpG by NP or Dharmafect® to dendritic cells harvested from C3H/HEJ mice. Dose of each siRNA was 50 nM and at 2.0 wt. % of NP, and dose of CpG was 4 wt. % of NP. siRNA-Dharmafect® formulation was prepared following the manufacturer's protocol. mRNA was analyzed with qRT-PCR at 48 h post-treatment. "NP" denotes mesoporous silica nanoparticles coated with cross-linked PEI and PEG as described in Ngamcherdtrakul et al., *Advanced Functional Materials*, 25(18):2646-2659, 2015 and U.S. Patent Application Publication No. 2017/0173169.

NP can deliver siRNA along with CpG to both cancer and immune cells, resulting in knockdown of the target gene. NP can deliver siRNA to both cancer and immune cells and knock down STAT3 gene (as an example) as shown in FIG. 12A for B16F10 cancer cells, FIG. 12B for J774 macrophage, and FIG. 12C for mouse primary DCs. Interestingly, it was found that siSCR-NP also decreased STAT3 level (see FIG. 12C vs. untreated) in DCs. This was not caused by nanoparticle toxicity since the cell viability was unchanged versus untreated control (FIG. 34), and STAT3 mRNA was normalized with housekeeping mRNA. Without being bound to any explanation, it is proposed that this may be due to the antioxidant property of mesoporous silica nanoparticle because antioxidants were previously reported to counteract immunosuppressive pathways, including STAT3 activation (Yoon et al., *Autophagy*, 6(8):1125-1138, 2010). On the other hand, it was found that Dharmafect® (a commercial transfection agent based on cationic lipid (non-antioxidant) by Horizon Discovery) increased STAT3 expression in DCs (FIG. 35), which may lead to undesirable immunosuppressive TME. This suggests that the use of the antioxidant mesoporous silica nanoparticle platform described in Ngamcherdtrakul et al., *Advanced Functional Materials*, 25(18): 2646-2659, 2015 may be advantageous over lipid nanoparticles for controlling STAT3-mediated pathways. FIG. 19 also shows that STAT3 is so conserved that the same siSTAT3 sequence can knock down STAT3 in canine, murine, and human cells, facilitating direct translation from murine studies to dog and human studies. Hence, the same siSTAT3 sequence was used throughout the application across species.

The ability to transfect cancer cells, DCs, and macrophages and reduce certain genes such as STAT3, suggest that the immunotherapeutic constructs described herein can be used for ex vivo engineering of immune cells. Such ex vivo engineered immune cells can be administered back to patients for therapeutic effect and immune response (e.g., to kill cancer cells). The cells can be derived from the treated patients or from different healthy donors (e.g., stem cells and their derivatives—Senju et al., *Int J Hematol*, 91(3):392-400, 2010). Cancer cells may be treated with our immunotherapeutic construct ex vivo (with or without additional agents) to create a whole cell cancer vaccine (Keenan et al., *Int J Hematol*, 91(3):392-400, 2010; Goldstein et al., *Int J Hematol*, 117:118-127, 2011).

Figure 20:
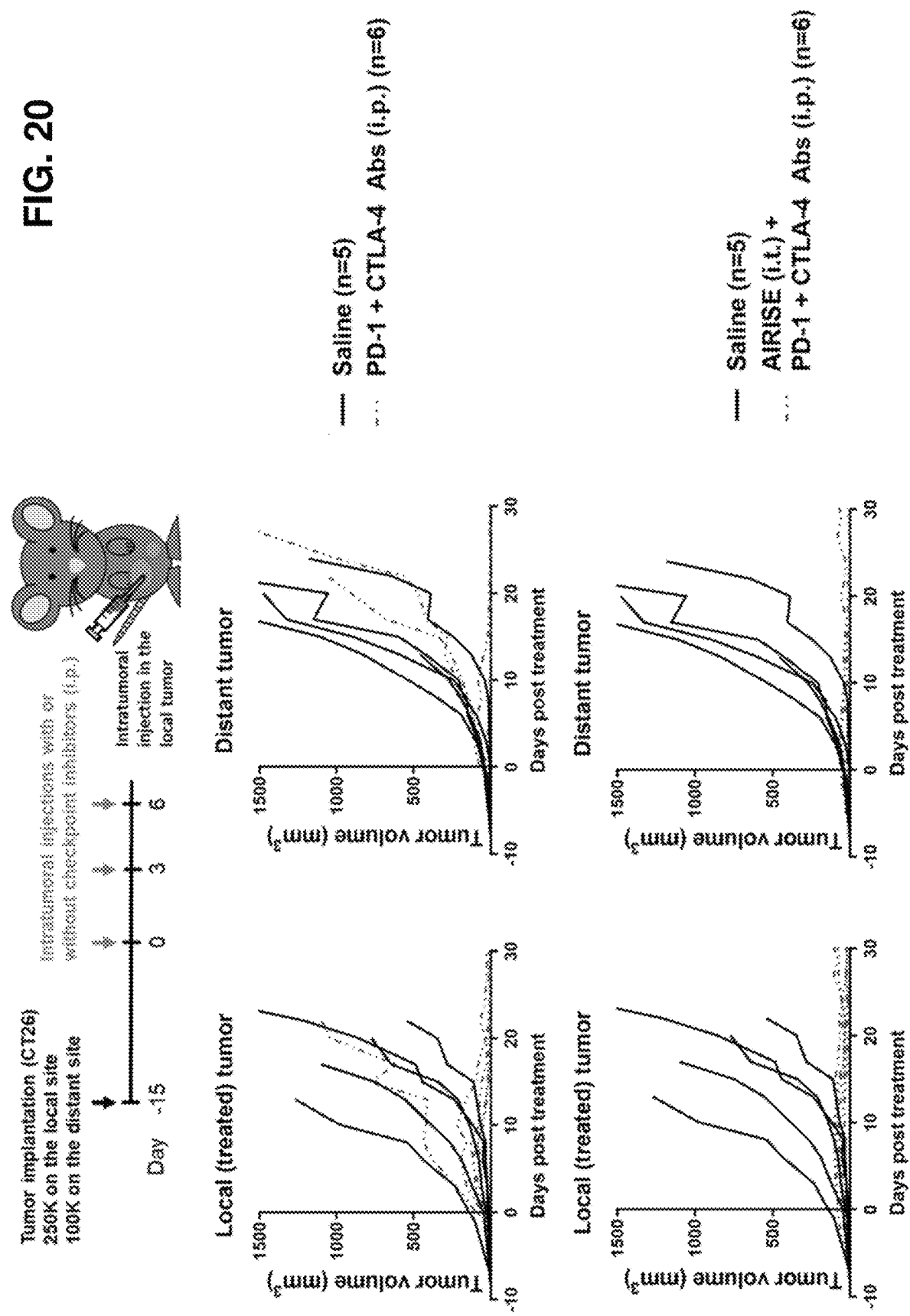
FIG. 20. AIRISE-02 (siSTAT3-CpG-NP)+ICIs resulted in complete response in mice bearing CT26 bilateral tumors. 250K and 100K CT26 cells were implanted into bilateral abdomens of each mouse (Balb/c). 15 days after tumor implantation, mice were treated as outlined. Tumor growth curves of local treated tumors and distant untreated tumors are plotted as spider plots (each line represents an individual mouse). Dose of injection: 16 μg CpG; 5 μg siSTAT3; 0.25 mg NP. Checkpoint inhibitors (200 μg PD1 mAb/mouse and 100 μg CTLA4 mAb/mouse, i.p.) were given to two groups of mice concurrently with the intratumoral AIRISE-02 in one group and alone in one group.
Figure 21:
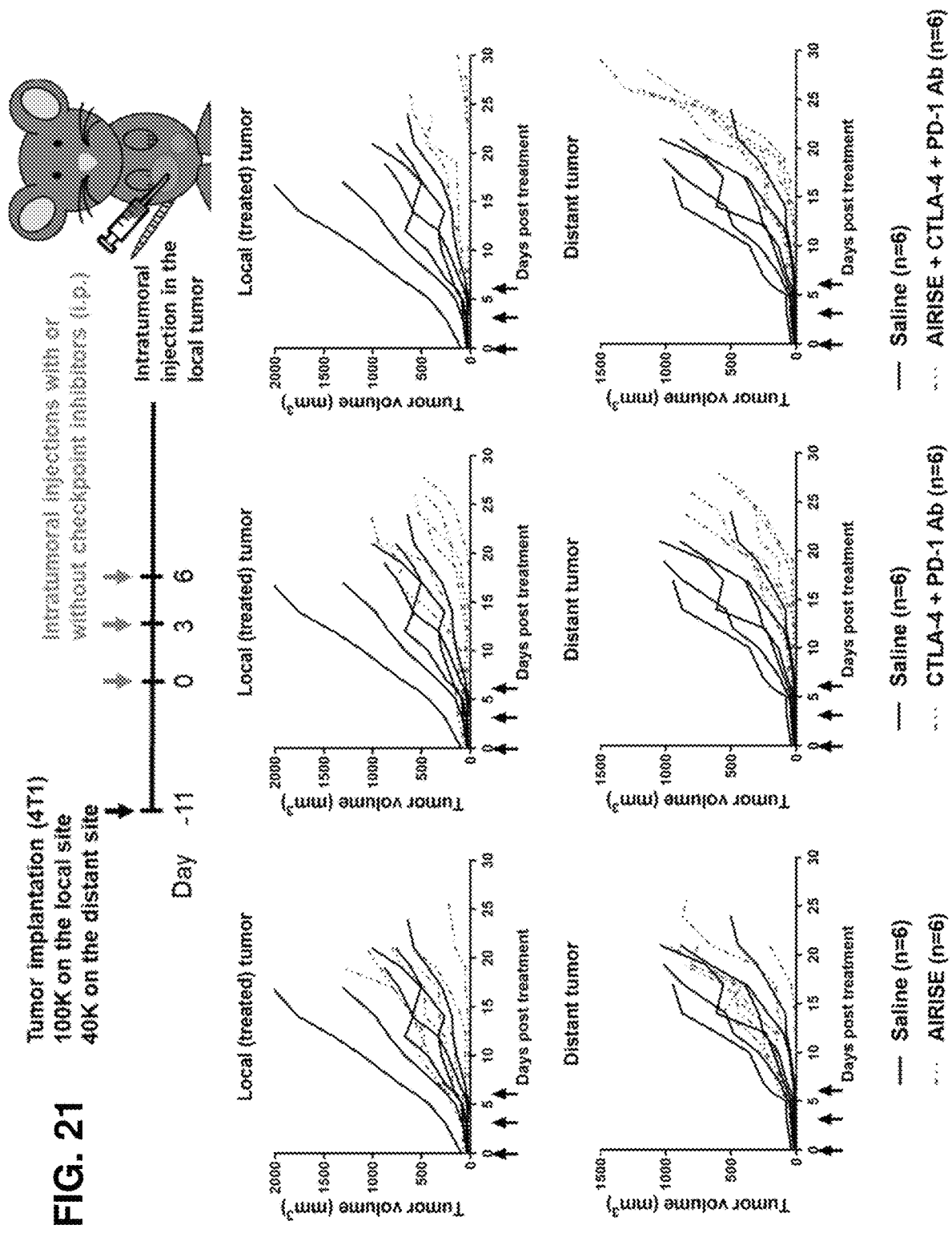
FIG. 21. AIRISE-02 (siSTAT3-CpG-NP)+ICIs are also effective in mice bearing aggressive 4T1 breast bilateral tumors. 100K and 40K 4T1 cells were implanted into bilateral mammary fat pads of each mouse (Balb/c). 11 days after tumor implantation, mice were treated as outlined. Tumor growth curves of local treated tumors and distant untreated tumors are plotted as spider plots (each line represents individual mouse). Dose is the same as FIG. 20.
Figure 22:
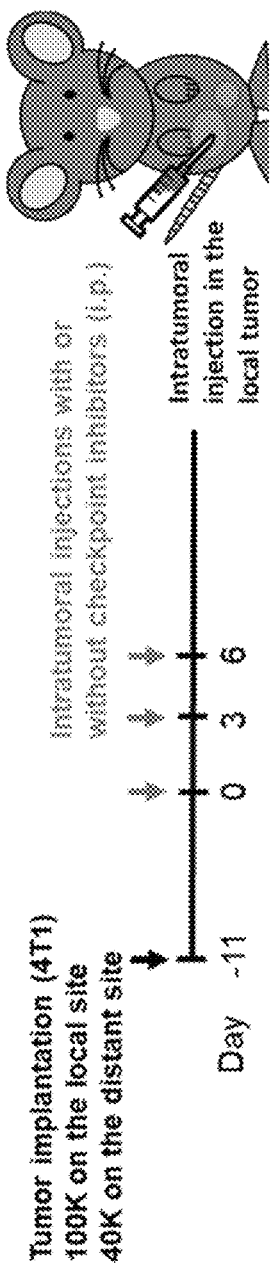
FIG. 22. Survival curve of mice in FIG. 21.
Figure 22:
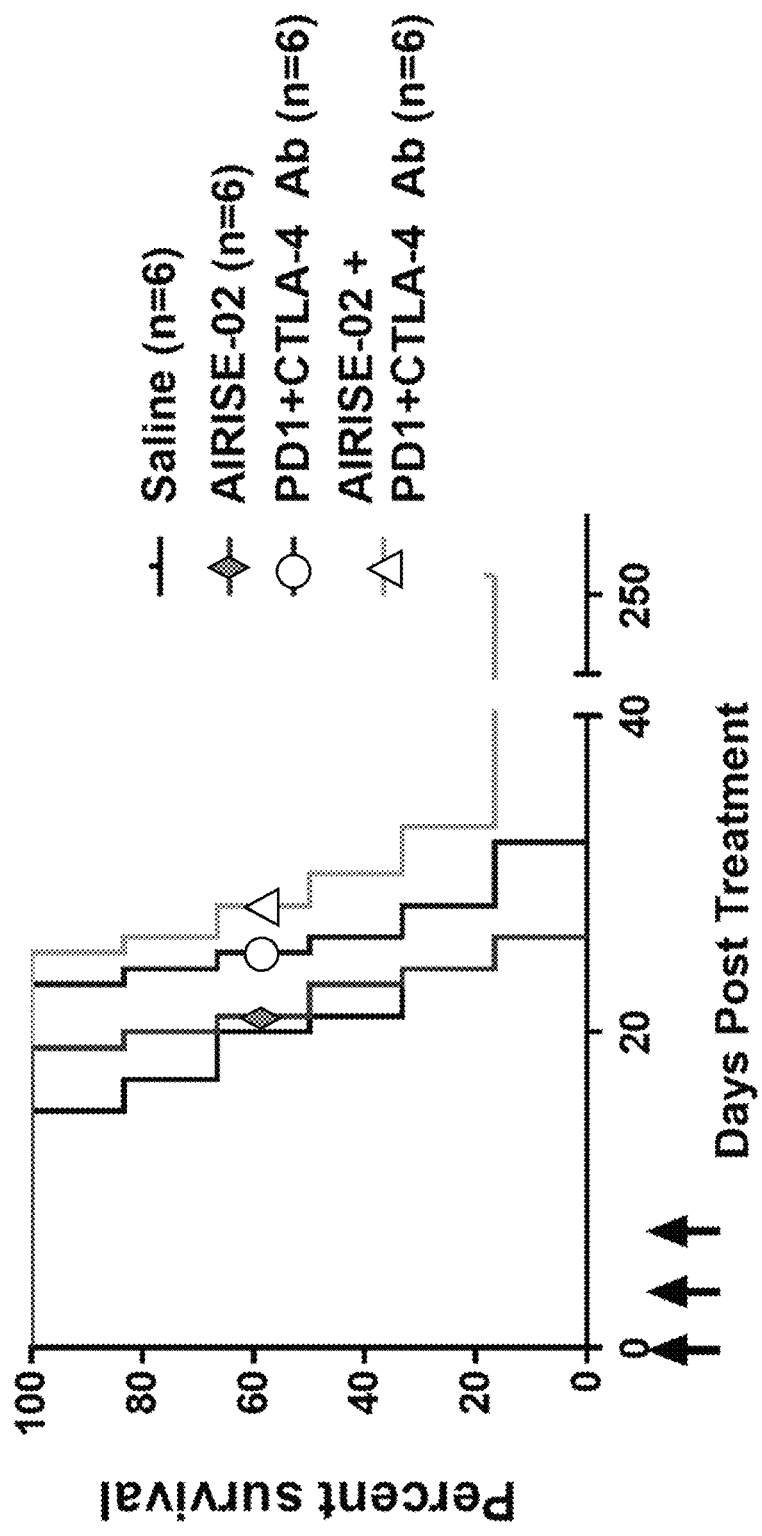

It was also found that AIRISE-02 (siSTAT3-CpG-NP) has efficacy in other tumor models, including colon cancer (FIG. 20) and breast cancer (FIGS. 21&22). In particular, we show that in these two models, combining ICIs (given systemically i.p.) and AIRISE given locally into one of the two tumors in each mouse provides better efficacy than either AIRISE alone or ICIs alone.

Figure 23:
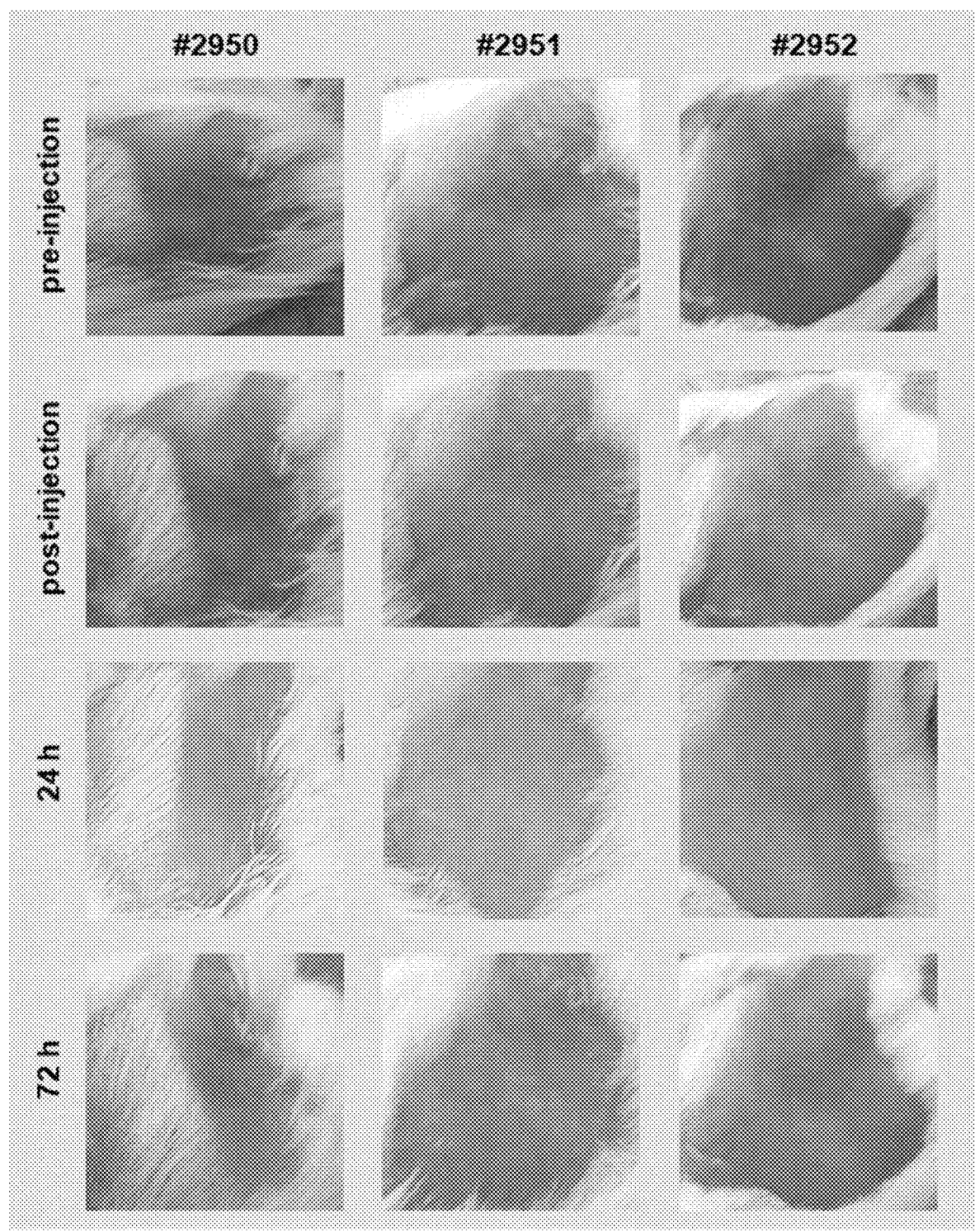
FIG. 23. Safety profile of siSTAT3-CpG-NP (AIRISE-02). AIRISE-02 was administered intramuscularly to three female Balb/c mice. Mice were depilated and injected once in the caudal thigh muscle. Images of the injection site were taken pre-injection, post-injection, 24 hours post-injection, and 72-post injection. Dose of injection: 16 µg CpG; 5 µg siSTAT3; 0.25 mg NP.
Figures 24A, 24B:
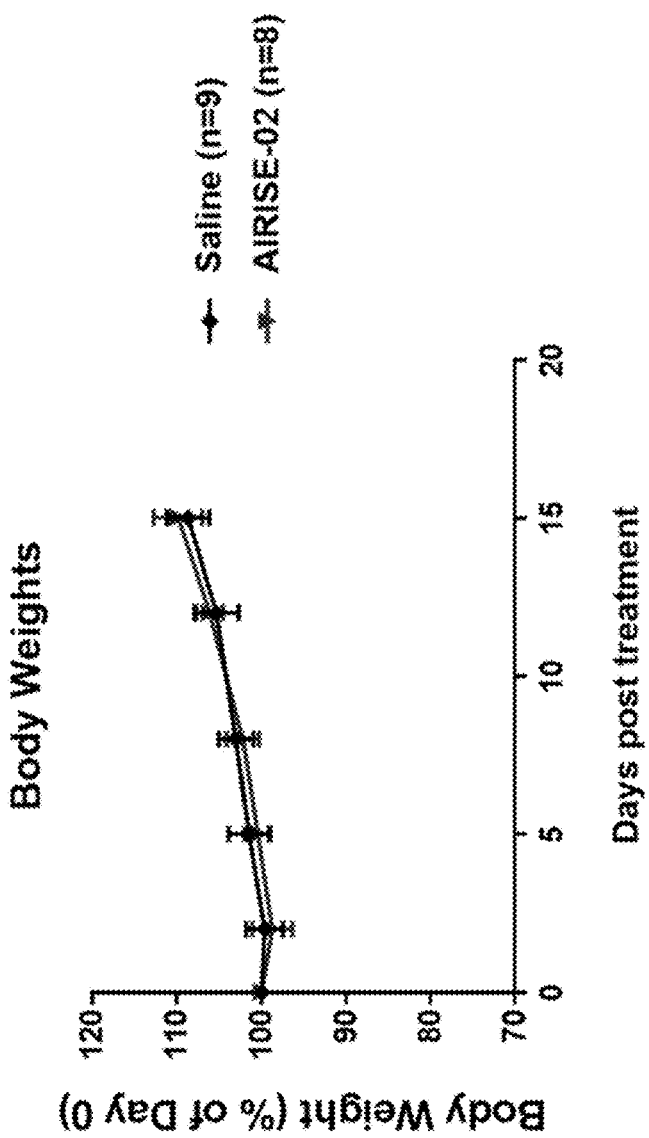
FIGS. 24A-24B. Safety profile of AIRISE-02 in mice. Mice (Balb/c) bearing bilateral MM3MG-HER2d16 tumors implanted in mammary fat pads (as described in Tsao et al., JCI Insight, 4(24):e131882, 2019) were treated with AIRISE-02 by intratumoral injection into one of the two tumors in each mouse 5 times over two weeks. Body weight is monitored as shown in (FIG. 24A); Mice were euthanized when the tumor exceeded 2 cm in diameter or when the mice exhibited signs of pain or distress (15-55 days after treatment). Upon euthanasia, blood were collected and processed into serum. Serum biomarker was measured by Beckman AU680 (IDEXX BioAnalytics, West Sacramento, Calif.) and reported in (FIG. 24B). Dose is the same as FIG. 20
Figure 25:
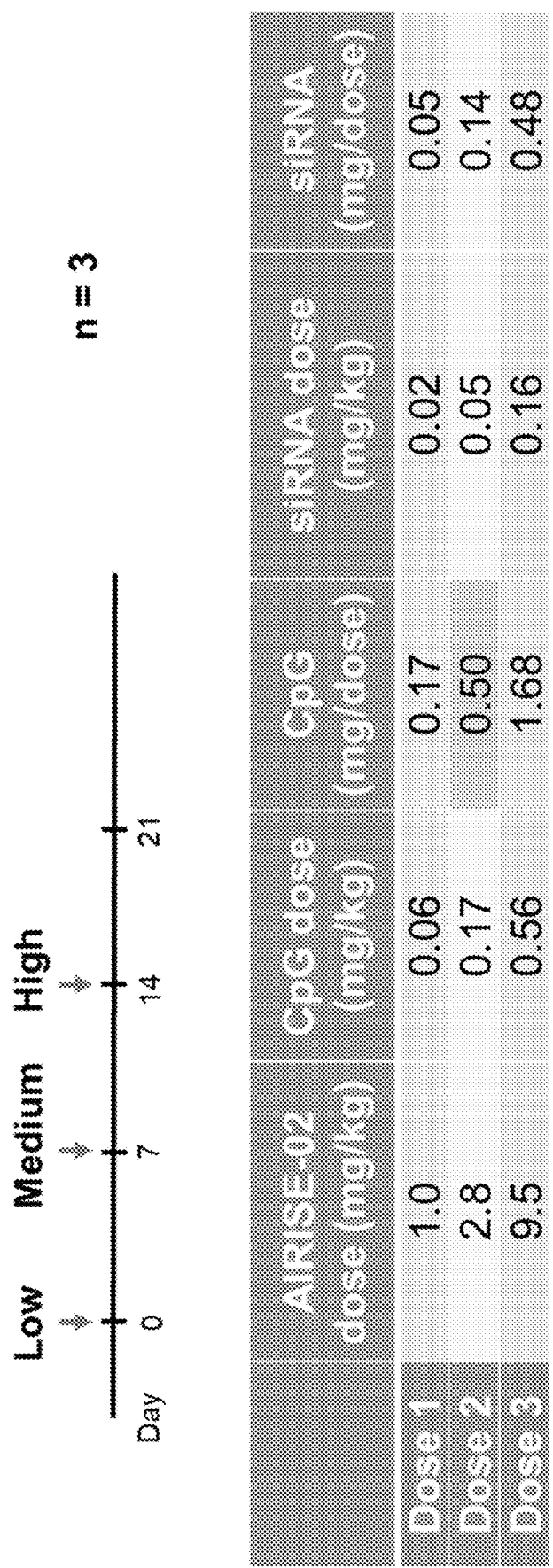
FIG. 25. Schematic describing safety profile of AIRISE-02 in Cynomolgus monkey. Cynomolgus monkey (~2 years old, 3.1±0.2 kg, n=3) was subcutaneously injected with AIRISE-02 at three escalating doses as described in the table. CpG 7909/2006 (human sequence) was used (SEQ ID NO: 8). Body weight, food consumption, cage-side and detailed observations, mortality, morbidity, reaction at the injection site, PK, clinical pathology, cytokine levels, complement split products, and anti-drug antibody were monitored.

Safety profiles of AIRISE-02. AIRISE safety was evaluated in both mice and monkeys. It was found intramuscular injection of AIRISE-02 to mice did not cause toxicity to mouse skin (no edema nor erythema, FIG. 23). There was also no change in body weight and serum biomarkers for kidney and liver function (FIG. 24) when mice were treated with AIRISE-02 vs. treated with saline. AIRISE-02 was also tested in monkeys and found to be safe. Specifically, AIRISE-02 was given subcutaneously to Cynomolgus monkeys in a dose escalating manner (1, 2.8, and 9.5 mg/kg, n=3 animals per group, FIG. 25) at one week apart. All three animals survived to the scheduled study termination. There were no test article-related effects on clinical observations. In term of dermal observations, for low dose, there was no article-related dermal observations; for medium dose, test article-related edema (grades 2-3) was noted at the 48 and/or 72-hour post-dosing, but resolved 7 days after; for high dose, test article-related edema (grades 1-3) and erythema (grade 1) were noted in all animals beginning as early as 24-hour post-dosing and continuing through 7 days (the last observation) but not of concern. There were no test article-related effects on body weight. There were no test article-related effects on hematology parameters. There were no test article-related effects on coagulation parameters. There were no test article-related effects on clinical chemistry parameters.

Example 2

Figure 13:
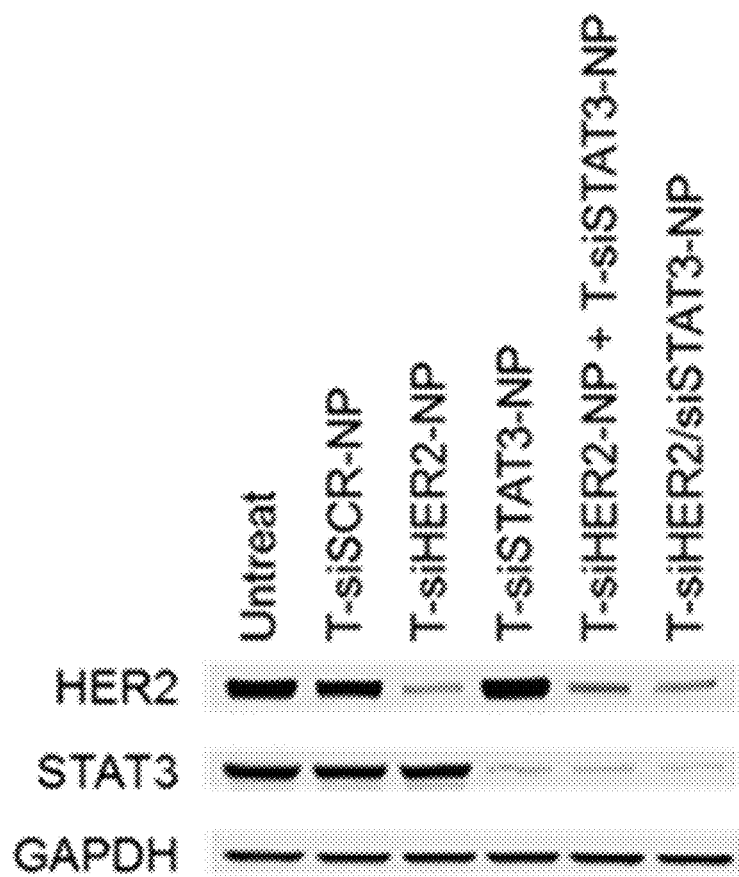
FIG. 13. HCC1954 cells (human HER2+ cancer cells) were treated with trastuzumab-conjugated NP (T-NP) carrying siRNA against HER2 or STAT3. Dose of each siRNA was 30 nM and at 2.0 wt. % of NP throughout. Proteins were analyzed with Western Blot at 72 h post-treatment and indicated 80% knockdown of STAT3 was achieved. Data indicate that the nanoparticles can deliver at least two siRNA sequences (e.g., siHER2 and siSTAT3) without losing the efficacy compared to a single siRNA.
Figure 36:
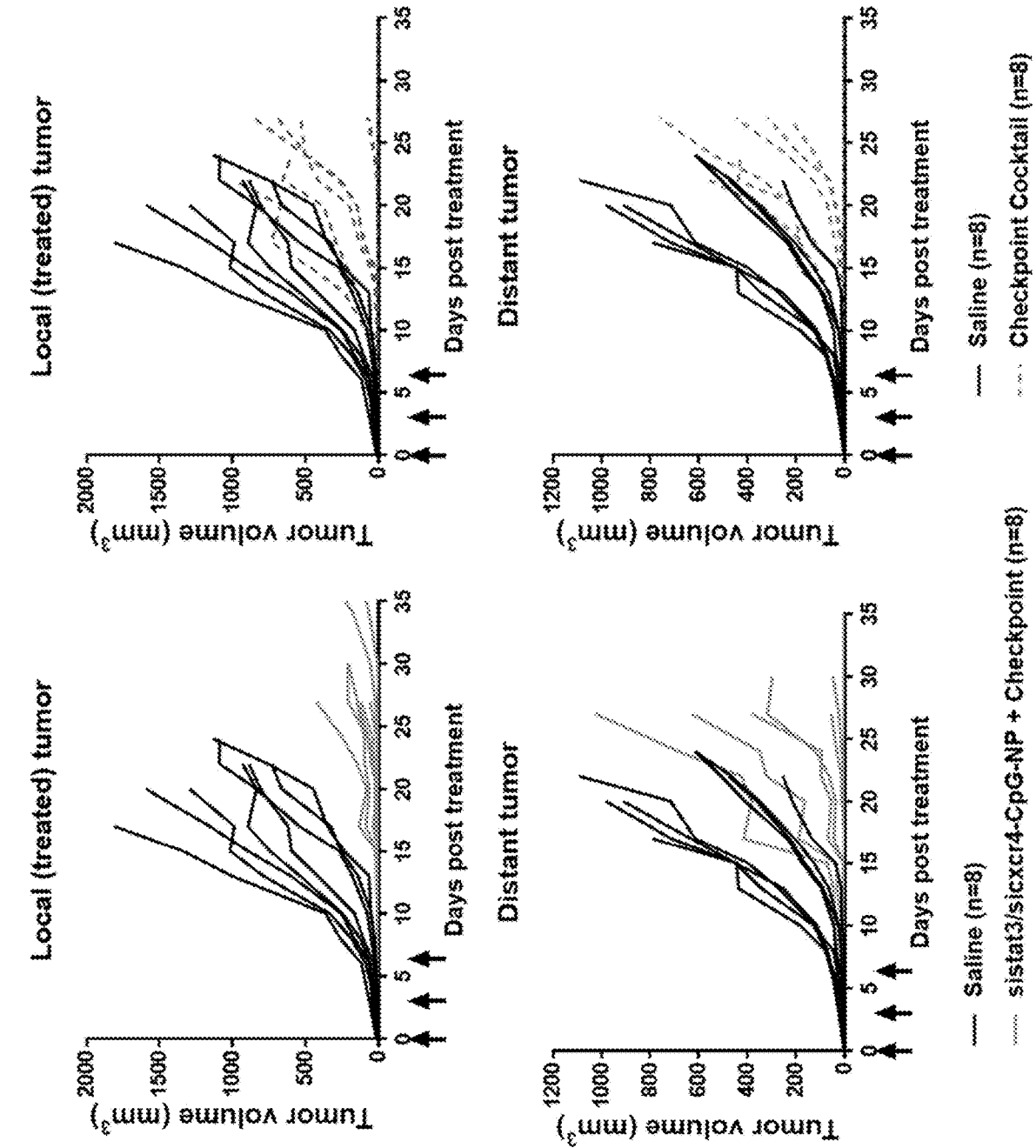
FIG. 36. siSTAT3/siCXCR4-CpG-NP+ICIs are effective in mice bearing aggressive 4T1 breast tumors. 100K and 40K 4T1 cells were implanted into bilateral mammary fat pads of each mouse (Balb/c). 8 days after tumor implantation, mice were treated with ICIs with or without siSTAT3/siCXCR4-CpG-NP in a similar manner to FIGS. 20 and 21 (3 doses; 3 days apart). Tumor growth curves of local treated tumors and distant untreated tumors are plotted as spider plots (each line represents individual mouse). Dose of injection: 16 µg CpG; 5 µg siSTAT3; 5 µg siCXCR4; 0.25 mg NP.

Immunotherapeutic Constructs (Such as NPs) can Also be Loaded with Two Types of siRNAs Simultaneously without Losing Efficacy In addition to co-delivery of siRNA and CpG, the herein-described immunotherapeutic constructs can also co-deliver multiple siRNAs. For example, FIG. 13 shows that when NP (prepared essentially as described in Example 1) was loaded with two individual siRNA against HER2 or STAT3, specific knockdown of each protein was achieved. FIG. 13 also shows that when both siRNAs were loaded on the same NP vial (see T-siHER2/siSTAT3-NP), a similar knockdown of the two proteins was achieved as when they were loaded on two separate NP vials (see T-siHER2-NP+T-siSTAT3-NP). As another example, FIG. 36 shows the effectiveness of NP loaded with siCXCR4, siSTAT3, and CpG (siSTAT3/siCXCR4-CpG-NP) in enhancing the efficacy of immune checkpoint inhibitors in melanoma model.

This illustrates the versatility of the herein described immunotherapeutic constructs particles at loading more than one type of oligonucleotides without losing the efficacy. Nanoparticle delivery as described herein is also beneficial because it allows loading of more than one siRNA that each can kill cancer cells and/or modulate multiple aspects of immunosuppression.

The data shown in FIG. 13 clearly show that NP can deliver an siRNA or a cocktail of two or more different siRNAs, wherein siRNAs may: provide cytotoxic effect to cancer cells, negate immunosuppressive tumor microenvironment, contain immunostimulatory sequences, or have any combination of these characteristics.

Example 3

Cell-Type Specific/Targeted Immunotherapeutic Constructs siRNA holds great potential since any gene can be modulated precisely and effectively. The immunotherapeutic constructs (AIRISE) can tackle different immunosuppressive pathways or different immune cell population by utilizing antibodies (or other targeting agents) on our nanoparticles for specific delivery. Immunotherapeutic constructs, including the NPs provided herein, can be conjugated with targeting agent(s) for targeted-delivery to specific cell population(s), such as specific cells in a tumor. Some antibodies such as anti-PD-L1 antibody may serve as both targeting agents and modulators of immunosuppressive pathways.

Figure 14A:
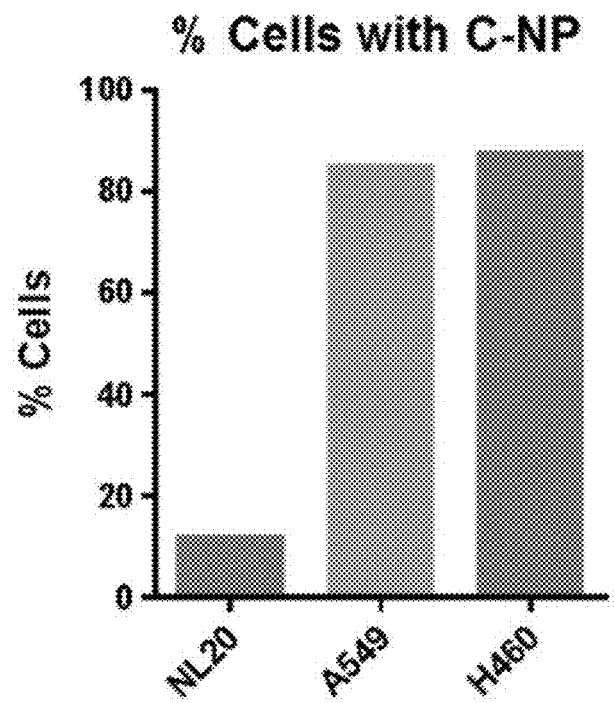
FIGS. 14A-14C. Preferential uptake of nanoparticle containing antibody as homing target agent. After 1 hour of exposure, EGFR antibody (cetuximab) conjugated nanoparticles (C-NP) were preferentially taken up by lung cancer cells overexpressing EGFR (A549 and H460) over normal lung cells (NL20) as shown in FIG. 14A.
Figure 14B:
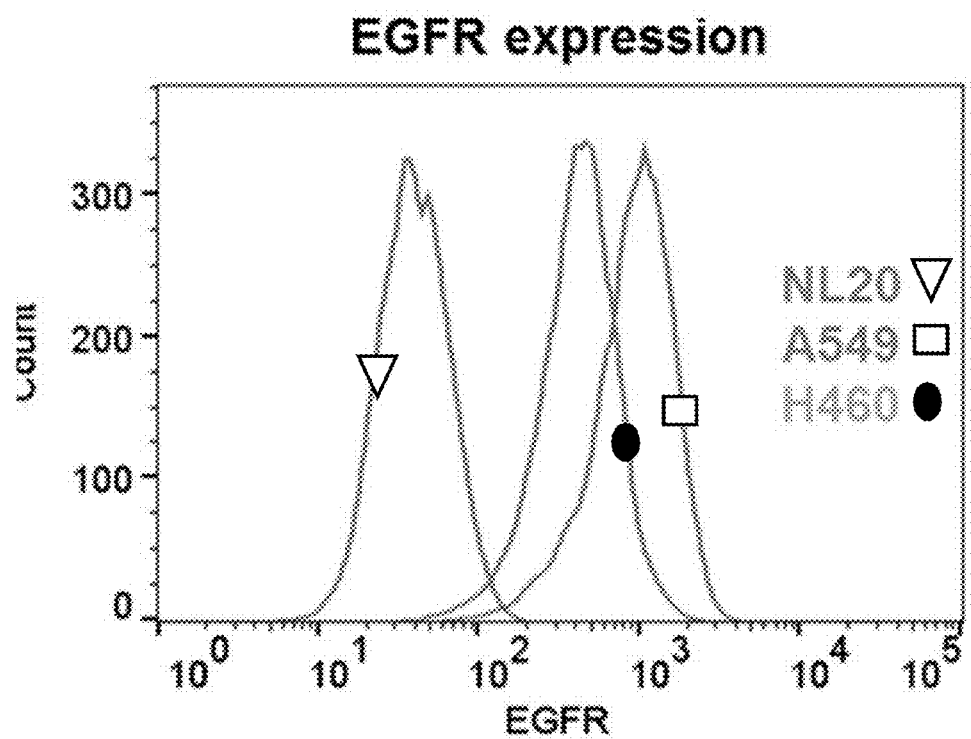
Figure 14C:
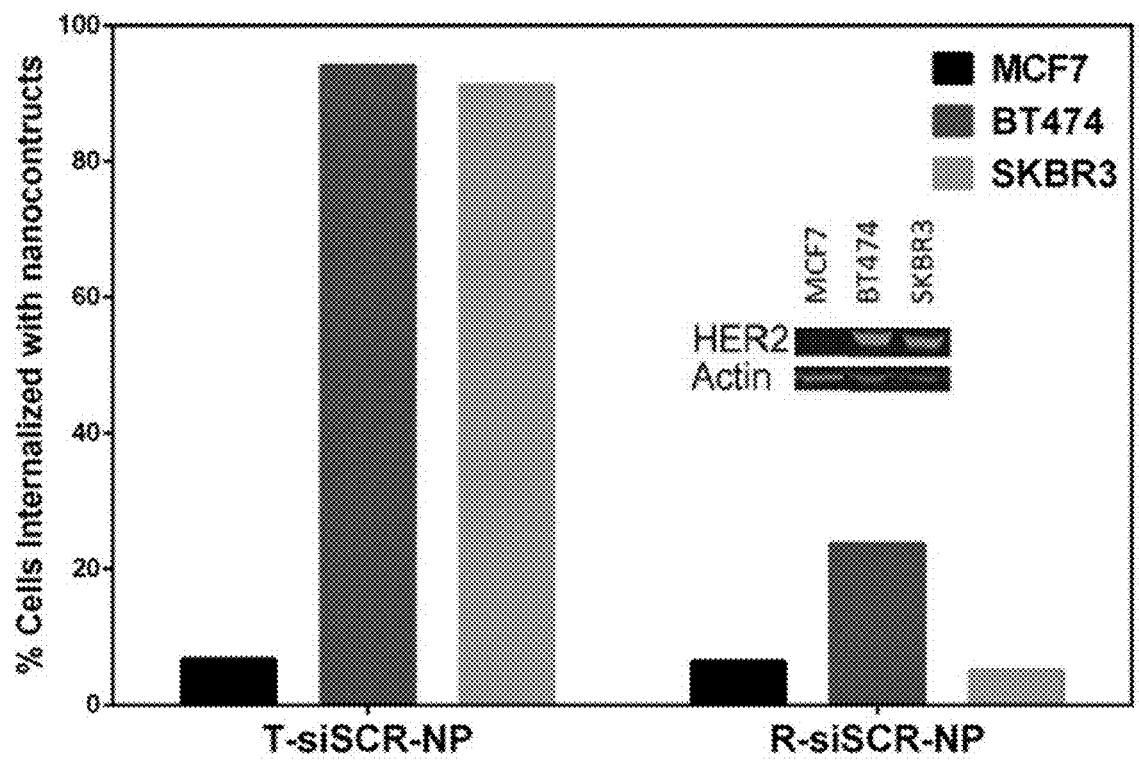

FIGS. 14A-14C provide examples of such targeting of NPs. NP conjugated with cetuximab (anti-EGFR antibody) show preferential uptake to EGFR+ cells over low EGFR cells (FIGS. 14A-14B). Likewise, NP conjugated with trastuzumab (anti-HER2 antibody) shows preferential uptake to HER2+ cells over low HER2 cells (FIG. 14C) (Ngamcherdtrakul et al., Advanced Functional Materials, 25(18):2646-2659, 2015).

It is believed that this type of targeting will work equally well with NPs that are loaded with adjuvant and an active agent, as described herein.

Example 4

Multi-Agent Nanoparticle Treatment

In this example, PD-L1 antibody (mouse PD-L1 from BioXcell) is conjugated on mesoporous silica nanoparticles prepared essentially as in Example 1, which is loaded with a PLK1 inhibitor (volasertib) and CpG. The PD-L1 antibody serves as both an ICI and a tumor-homing agent (targeting agent).

Methods

Volasertib (PLK1 inhibitor; iPLK1) was loaded in excess on the nanoparticle before PEI binding. Briefly, MSNP was mixed with volasertib in ethanol/DMSO solution overnight before PEI binding. Unbound docetaxel or volasertib and PEI were washed out in PBS. PEI-NP(iPLK1) was then conjugated with PEG following previously published methods (Ngamcherdtrakul et al., Advanced Functional Materials, 25(18):2646-2659, 2015; Ngamcherdtrakul et al., International J Nanomed, 13:4015-4027, 2018). The final products contain 0.5-2 wt. % iPLK1. They have the DLS size of 100 nm. For the construct containing PD-L1 antibody (p-NP), PD-L1 antibody was thiolated and conjugated to the end of PEG layer on the nanoparticle following our previously published methods (Ngamcherdtrakul et al., Advanced Functional Materials, 25(18):2646-2659, 2015; Ngamcherdtrakul et al., International J Nanomed, 13:4015-4027, 2018).

LLC-JSP bilateral murine lung tumor model: 6-week-old female C57BL/6 mice were obtained from Charles River NCI colony (Wilmington, Mass.). Each mouse was subcutaneously injected with LLC-JSP cells on the left (local, 100,000 cells) and right (distant, 40,000 cells) flanks. At 12 days post-implantation, test compound/construct was intratumorally injected to only the left (local) tumor, while the right (distant) tumor was left untreated. Unless otherwise specified, the test compound/construct was given every 3 days for 3 doses. Burden of both local and distant tumors in mice were measured with Vernier Caliper every 1-2 days, and tumor volume was calculated by $V=0.5 \times length \times width^2$. Survival was also monitored. Mice were sacrificed when total tumor burden exceeded 2000 mm$^3$.

Results

Figure 15:
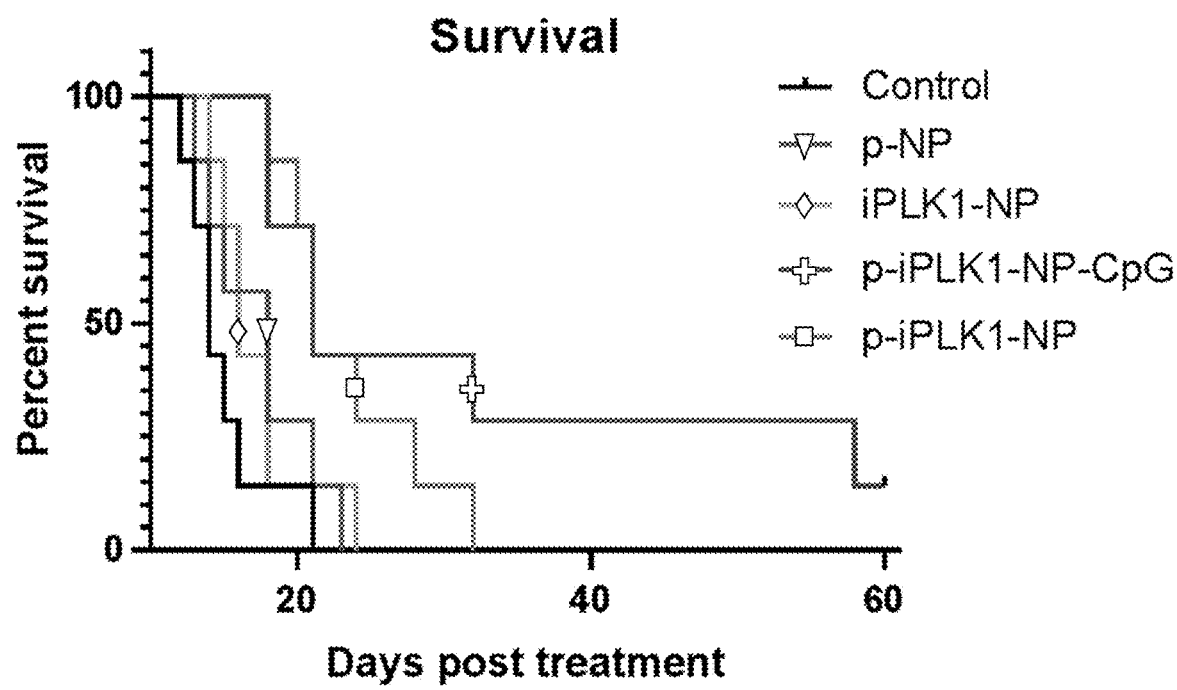
FIG. 15. Adding CpG (SEQ ID NO: 7) to nanoparticles containing PLK1 inhibitor (p-iPLK1-NP) enhances therapeutic benefit as demonstrated by Kaplan Meier Survival curve. 100K LLC-JSP cells (lung cancer cells) were injected in right flank and 40K cells were injected in left flank of C57BL/6 mice. On day 12 post tumor inoculation, mice received intratumoral treatments of saline, PD-L1 antibody coated nanoparticle (p-NP), nanoparticle loaded with PLK1 inhibitor (iPLK1-NP), p-NP loaded with PLK1 inhibitor (p-iPLK1-NP), or p-NP loaded with PLK1 inhibitor and CpG (p-iPLK1-NP-CpG) to the right (local) tumor. 0.5 mg NP (2.5 μg iPLK1, 20 μg PD-L1 antibody, 20 μg CpG) in 50 μl was administered every 3 days for a total of 3 doses.
Figure 16A:
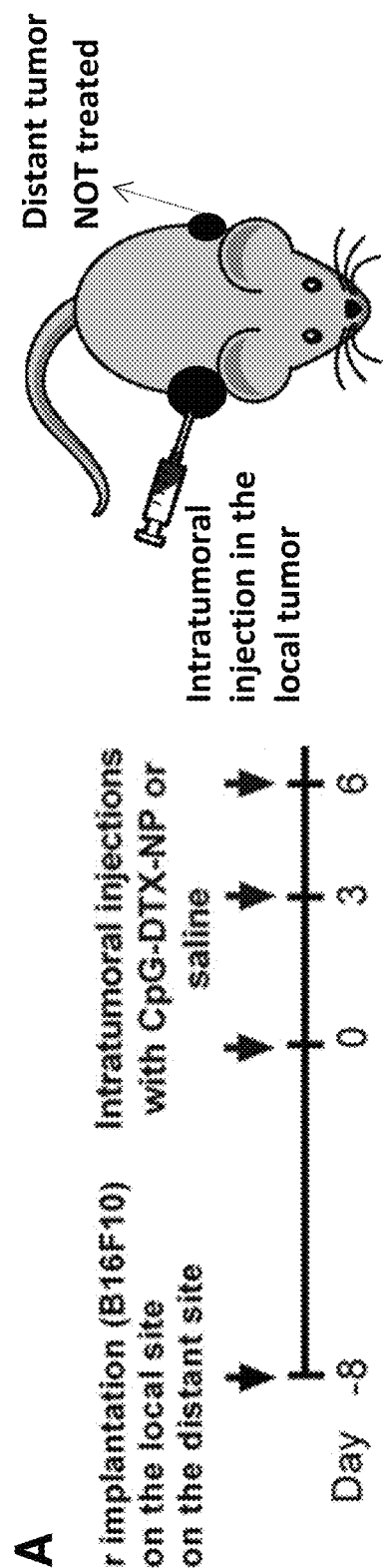
FIGS. 16A-16D. Effectiveness of NP loaded with CpG and mitoxantrone (MTX) administered to a melanoma mouse model as in (FIG. 16A) in inducing in situ tumor vaccination as indicated by inhibited tumor growth curves of local treated tumors (FIG. 16B) and distant untreated tumors (FIG. 16C), and prolonged survival curve of the mice (FIG. 16D). Mice were treated with CpG-MTX-NP or saline. Dose (per each injection): 20 μg CpG; 2 μg MTX; 0.2 mg NP. Tumor volumes are plotted as mean and SEM. For tumor volume, **$p<0.01$ for CpG-MTX-NP vs. Saline.
Figure 16B:
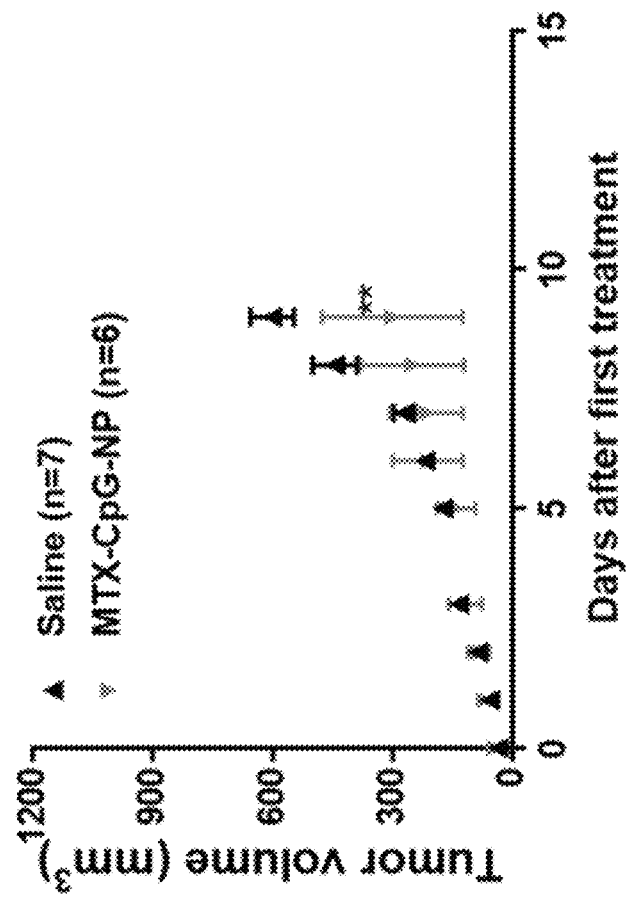
Figure 16C:
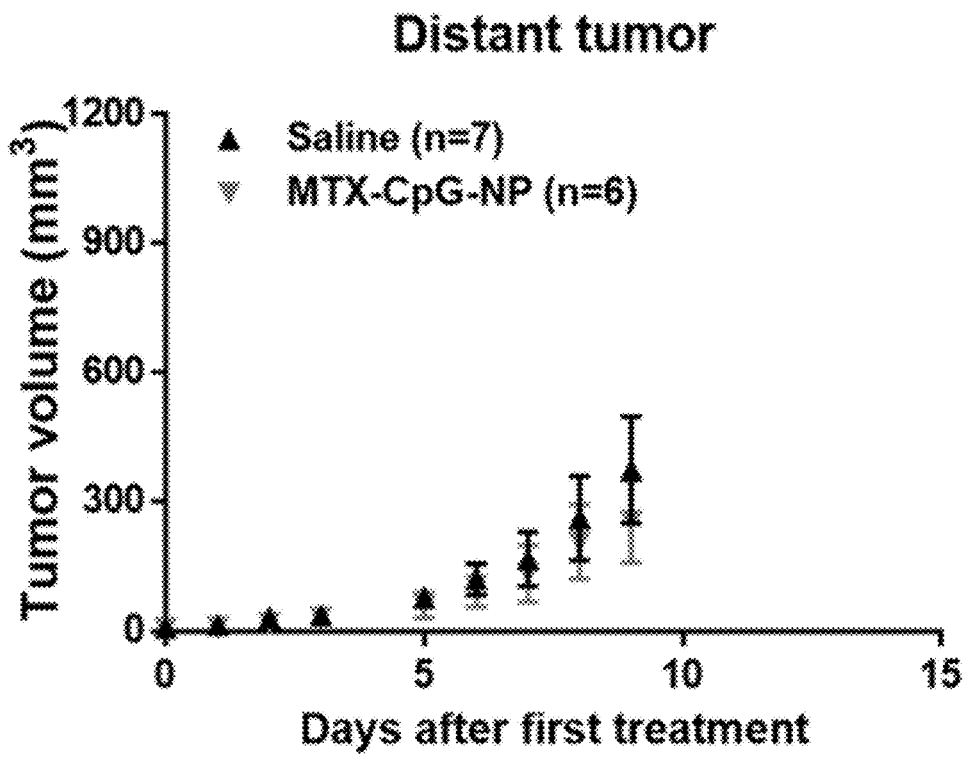
Figure 16D:
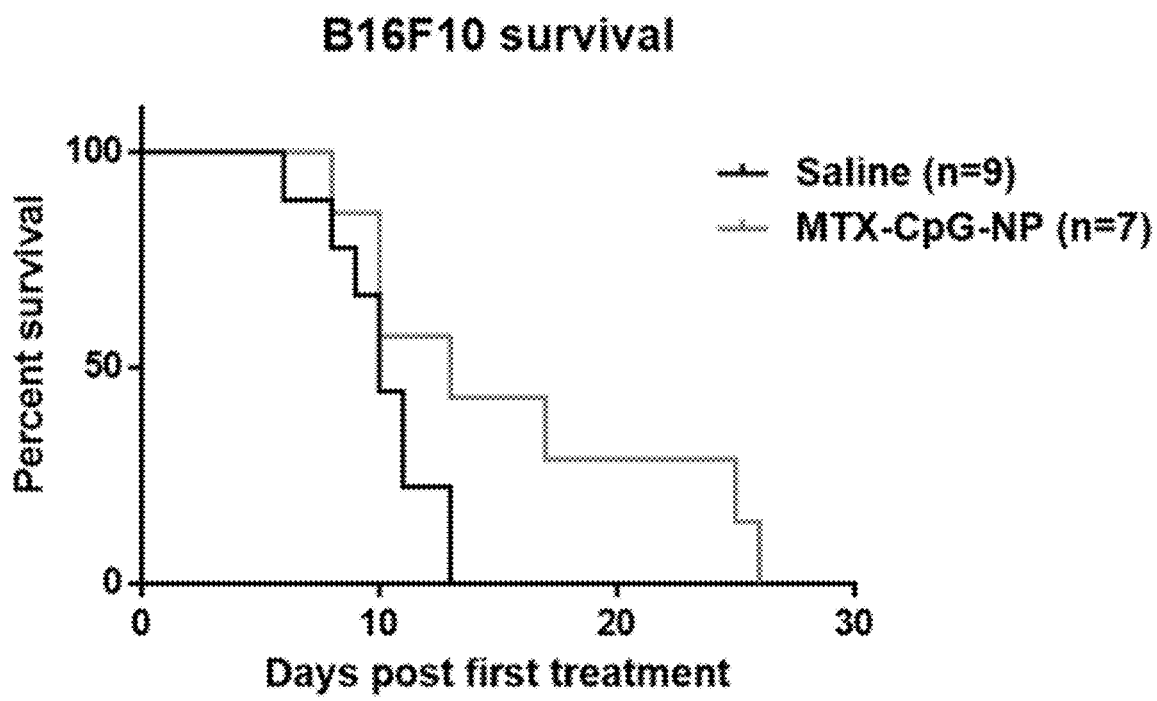

On day 12 post tumor inoculation, mice received intratumoral treatments of saline, PD-L1 antibody coated nanoparticle (p-NP), nanoparticle loaded with PLK1 inhibitor (iPLK1-NP), p-NP loaded with PLK1 inhibitor (p-iPLK1-NP), or p-NP loaded with PLK1 inhibitor and CpG (p-iPLK1-NP-CpG) to the left (local) tumor (while the distant tumor was left untreated). 0.5 mg NP (2.5 µg iPLK1, 20 µg PD-L1 antibody, 20 µg CpG) in 50 µl was administered every 3 days for a total of 3 doses. The immunotherapeutic construct prolonged survival of the mice over the same immunotherapeutic construct but without CpG (FIG. 15). The immunotherapeutic construct was also much more effective than the free PD-L1 antibody and volasertib each given at 5-fold higher concentration of what on the nanoparticle. Incorporating the adjuvant (CpG) on the same NP improved the survival further. For instance, we found that incorporation of CpG on p-iPLK1-NP (referred to as p-iPLK1-NP-CpG) significantly improved survival of 2 out of 7 mice, and one mouse was completely free of tumors.

Example 5

Topical Formulation and Application of AIRISE

The immunotherapeutic constructs disclosed herein can be formulated into topical formulations. Several vehicles known in the art can be mixed with the construct, e.g., Aquaphor (ointment-based) and Carbopol (gel-based). Heat or surfactant (e.g., Polysorbate 80 (Tween 80) as an emulsifier) can be used to allow better mixing of the vehicle and an aqueous suspension of AIRISE. As an example, it was confirmed that 10 wt. % Tween-80 did not cause any premature leakage of siRNA from the nanoparticle. It was also shown that 2.5 wt. % Tween-80 was sufficient to enhance the mixing of siRNA-NP and Aquaphor upon warming the mixture to 55° C.

Methods to enhance penetration simultaneously can be used, such as ultrasound and microneedle rollers (e.g., Dermaroller® with the needle height ranging from 0.5 mm to 1.5 mm). Application of microneedles with needle height as short as 0.5 mm can enhance penetration of topical siRNA-nanoparticle formulation when tested in pig skin (FIG. 30) and in mice (FIG. 31).

Figure 30:
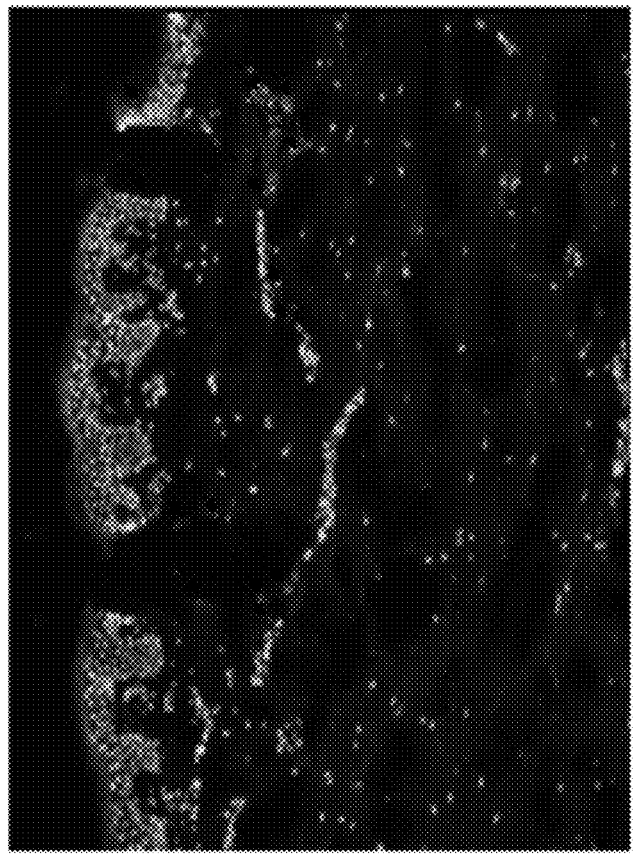
FIG. 30. Topical siRNA-NP in pig skin with and without microneedle roller pre-treatment. Fluorescent images of pig skin treated with one topical application of Dy677-siSCR-NP in Aquaphor for one hour with and without pre-treating skin with a microneedle roller. siRNA signal is noted with arrows. Tissues were also stained for nuclei with Hoechst 33342.
Figure 30:
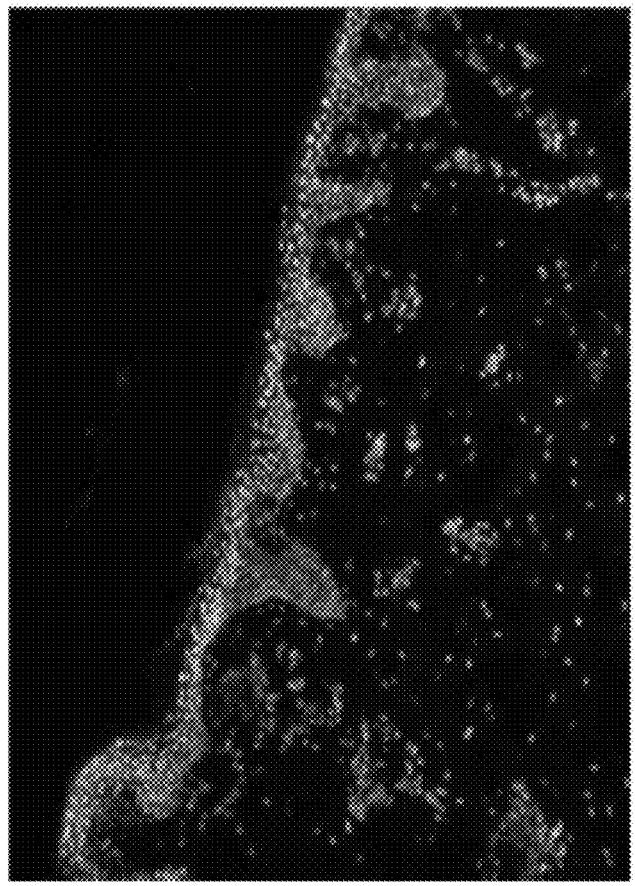

FIG. 30 shows that microneedle roller enhances penetration of siRNA nanoparticle construct when tested in pig skin, which is similar in thickness to human skin. Pig skins were incubated with the formulation (Dy677-siSCR-NP in Aquaphor) for 1.5 h (37° C.; 5% CO2). After 1.5 hours, a skin punch was taken from the treated area and processed for fluorescent imaging using a standard approach.

Significant enhancement in skin penetration with a microneedle roller was observed. While siRNA signal (arrows) was confined to the outer surface of the pig skin when siRNA-NP in Aquaphor was given without a roller, we observed siRNA signal (arrows) past the epidermis down to the dermis layer with microneedle pre-application (FIG. 30).

Figure 31:
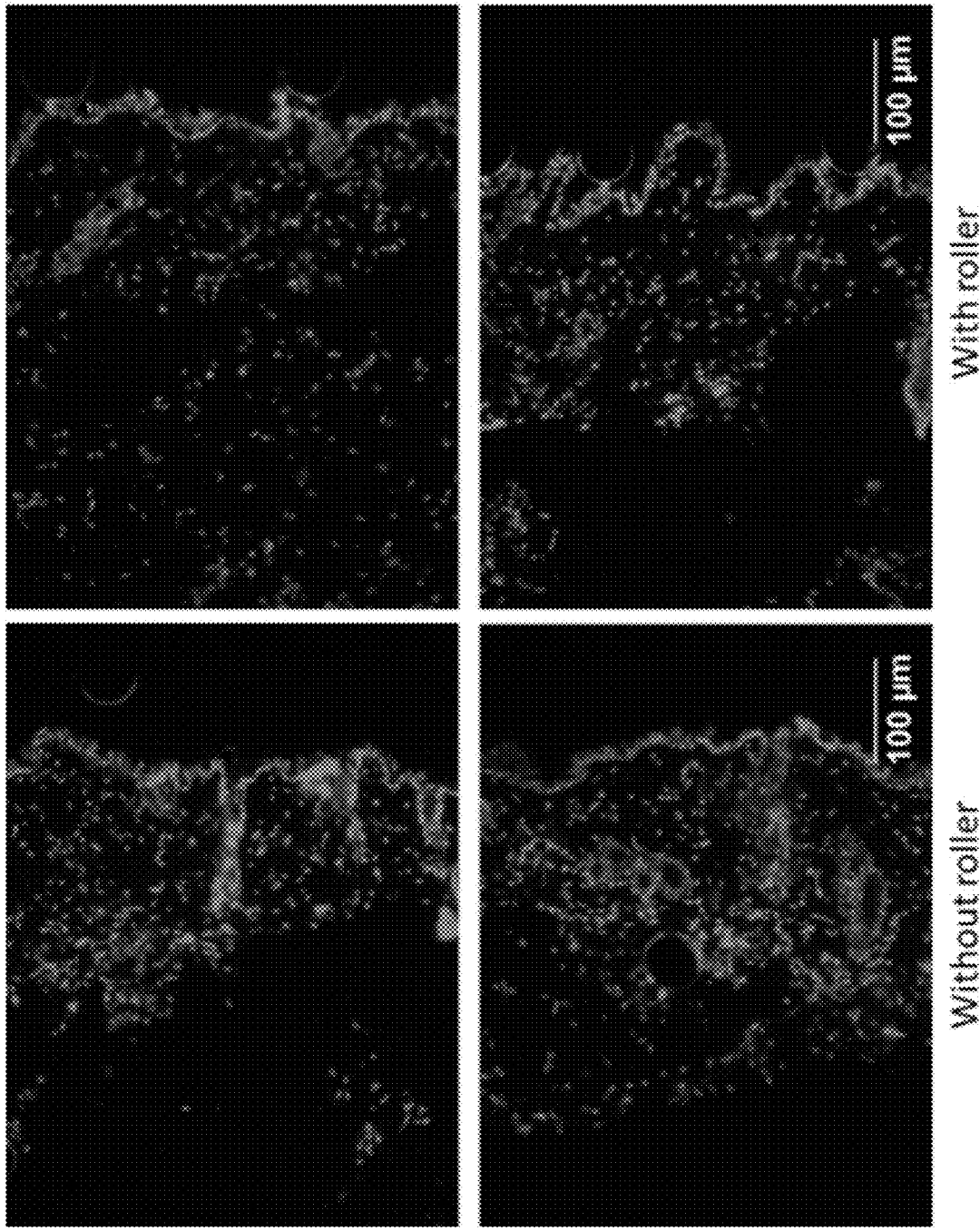
FIG. 31. Topical siRNA-NP/Tween-Aquaphor in mice with and without microneedle roller pre-treatment. Fluorescent images of mouse skin treated with one topical application of Dy677-siSCR-NP in Tween/Aquaphor for 1.5 hour with and without pre-treating skin with a microneedle roller. siRNA signal is noted with arrows. Tissues were also stained for nuclei with Hoechst 33342.

FIG. 31 shows that microneedle roller enhances topical delivery of siRNA-NP. First, mice were shaved one day before treatment. Dy677-siSCR-NP (0.72 nmol siRNA) was mixed with 100 µl of 2.5% Tween-Aquaphor (per one application). Right before treatment, a dermal microroller was applied to only one side of the back in four directions consistently, while the other side was not pre-treated. The mixture was applied to the shaved area (approximately 2 cm$^2$ application area) with and without microneedle pre-treatments for comparison. After 1.5 hr of treatment time, treated skin samples were harvested and processed for imaging.

Figure 32A:
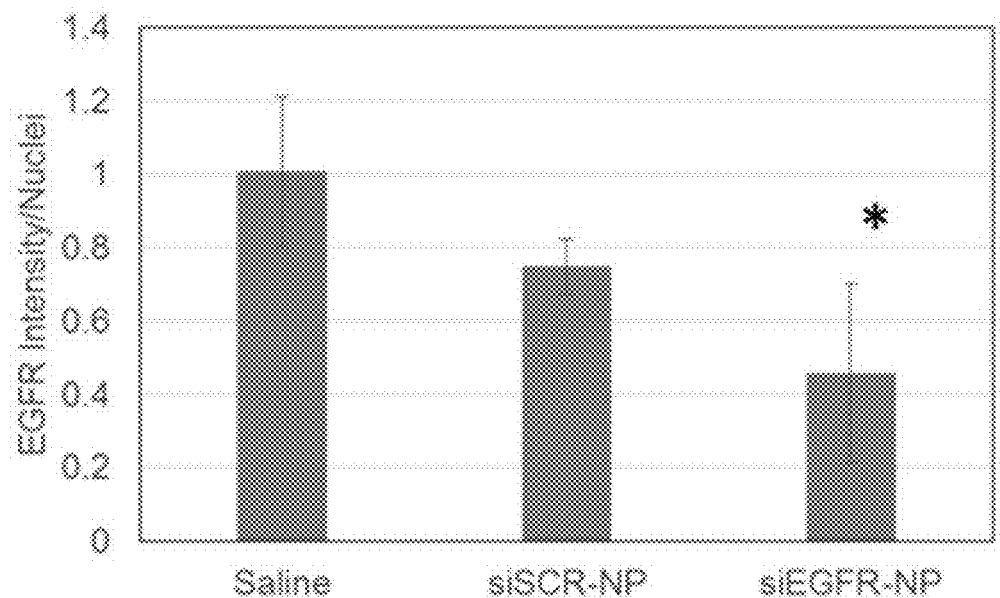
FIGS. 32A-32B. EGFR knock down efficacy of topical siRNA-NP with microneedle roller versus injected siRNA-NP. Mouse skin was harvested at 3 days after one topical treatment with siEGFR-NP or siSCR-NP in Tween/Aquaphor with microneedle roller application (FIG. 32A) or 3 days after one injection of siEGFR-NP or siSCR-NP in saline (FIG. 32B). Skin tissue was fixed and stained with fluorescently labelled EGFR antibody for EGFR signal quantification. 4-8 images (20×) were processed per condition and 3 animals per group.
Figure 32B:
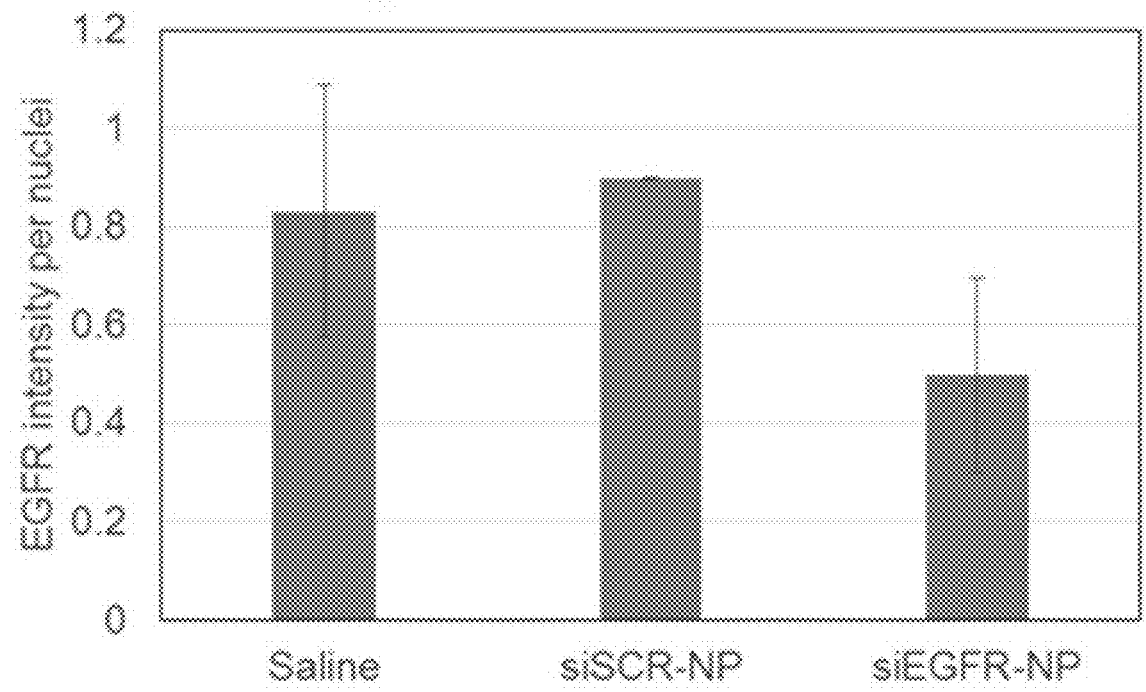

FIG. 32 show the resulting gene knockdown at 3 days after microroller+topical siRNA nanoconstruct application. A 55% EGFR knockdown in siEGFR-NP versus saline treated group (*p<0.05) (FIG. 32A) was observed. In comparison, one intradermal injection of siEGFR-NP (with same siEGFR dose of 0.72 nmol) resulted in 40% EGFR knock down versus saline treated groups (FIG. 32B).

Figure 33:
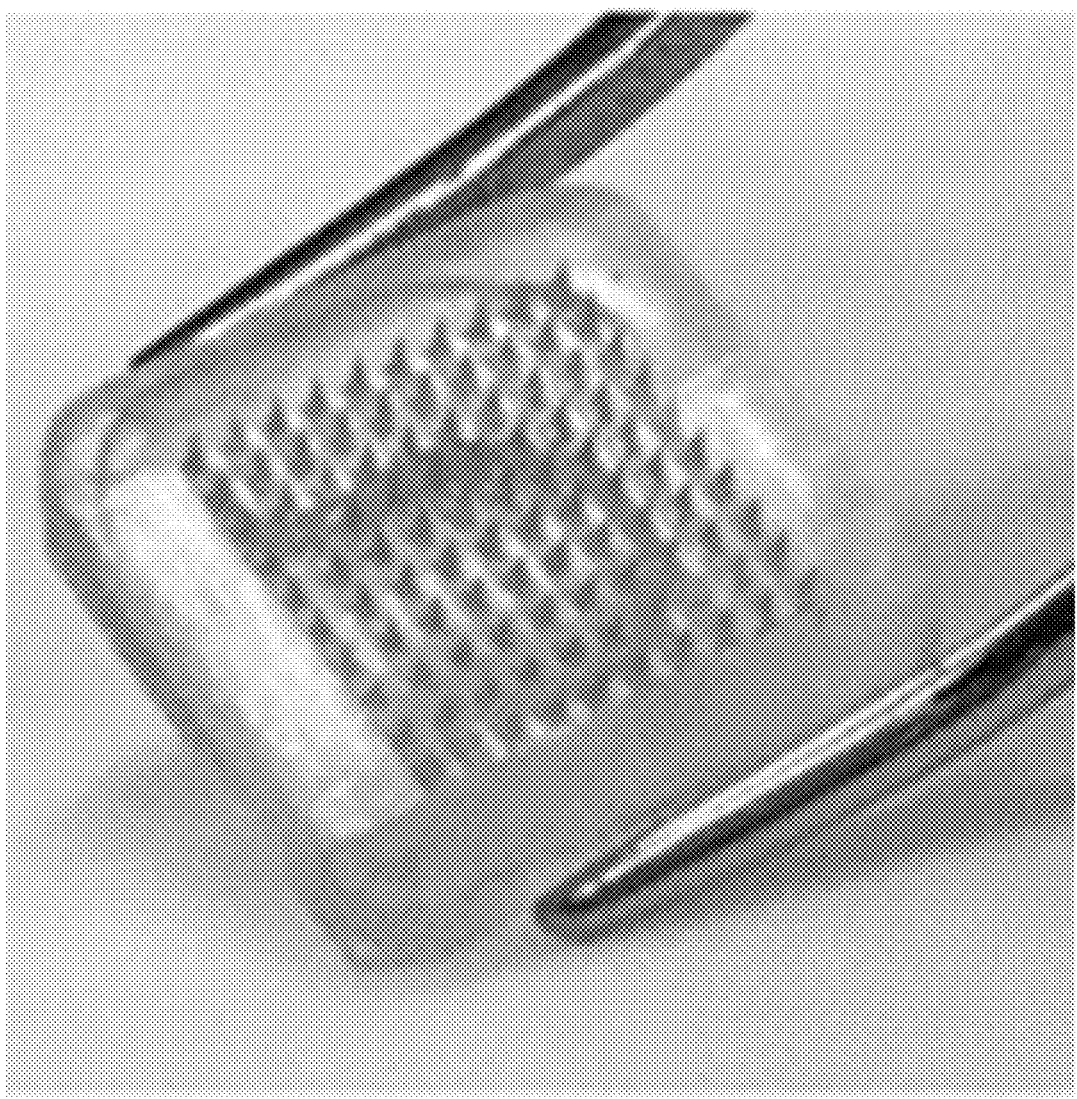
FIG. 33. Dextran-based microneedle containing NP loaded with Dy677-siRNA

Microneedle form of AIRISE-02. The use of dissolvable microneedles based on dextran, amylopectin, PVP, PEG, methylcellulose, chitosan, or other polymers or compounds known in the arts were explored for microneedle fabrications, as shown in FIG. 33, which allow for painless in-home treatment and are highly effective at delivering AIRISE-02 owing to high needle density (100 needles per 1 cm$^2$). As an example (FIG. 33), a dextran solution (300 mg/ml in water) containing NP loaded with Dy677-conjugated siRNA was cast onto a microneedle mold. The solution was centrifuged or vacuumed to fill the mold compactly. The microneedle was dried by air, desiccator, vacuum oven, fridge, or combination thereof and removed from the mold. Heights of the needles varied from 300 to 800 microns depending on the templates and optimization. siRNA-NP was successfully loaded into these needle arrays (at about 0.5 nmol siRNA per array) and the needles were fully dissolved within 5 min after applying to pig skins. Different dissolving time can be engineered by varying the ingredients of the microneedles. Microneedle patches of different shape and forms can also be manufactured with different templates.

Example 6

Figure 11D:
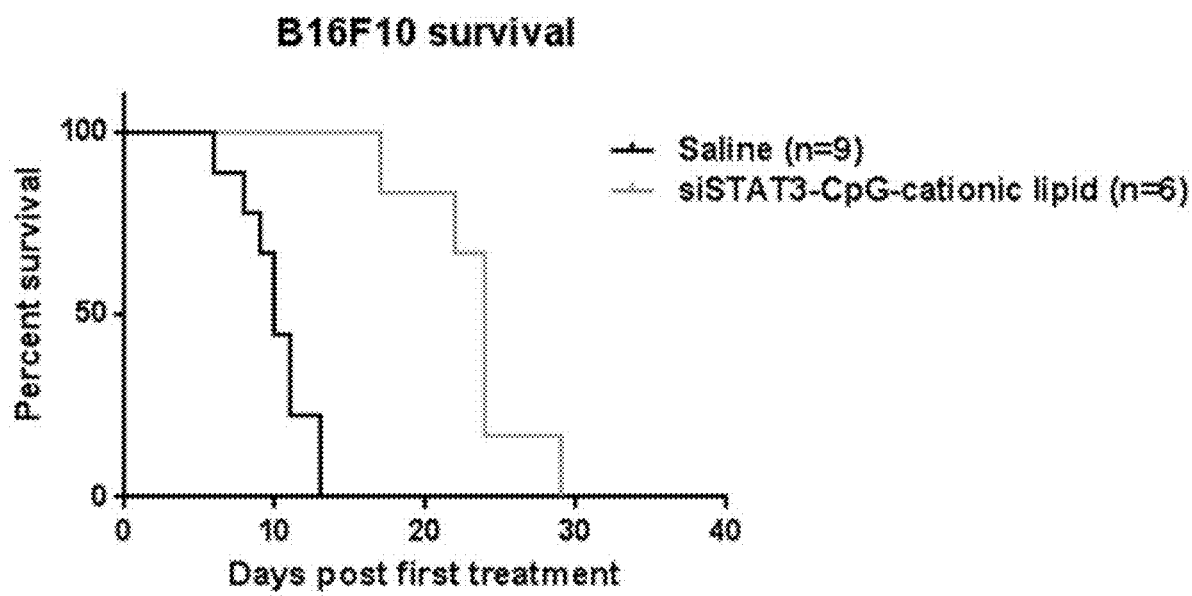

Different Nanoparticle Materials can be Used to Deliver the Disclosed Cargo Combinations and Produce Similar Immunotherapeutic Effects As an example, siSTAT3 and CpG were loaded on cationic lipid particles (Dharmafect®; commercially available) and administered to mice in the same manner as Example 1 (AIRISE-02 based on mesoporous silica). It was found that CpG and siSTAT3 delivered with the cationic lipid particles also yielded an in situ tumor vaccination/immunostimulatory effect (FIG. 11). A similar outcome was also obtained using jetPEI (commercially available PEI-based transfection agent that reached clinical stages) as the delivery system. This shows the versatility of the disclosed cargo combination and agnostic nature in terms of delivery platform. However, it's worth nothing that while lipid platform is generally effective in delivering siRNA to cancer cells, the layer-by-layer functionalized mesoporous silica nanoparticles (as described herein) show better siRNA knock down activity in immune cells (e.g., primary dendritic cells) than lipid counterpart (FIG. 12).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect, in this context, is a measurable reduction in a biological impact (such as an anti-cancer effect) of an immunotherapeutic construct.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the example(s) or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. An immunotherapeutic construct comprising:
   a nanoparticle platform (NP) comprising:
      a mesoporous silica nanoparticle (MSNP);
      polyethylenimine (PEI) coating an exterior surface of the MSNP;
      polyethylene glycol (PEG) bound to the PEI or to the MSNP;
   an siRNA that inhibits expression or an activity of STAT3 (siSTAT3) non-covalently attached to the PEI; and
   an adjuvant comprising a CpG oligonucleotide non-covalently attached to the PEI, wherein the immunotherapeutic construct does not comprise a tumor-specific antigen or ovalbumin.

2. The immunotherapeutic construct of claim 1, wherein the PEI is cross-linked.

3. The immunotherapeutic construct of claim 1, wherein the CpG oligonucleotide is CpG ODN 7909 (SEQ ID NO: 8).

4. The immunotherapeutic construct of claim 1, wherein the MSNP has a size of about 30-80 nm.

5. The immunotherapeutic construct of claim 1, having a hydrodynamic size of about 80 nm to 200 nm.

6. The immunotherapeutic construct of claim 1, wherein the siRNA is 0.5 to 10% by weight of the immunotherapeutic construct.

7. The immunotherapeutic construct of claim 1, wherein the adjuvant is 0.5 to 20% by weight of the immunotherapeutic construct.

8. A composition comprising:
   the immunotherapeutic construct of claim 1; and
   at least one pharmaceutically acceptable carrier, excipient, diluent, or mixture thereof.

9. A method of treating a subject diagnosed as having a hyperproliferative disease or condition or having a high-risk of developing such disease or condition, comprising administering to the subject an effective amount of the composition of claim 8.

10. The method of claim 9, wherein the subject is a mammal.

11. The method of claim 9, wherein the mammal is a human.

12. The method of claim 9, wherein the hyperproliferative disease or condition comprises one or more of cancer, pre-cancer, or cancer metastasis.

13. The method of claim 12, wherein the hyperproliferative disease comprises one or more of melanoma, lung cancer, breast cancer, pancreatic cancer, brain cancer, prostate cancer, head and neck cancer, kidney cancer, colorectal cancer, lymphoma, gastric cancer, colon cancer, liver cancer, ovarian cancer, or bladder cancer.

14. The method of claim 9, wherein the administering comprises:
   injection to or at a tumor in the subject;
   infusion locally to or at a tumor in the subject;
   systemic injection in the subject;
   systemic infusion in the subject; or
   topical application to the subject.

15. The method of claim 9, wherein the administering comprises microneedle application to the subject.

16. The method of claim 9, further comprising administering
   an anti-cancer therapy, wherein the anti-cancer therapy comprises an anti-cancer agent or a radiation therapy.

17. The method of claim 16, wherein the immunotherapeutic construct is administered with the anti-cancer agent.

18. The method of claim 17, wherein the anti-cancer agent is a chemotherapeutic agent, a targeted therapeutic agent, or an immune checkpoint inhibitor.

19. The method of claim 18, wherein the anti-cancer agent is an immune checkpoint inhibitor selected from a PD-L1 antibody, a PD-1 antibody, a CTLA4 antibody, or a combination thereof.

20. The method of claim 16, wherein the immunotherapeutic construct is administered with the radiation therapy.

21. The method of claim 16, wherein the immunotherapeutic construct and the anti-cancer therapy are administered sequentially or concurrently.

* * * * *